US012611147B2

(12) United States Patent
Persaud et al.

(10) Patent No.: US 12,611,147 B2
(45) Date of Patent: Apr. 28, 2026

(54) DEVICES TO INFORM HEALTHCARE WORKERS OF PAIN, DATA SCIENCE AND ARTIFICIAL INTELLIGENCE-RELATED METHODS AND SYSTEMS TO UNDERSTAND PAIN

(71) Applicants: Christopher Persaud, Winnetka, CA (US); Loknath Persaud, Winnetka, CA (US)

(72) Inventors: Christopher Persaud, Winnetka, CA (US); Loknath Persaud, Winnetka, CA (US)

( * ) Notice: Subject to any disclaimer, the term of this patent is extended or adjusted under 35 U.S.C. 154(b) by 15 days.

(21) Appl. No.: 19/007,319

(22) Filed: Dec. 31, 2024

(65) Prior Publication Data

US 2026/0053449 A1     Feb. 26, 2026

Related U.S. Application Data

(60) Provisional application No. 63/686,734, filed on Aug. 24, 2024.

(51) Int. Cl.
| | |
|---|---|
| *A61B 5/00* | (2006.01) |
| *G08B 5/36* | (2006.01) |

(Continued)

(52) U.S. Cl.
CPC ............ *A61B 5/746* (2013.01); *A61B 5/0004* (2013.01); *A61B 5/4824* (2013.01); *A61B 5/742* (2013.01);

(Continued)

(58) Field of Classification Search
CPC .................... A61B 2560/0228; Y02T 10/7072

(Continued)

(56) References Cited

U.S. PATENT DOCUMENTS

| | | |
|---|---|---|
| 5,634,472 A | 6/1997 | Raghuprasad |
| 5,653,739 A | 8/1997 | Kalm et al. |

(Continued)

FOREIGN PATENT DOCUMENTS

| | | |
|---|---|---|
| EP | 0438541 | 11/1995 |
| EP | 2359746 | 12/2018 |

(Continued)

OTHER PUBLICATIONS https://www.boozallen.com/insights/ai/nih-combats-cancer-pain-using-artificial-intelligence.html.
Gretton et. al., "A Kernel Method for the Two-Sample Problem", https://arxiv.org/PS_cache/arxiv/pdf/0805/0805.2368v1.pdf.

*Primary Examiner* — Fabricio R Murillo Garcia

(57) ABSTRACT

The invention includes a group of devices allowing people to indicate when and where they experience pain or discomfort, and a system and method for using this information to improve clinical medical care. The user can indicate, with the user's finger, tongue, or in other ways, where on the user's body, or in the user's mouth, the user is experiencing pain, and the pain's intensity. Some versions of the invention include models of parts or all of a person's body, so the user can show where, and how much, pain is being experienced. The invention also includes a group of programs and databases for monitoring the pain users experience and for drawing conclusions about modifying medical and dental procedures to reduce pain that patients experience. The invention can also be used to monitor other sensations such as "itchiness".

24 Claims, 19 Drawing Sheets

(51) Int. Cl.
| | |
|---|---|
| *G09B 23/30* | (2006.01) |
| *G16H 40/63* | (2018.01) |
| *G16H 50/30* | (2018.01) |

(52) U.S. Cl.
CPC .............. *G08B 5/36* (2013.01); *G09B 23/30* (2013.01); *G16H 40/63* (2018.01); *G16H 50/30* (2018.01); *A61B 2560/0214* (2013.01)

(58) Field of Classification Search
USPC ....................................................... 340/573.1
See application file for complete search history.

(56) References Cited

U.S. PATENT DOCUMENTS

| | | | |
|---|---|---|---|
| 5,692,500 | A | 12/1997 | Gaston-Johansson |
| 6,044,303 | A | 3/2000 | Kipnis et al. |
| 8,123,683 | B2 | 2/2012 | Douglass et al. |
| 8,868,172 | B2 | 10/2014 | Leyde et al. |
| 9,788,917 | B2 | 10/2017 | Mah |
| 10,019,430 | B2 | 7/2018 | Rossi et al. |
| 11,101,028 | B2 | 8/2021 | Mason |
| 11,107,591 | B1 | 8/2021 | Mason |
| 11,110,276 | B2 | 9/2021 | Moffitt et al. |
| 11,123,562 | B1 | 9/2021 | Pulliam et al. |
| 11,173,245 | B2 | 11/2021 | Osorio |
| 11,207,100 | B2 | 12/2021 | Donovan et al. |
| 11,235,146 | B2 | 2/2022 | Boggs, II et al. |
| 11,241,191 | B2 | 2/2022 | Zeller et al. |
| 11,259,708 | B2 | 3/2022 | Zuckerman-Stark et al. |
| 2001/0037222 | A1 | 11/2001 | Dunbar et al. |
| 2002/0115913 | A1 | 8/2002 | Schmidt et al. |
| 2002/0123906 | A1 | 9/2002 | Reid et al. |
| 2003/0171659 | A1 | 9/2003 | Dean |
| 2004/0267099 | A1 | 12/2004 | Daynes et al. |
| 2005/0267338 | A1 | 12/2005 | Lipman |
| 2006/0052720 | A1 | 3/2006 | Ross et al. |
| 2006/0178595 | A1 | 8/2006 | Schatteman |
| 2006/0235489 | A1 | 10/2006 | Graves et al. |
| 2007/0179349 | A1 | 8/2007 | Simms et al. |
| 2009/0259113 | A1 | 10/2009 | Liu et al. |
| 2011/0136090 | A1* | 6/2011 | Kazemi ................ G09B 23/283 |
| | | | 434/263 |
| 2013/0231578 | A1* | 9/2013 | Takayanagi ............ A61B 5/743 |
| | | | 600/521 |
| 2014/0276549 | A1 | 9/2014 | Osorio |
| 2014/0344740 | A1* | 11/2014 | Kaula ................. G06F 3/04842 |
| | | | 715/771 |
| 2014/0354436 | A1* | 12/2014 | Nix ..................... G06F 3/04817 |
| | | | 340/573.1 |
| 2015/0025334 | A1 | 1/2015 | Jain |
| 2015/0025335 | A1 | 1/2015 | Lakshya |
| 2015/0366518 | A1* | 12/2015 | Sampson ............. A61B 5/7264 |
| | | | 600/509 |
| 2016/0232416 | A1 | 8/2016 | Rossi |
| 2016/0246944 | A1 | 8/2016 | Lakshya et al. |
| 2016/0262691 | A1 | 9/2016 | Lakshya |
| 2016/0306946 | A1 | 10/2016 | Harbut et al. |
| 2016/0354031 | A1 | 12/2016 | Shetake et al. |
| 2017/0055915 | A1 | 3/2017 | Jain et al. |
| 2018/0033261 | A1 | 2/2018 | Mayer et al. |
| 2018/0085055 | A1 | 3/2018 | Annoni et al. |
| 2018/0169335 | A1 | 6/2018 | Baronov et al. |
| 2019/0335999 | A1 | 11/2019 | Roy et al. |
| 2019/0336069 | A1* | 11/2019 | Dullen ................. A61B 5/0024 |

FOREIGN PATENT DOCUMENTS

| | | |
|---|---|---|
| EP | 3867925 | 8/2021 |
| WO | WO199916407 | 4/1999 |
| WO | WO200221447 | 3/2002 |
| WO | WO2003105686 | 12/2003 |
| WO | WO2014118022 | 8/2014 |
| WO | WO2016025989 | 2/2016 |
| WO | WO2016081830 | 5/2016 |
| WO | WO2016156171 | 10/2016 |
| WO | WO2020156979 | 8/2020 |
| WO | WO2020257874 | 12/2020 |
| WO | WO2021037260 | 3/2021 |
| WO | WO2021050972 | 3/2021 |
| WO | WO2021062358 | 4/2021 |

* cited by examiner

DEVICES TO INFORM HEALTHCARE WORKERS OF PAIN, DATA SCIENCE AND ARTIFICIAL INTELLIGENCE-RELATED METHODS AND SYSTEMS TO UNDERSTAND PAIN

This patent application claims priority to U.S. provisional patent application 63/686,734, filed Aug. 24, 2024 with Christopher Persaud and Loknath Persaud as the inventors.

This patent application is dedicated to Arabella Persaud, wife of one of the inventors and mother of the other inventor.

INITIAL DEFINITIONS

These definitions shall apply for the purposes of this patent application. For purposes of this patent application, all types of dentists, orthodontists, all types of physicians, all types of nurses, dental hygienists, psychologists and other mental health professionals, psychiatrists, genetic counselors, occupational therapists, speech pathologists, orthodontists, optometrists, midwives, podiatrists, audiologists, chiropractors, doulas, physicians' assistants, and other licensed healthcare professionals, and their assistants, and people working at hospitals or medical or dental offices or clinics, who are working in that capacity at the time, shall be referred to collectively as "healthcare providers" from this point on. Physical therapists and personal trainers, hospitals and other healthcare-providing institutions, and health insurance companies, are also specifically considered healthcare professionals for this application's purposes.

The "degree" of pain, or "pain degree" is the amount, or intensity, of pain that a user is experiencing. Something more painful will cause a higher pain degree than something less painful. A user can simultaneously experience different degrees of pain in different body parts. For example, a user may experience a high pain degree in his right leg while simultaneously experiencing a low pain degree in his left leg.

The "location" of pain is the body part of the user which she feels to be in pain. Pain's location can be one of the user's teeth, for example, if the user is experiencing pain there. The location where the user is feeling the pain will not always be the same body part of the user that is in physical distress, because of how human nervous systems are designed. For example, a patient experiencing a heart attack may feel pain shooting up his/her arm. The pain's source is really the user's heart, not the user's arm. The pain's location is the arm for the invention's purposes. This application considers the pain's "location" to be the user's body part where the user feels the pain originates, which may not be the same as the body part really in distress.

The "type" of the pain, or "pain type" is the user's assessment of the way the pain feels, for example, throbbing pain, dull pain, and stabbing pain are types of pain. Other pain types are aching pain, allodynia, burning pain, cutting pain, freezing pain, numbness, shooting pain, squeezing pain, stinging pain, pain that causes a feeling of stretching, tingling pain, and pain that the user experiences, if he/she tries to move a "stiff" body part. So are sharp pain, aching, cramping, shooting pain, pressure pain, heavy pain, tender pain, prickly pain, and stinging pain. The "type" of the pain shall be up to the user, who, realistically, will be the only one who knows how the pain feels. Some embodiments of the invention will allow the user to indicate which of these pain types he/she is feeling in multiple body parts.

A user can experience a certain degree and/or type of pain in one location, while experiencing a different degree and/or type of pain at the same time in a different location.

A "response" is when an individual user uses the invention to show that he/she is feeling pain. For example, it is a response if the user presses one of the pain indicator units (defined in the "The Components" section) that is in the form of a pain indicator button, or one of the pain indicator virtual units, or a pain indicator skin. A response ideally includes any of the below kinds of information, that the user reveals in the response, if the instrument, including any pain indicator unit(s), pain indicator skin(s), or pain indicator virtual unit(s) (all of which are defined in the "The Components" section) used to make the response, is capable of registering this information: A. The location, time, intensity, and type, of the pain the user is experiencing. B. The duration of the time the user activates the pain indicator unit(s), pain indicator skin(s), or pain indicator virtual unit(s). C. The user's user ID.

A user can make two or more responses at the same time, to indicate that he/she is feeling pain in two or more body parts at the same time. The responses need not have the same degree, kind, location, or length.

Information is "registered" on art input device (defined below) when an input device receives the information as part of a response. For example, when a user indicates that he/she is feeling pain on an input device that is designed so that the user cannot designate the location on his/her body where he/she is feeling pain. then the location of the user's pain will not he registered. The fact that the user is feeling pain will be registered, because the input device is capable of receiving the information that the user is feeling pain as part of a response. The response thus created will include the fact that the user is feeling pain. Registered resporises on an input device that the user has acknowledged that he/she is using, in a way that the centralized program (45) would receive the acknowledgment are an expressed information category.

If an input device is not capable of registering the pain type that a user feels, then the pain type simply will not be registered when the user uses that input device to make a response, and will be ignored during later data analysis involving that response. Likewise, if an input device is not capable of registering the pain degree that a user feels, then the pain degree simply will not be registered when the user uses that input device to make a response, and will be ignored during later data analysis involving that response.

The "Databases" are the Individual Database (11), the Centralized Integrated Database (10) and the Specialized Databases (33), and the app database (44) which are defined in the "The Components" section.

A user's "pain pattern" is the record of the user's responses in the Databases. In most embodiments using an individual database (11), all the user's responses should be recorded in the individual database (11) for that user (also called the "user's individual database"). In many embodiments using a centralized integrated database, some or all of the user's responses should also be recorded in the centralized integrated database (10), and they may also be recorded in one or more specialized databases in versions of the invention using specialized databases (33).

The record of any specific response of a user in any of the Databases should not contradict the record of the same response in any of the other Databases. The user's "pain pattern" during one or more specific time periods is the record of the user's responses recorded in the Databases during those time period(s). Some examples are: The user's pain pattern for a physical therapy session is the records of the user's responses during that physical therapy session recorded in the Databases. The user's responses recorded in the Databases during the 3 hours after every one of the physical therapy sessions in a group of physical therapy sessions is the user's pain pattern during a group of lengths of time, where each of the lengths of time is defined as the 3 hours after one of the physical therapy sessions. The record of the user's responses between 6 A.M. and 10 A.M. each day recorded in the Databases is the user's pain pattern between 6 A.M. and 10 A.M. each day. The user's overall pain pattern is the records of the user's responses, recorded in the Databases, over all the time since the user has been using the invention, for all the user's body parts. The user's pain pattern for a length of time for a body part is the records of the user's responses, recorded in the Databases, regarding pain or lack of pain for that body part, for that length of time. A user can have a pain pattern for a body part for any length of time for which a user can have an "overall" pain pattern for the user's entire body. Herein, when a user's "pain pattern" is discussed, it can be the pain pattern for a specific body part(s) or the pain pattern for all the user's body parts, unless which one is meant is evident from the context.

A user "expresses" information, whenever the user registers a response or does not register a response on an input device that the user has acknowledged that he/she is using, in a way that the centralized program (45) would receive the acknowledgment. Generally, the user would acknowledge that he/she is using the input device by inputting the user's user ID, and perhaps other information for security. into the input device. The user could acknowledge that he/she is using the input device by using any of the other methods known in the prior art. The input device would generally then transmit the fact that the user is using the input device to the centralized program (45). A user could also show that he/she is no longer using the input device using any of the methods known in the prior art, including, but not limited to, the user inputting the user's user ID and other information again or another user inputting their user ID and other information into the input device, wherein the invention's components that directly or indirectly accept transmissions could automatically conclude that the first user is no longer using the input device.

When the user registers a respnse on an input device, the user is expressing the information in the response on that input device. When a user is not registering a response on any input device, the user is still expressing information-The user is expressing that he is not feeling pain in those body part(s) wherein the user can an input device to indicate that the user is feeling pain. On a pain scale where "0" indicates "no pain", the user is expressing a pain level of 0, in those body parts.

A "body part" is a part of a human body, including a part of a human body that comprises other body parts. A group of body parts can also be considered a body part.

A "caregiver" is a person responsible for caring for a user of the invention. Parents can be "caregivers" for their children, for example. A home health nurse would also be a "caregiver" for his/her patients. Healthcare providers can also simultaneously be caregivers.

A "user" is an individual who uses any embodiment of the invention to make responses when the user feels pain.

A "researcher" is a person who uses the invention to learn something. A caregiver, user, healthcare provider, or another person can also be a researcher.

The term "input device" means any instrument which includes as among its parts one or more pain indicator units, and/or a pain indicator skin, and/or includes pain indicator virtual units (To be discussed below). For example, a user's cellular phone with an app including pain indicator virtual units is an input device. A part model with one or more pain indicator buttons is an input device. A pain indicator piece (32) is not an input device, because the pain indicator unit(s) and/or pain indicator skins attached to the pain indicator piece are not parts of the pain indicator piece; They were attached onto the pain indicator piece. The pain indicator unit(s) and/or pain indicator skins attached to a pain indicator piece are input devices.

Every method of identifying which pain indicator unit(s), part(s) of pain indicator skin(s), or virtual pain indicator unit(s), has been activated, and which body parts that pain indicator unit(s), part(s) of pain indicator skin(s), or virtual pain indicator unit(s) indicates pain in, when activated, is explicitly included within the present invention.

A pain indicator unit, pain indicator skin or pain indicator virtual unit is "activated", when a user registers a response on the pain indicator unit, pain indicator skin or pain indicator virtual unit. For example, when a user presses a pain indicator unit that is a button, and registers a response, the user has "activated" the pain indicator unit. A user can activate the same pain indicator unit, pain indicator skin or pain indicator virtual unit multiple times.

The "pain line" is defined herein as the line made by connecting, on a line graph with time as the X axis, and as an axis in another dimension, such as the Y axis, a user's reported pain levels, on a pain scale, in the same body part, in different points in time. For example, if the user reports a pain level of 1 in his right arm during the first hour, 2 in the second hour, 3 in the third hour, 1 in the fourth hour, and 0 in the $5^{th}$ hour, then, on a line graph of the pain the user felt in his right arm, the points 1 hour, 1, 2 hours, 2, 3 hours, 3, 4 hour, 1, and 5 hours, 0 are connected to make a pain line. Note that a user might have different pain lines depending on the body part (the user might have had different pain levels in his left arm than his right, for example, which would lead to different pain lines for the user's left and right arms) and the time periods (Graphing the pain in the same body part reported for each day might yield a different pain line than that yielded by a graph of the pain in that body part for each hour). A user might have a different pain line for a subpart of a body part, and for the whole body part. For example, a user might have different pain lines for a single finger and for the hand the finger is on.

The "area under the pain line" on a graph is defined herein as the area between the pain line and the graph's X axis in a certain range of X on the graph. The "area under the pain line" for a specific defined time period, can be calculated, and/or the "area under the pain line" for the entire period for which the user has expressed information, up to the present, can be calculated.

The pain line's "slope" on a graph is the pain line's rate of change over a period of time. For example, if the user reports a pain level of 2 in a body part at the first hour's beginning, 3 in the same body part at the second hour's beginning, and 4 in the same body part at the third hour's beginning, the pain line has a slope of 1 per hour during the two hours between the first hour's beginning and the third hour's beginning.

Medical and dental personnel would generally want to reduce the areas under a user's pain lines, because this means the amount of pain the user feels in different body parts over time would be reduced. When a user has different pain lines representing different areas of his/her body, medical and dental personnel would want to reduce the combined area under all the user's pain lines, which means that the total amount of pain the user feels over time is reduced.

Likewise, a user's "pain surface" is a surface formed on a graph showing the user's pain lines for multiple parts of the user's body, with each pain line covering the same time period. Two pain lines will be edges of a pain surface. X represents time, and each other dimension in the graph represents the user's pain level in a certain body part. A graph including the user's pain lines in two body parts with x representing time is therefore a 3-dimensional graph, with a line in the x and y dimensions, and a line in the x and z dimensions. The two pain lines are the pain lines for the user's two body parts. The "pain surface" is the surface created by connecting the pain lines' points at each point in time. For example, if at time $x_1$, pain line 1 passes through the point $x_1$, $y_1$, and pain line 2 passes through the point $x_1$, $z_1$, and at time $x_2$, pain line 1 passes through the point $x_2$, $y_2$, and pain line 2 passes through the point $x_2$, $z_2$, the pain surface includes the area bounded by $x_1$, $y_1$, and $x_2$, $y_2$, and $x_1$, $z_1$, and $x_2$, $z_2$.

Using computers, we can examine information about a theoretical graph with more than three dimensions, without visually representing the graph. For example, we can examine information about pain surfaces the relationships between pain lines create, in a "graph" with more than three dimensions, where each dimension is the user's pain level in a certain body part.

A "pain shape" is the shape bounded by multiple pain surfaces touching, where each pain surface is created by connecting the points, representing pain level in different body parts at the same time, in a user's pain lines on a graph. The pain shape's volume is the volume inside touching pain surfaces, A pain shape can exist in more than 3 dimensions, representing more than 3 body parts, and, a pain shape with more than 3 dimensions does not need to be drawn but can be analyzed by computers as a mathematical construct. If a pain shape has more than 3 dimensions, the extent of the space inside the pain shape, as measured in the form (no. units) to the power of (no, pain shape's dimensions), is still called "volume". Thus, the volume of a three-dimensional pain shape is expressed in $(units)^3$ and the volume of a four-dimensional pain shape is expressed in $(units)^4$. Medical and dental professionals would want to reduce the volumes of the pain shapes of the patients they are treating, all other things being equal.

A user ID is a unique identifier for a user. User IDs can take many forms, such as a fingerprint, footprint, alphanumeric code, picture of the user, recognition of the user's face (facial recognition technology) or any other type of ID present in the prior art.

A device ID is a unique identifier for an input device.

"Environmental Information", for this application's purposes, is information about the environment physically external to the user, such as information about temperature, air pressure, AQI (Air quality index), and precipitation, in the user's location. A service that monitors environmental information is called an "Environmental Monitor" for this application's purposes. For example, http://www.weather.com is one example of an environmental monitor. Some embodiments of the invention will include the ability for the centralized receiving module to capture environmental information from one or more environmental monitors and recorded in the centralized integrated database (10). The environmental information can also be recorded in individual databases relating to users who are physically close to the location where the device sensing the environmental information is located, and/or recorded in one or more specialized databases. Examples of environmental information are temperature, air pressure, relative humidity, absolute humidity, specific humidity, air quality index (AQI), levels of sulfur dioxide, levels of nitrogen dioxide, levels of other pollutants, atmospheric oxygen level, atmospheric carbon dioxide level, and other environmental quantities that can be measured.

A single variable that is part of "environmental information" is an "environmental variable". Absolute humidity level is an example of an environmental variable.

In most embodiments, if information about an environmental variable's level at a certain time and place is unavailable (for example, because the sensors that sense the environmental variable's level in that place were unavailable) then the invention will not consider that environmental variable's level in that time and place when doing statistical analysis.

In general, when an environmental information data point is saved in one of the Databases, the location and time, from which that environmental information data point was gathered, should also be saved in that Database, if possible. This makes many embodiments of the invention more effective. In most cases, environmental monitors will broadcast the location and time of each data point they gather, so this information can also be received by the components responsible for saving information in each Database, and the components can also save the location and time information in each Database.

Likewise, in general, when individual information is saved in one of the Databases, the location and time from which that individual information is gathered should also be saved in that Database, if possible. Most input devices can be designed to broadcast the time and location of individual information that they receive, so the individual information can also be received by the components responsible for saving information in each Database, and the components can also save the location and time information in each Database.

A response coming from a pain indicator unit, pain indicator virtual unit, or part(s) of pain indicator skin(s) that indicates the pain the user is feeling in a more specific body part (For example, one of the right fingers vs. an entire right arm and hand that includes the right fingers) shall herein be called "more specific" than a response that comes from a pain indicator unit, pain indicator virtual unit, or part(s) of pain indicator skin(s) that indicates the pain the user is feeling in a group of body parts that includes that specific body part. For example, a response that indicates pain in the user's forearm is more specific than a response that indicates pain in the user's arm.

"Pain indicator units" are further explained in the "components" section. A pain indicator unit in the form of a button may be called simply a "pain indicator button" herein.

An input device's "exactness" is defined herein as a measure of how much the responses that the input device is capable of registering can indicate pain in a specific body part, as opposed to a more general area of the body that includes that specific body part. For example, an input device with separate pain indicator units for the right arm, right hand, and each of the right fingers is more exact than an input device with one pain indicator unit that the user must press to indicate pain in the right arm, right hand, and each of the right fingers. If two input devices have pain indicator skins, and the pain indicator skin on one of these input devices is capable of detecting touch in a more localized area, then responses registered on that input device are considered "more exact" than responses registered on the other input device. An input device's exactness is based on the input device's capabilities, while a response's specificity is based on the body parts where the user is showing pain when the user registers the response (The more specific the body part(s) the more specific the response). A user can theoretically make a response, on an input device, that is less specific than the input device is able to register.

Pain indicator units and input devices are further explained in the "components" section.

"Response data" is one or more users' responses that can be, or have been, recorded in one of the Databases.

A "nominating rule" is a rule a researcher selects, where the rule picks which of a) The pain levels, or b) A function of the pain levels, that a user has expressed in responses, for a body part, during a type of time period the researcher specifies (The nominating period). The pain level or function picked using the nominating rule is focused on for data analysis purposes. Examples of nominating rules are a nominating rule to pick the highest pain level the user registered in the user's chest during each 24-hour period (When the nominating period is 24 hours), or to pick the average of the pain levels in the user's chest the user expressed in the registered responses, on the occasions when the user registered a pain level in his chest, during each 24-hour period (When the nominating period is 24 hours). In these two examples, the "nominated" pain levels is the highest pain level expressed in each 24-hour period, and the average pain level in the user's registered responses during each 24-hour period, respectively.

Researchers might also wish to use a nominating rule, nominating periods, and nominated pain levels for data analysis purposes because this might help them to detect users' health conditions, including latent health conditions. For example, use of a long nominating period, like one year, might help the researchers to detect some health conditions.

Ideally all responses users register would be recorded in the centralized integrated database (10) (explained under "components"), and/or other databases, so it is very possible that a user will register multiple responses with multiple pain levels, in the same body part, during a nominating period. For example, if the user registers pain levels 1,2,1, 1, and 5, in the same body part, at different times during a nominating period of 1 hour, and a researcher's nominating rule is to take the highest pain level the user registered during the nominating period, the researcher takes the pain level of 5 for data analysis purposes.

A "nominating period" is the specified type of time period wherein the researcher applies the nominating rule to pick which pain level the researcher wants to focus on, for data analysis. For example, a nominating period could be 1 hour, with a nominating rule to pick the average pain level the user registered, during the nominating period (each hour), in a certain body part.

The "nominated pain level" is the pain level, for a body part, a user expressed, that is selected by applying the nominating rule to the nominating period. For example, if a researcher's nominating rule, is to select the response that the user made, expressing the highest pain level, during a nominating period of 1 minute, in the user's stomach, the nominated pain level for each minute is the highest pain level that the user expressed, in the user's stomach, for each minute. A registered response, that included the nominated pain level, is a "nominated" registered response.

Researchers might wish to use a nominating rule, nominating periods, and nominated pain levels for data analysis purposes because a user might not be activating a pain indicator unit, that shows that the user is experiencing pain in a body part, for the entirety of the time that the user is feeling pain in that body part. The user might register the response for a time, and then do other things, if the pain does not go away.

Researchers can use different nominating rules, and nominating periods, to examine the same response data and possibly discover insights. The selection of a nominating rule or nominating period should not affect the underlying response data. In principle, a researcher team could study the same response data using two different nominating rules, and see which nominating rule produces the most effective results. Some potential nominating rules for the user's pain in a body part, during a nominating period, are to pick A) The highest pain level in the user's registered responses for that body part during the nominating period, or B) The mean pain level in the user's registered responses for that body part during the nominating period, or C) The median pain level in the user's registered responses for that body part during the nominating period, or D) The mode pain level in the user's registered responses for that body part during the nominating period. Another potential nominating rule is to use every registered response during the nominating period. Other potential nominating rules are possible. In most embodiments of the invention, the researchers can apply a nominating rule and nominating period to the response data they are using, during or after extracting the data from the databases where it is stored, without changing the response data in those databases.

"Location information", for this application's purposes, is information about the geographic positions of things and people, such as the global positioning system (GPS) position of a user when the user registers a response.

"Individual Information" is information about an individual user that is not a response, not location information or environmental information, and is saved in one or more of the Databases. The individual user's gender, age, and race are examples of individual information. Virtually any other kind of information about an individual, that is saved in one of the Databases, can be individual information, In some embodiments, information about the user's health conditions, and age, may be forms of individual information included in Databases. In some embodiments, a user may import individual information such as events, from another program such as a calendar-type app like Google Calendar into one of the Databases, to be saved in one or more of the Databases in conjunction with the user's User ID and the times that the events happened.

A "health condition" is when a user's health is suboptimal in some way. Some health conditions include broken bones, bacterial disease, viral disease, diabetes, dental cavities, blocked veins or arteries, potential strokes, aneurysms, appendicitis, and internal bleeding.

A "visual signal" is any light made or flashed by an alarm light for the purpose of making others aware of the pain that a user is feeling.

The "time division" is a discrete kind of time period chosen with the time division indicator (explained later). Examples of time divisions are 1 second, 1 minute, 1 hour, and 1 24-hour day. As many other examples are possible as discrete types of periods of time exist.

The "timestretch" is each individual period encompassing the time division the user selected using the time division indicator or time division indicator function. For example, if the user selected 1 minute as the time division, each minute is a timestretch.

A "threshold" for this application's purposes is a defined level, set by a user, viewer, or researcher, for a designated quantity. Some embodiments of the invention may be programmed to take certain actions when the designated quantity reaches a level higher and/or lower than the threshold. For example, components of a user's remote program (20) may be programmed to send an alarm signal to a user when that user's average nominated pain level in the user's chest during a 1-week period is 2 higher, on a pain scale from 1-10, than that user's average nominated pain level during the previous week. The "2 higher" is the threshold the user set. In some embodiments, the user can set a threshold for the user's remote program (20) to give the user an alarm signal if the user's pain pattern for the user's chest which, based on past studies of pain patterns for users' chests, is correlated with a specific chance of a heart attack within the next 24 hours (Such as 0.8%). Then, if the user's pain pattern in the user's chest, or part of the user's chest, is a type of pain pattern that is correlated with a 0.5% chance of a heart attack within 24 hours, and this pain pattern changes to a type of pain pattern correlated with a 0.9% chance of a heart attack within 24 hours, the user's remote program (20) will give the user an alarm signal. The designated quantity, in this case, is the percentage chance that the user will experience a heart attack within 24 hours.

The designated quantity may be of any form that the invention can measure, including, but not limited to, relations between other quantities, such as the slope of a user's pain line for a body part, the area under a user's pain line, for a body part, within a certain time period, a user population's average pain level in a body part during a time period, a single user's median pain level during a group of nominating periods, and other designated quantities.

An "alarm signal" is any kind of signal that can function as an alarm. The sounds the alarm (14) makes or the light the alarm light (3) creates are examples of alarm signals.

A "viewer" is a person who views the screen of a display section (2) or human body display (12) and can operate the display section (2) or human body display (12). Viewers can also be healthcare providers.

A "registered event" is information, that is part of a user's individual information, and is recorded in the user's individual database (11) and the centralized integrated database (10) after the user establishes the user's account and creates the user's individual database.

"Display data" shall herein refer to visual representations a display section (2) or human body display (12) creates, and shows on its screen, and that are based on data from individual users or user groups that the display section (2) or human body display (12) has analyzed. "Display data" is distinguished from "backdrop data", which is information and images that would appear on the display section (2) or human body display (12)'s screen regardless of the specific information in the display data. Backdrop data might label the display data; A user category name, or an equation defining a user category, are examples of backdrop data while the average nominated pain level the user category experienced is display data. An outline of a human body on a human body display (12) is an example of backdrop data, while the colors, numbers, and other information on the human body display that are based specifically on the pain the source users felt are display data.

A "sub-period" is a smaller time period that is part of a larger time period.

NEED FOR THE INVENTION

A patient who visits the dentist may experience pain while in the dentist's chair, or during a dental procedure, when the patient's pain or discomfort has gradually or suddenly increased. The patient might want the dental personnel to "Stop a little bit", but have no effective way to signal to the dental personnel who might be performing a cleaning or other procedure on the patient.

If the dental personnel know that the patient is experiencing pain, they might choose to take a "break" and stop working on the patient for a time, and to also give the patient a break, which may relieve the patient's pain. The dental personnel might also change their procedure, to stop doing whatever is causing the patient's pain. The patient will then need a way to communicate whether his or her pain has gone away. The patient should also preferably have a way to communicate which part of the patient's mouth is the patient's pain's source, so that the dental personnel know how to change their procedure. The patient might not be able to simply tell this information to the dental personnel if the patient has dental instruments in his/her mouth.

There is a need for an invention that allows a user to quickly communicate that the user is experiencing pain to a healthcare provider treating the user. The invention should also keep track of how much pain the user experienced, and this pain's type and location, and compare the pain amount that user experienced to the pain amount other users experienced, to see if information about users' health can be discerned from the results, or if the results might show ways that users can improve their health, or ways that improvements of other kinds, such as improvements in surgical techniques, can be made in the future. The invention should be precise, and should be more precise than users simply verbally reporting their pain. The invention should also keep records of the pain that users report, and make the records easy for authorized personnel to access (meaning that the person being granted access can access the information in the records, but cannot modify it.) so that insights can be discerned from the records. The invention should also be able to store and examine a very large number of records, which will allow more insights to be derived about users with rare conditions. The invention should also be capable of creating graphs and other data visualizations related to the pain users have experienced.

An orthodontist's patient might also experience pain while in situations where he/she cannot talk, and may need to quickly signal to the orthodontist that he/she is experiencing pain. Likewise, patients in physicians' offices and emergency rooms might also experience pain of discomfort and need to signal to medical personnel quickly. Patients experiencing medical procedures, or in hospital beds, might also experience pain because of anesthesia not working properly, or for other reasons. Such patients will need to signal to the medical or dental personnel nearby that they are experiencing pain, so that the medical or dental personnel can help the patients.

Nonverbal patients might be unable to communicate when they experience pain. For example, stroke victims, and patients who are nonverbal because of age-related illness, might be unable to communicate with caregivers when they experience pain, and so the caregivers will not know that the patients need help. Small children might also be unable to communicate how much, and where, they are experiencing pain, and that they might need help. The present invention helps to eliminate or reduce these problems, and the similar problems, discussed above, that medical and dental patients experience. The present invention should be available to anyone, but particularly applicable to medical and dental patients.

Some patients might also be unable to indicate the degree, type, and/or location of pain which they are feeling because of language barriers; For example, they might not speak the same language as the dentists or physicians treating them, or might not speak it well enough. Mphahlele et. al. also noted in a study that some terms may not translate exactly between languages, even when a questionnaire is translated between languages.

Some patients might also fail to communicate the amount of pain they are feeling because of cultural reasons; Members of some cultures might be trained not to talk about pain, or trained to maintain a "stiff upper lip", or alternatively to complain loudly, which might exaggerate the amount of pain they feel. The invention disclosed herein can help these patients, because they can use it to communicate that they are feeling pain more accurately than they might be able to communicate this otherwise.

Reason exists to believe that gender bias influences some physicians' and dentists' perception of a patient's pain depending on the patient's gender and/or physician's gender. In some cases, available information about the pain patients experience might be more limited for patients of one gender than for patients of another gender. For example, previous studies of some conditions have involved primarily male subjects, which means there is comparatively little information about female subjects' experiences. Other kinds of pain, such as pain related to periods, can only be experienced by one gender but not another, for physical reasons, and so people who are not members of the gender that experiences these kinds of pain may not know what these kinds of pain are like, or the best ways to reduce them. The present invention will hopefully reduce or correct the problems created by such gender disparities and/or gender bias.

Parents and other caregivers can also use variations of the invention to learn when a person for whom they are giving care (Such as a child who is sick at home) is experiencing pain, or experiencing increased pain, while the caregiver is far away from the child, through the invention's feature of communicating information to an "app" which can be used on a user's cellular phone.

Students can use the invention to help understand and reduce any pain they might be feeling, and so focus on academic work better, because they are less distracted by pain. One inventor herein is a Professor Emeritus at Pasadena City College in Pasadena, CA, and the inventors believe that reducing pain experienced by students may help student retention and success at academic institutions, by helping the students to focus better when they experience less pain.

The invention can also be used to help physical therapy patients in many ways. For example, a user can do physical therapy, and during the therapy, activate pain indicator units on a human body model (defined below) to indicate when and where the user is feeling pain. The time(s), type(s), intensity(s), and location(s), of the pain the user experiences, that the user expresses by activating the pain indicator units (discussed below) on the human body model, will be transmitted by a transmitter located on the human body model to a remote program located elsewhere. The information the remote program receives about the time(s), type(s), intensity(s), and location(s) of the pain the user experienced, is then saved as data in an individual database for that user. The centralized calculation module (discussed below) then performs calculations on that data. The invention makes available to the physical therapist the calculations' results and information about these results. The physical therapist can then examine, and draw conclusions from, the data and results, by relating the data and results to what the user did, and what was done to the user, during the physical therapy session. For example, if the user experienced more pain during certain activities, the physical therapist might decide that the user should perform different activities during the next session.

This system is more precise than having the user verbally report where, and how much, pain the user experiences. The system will also be helpful to compare information such as the average pain amount that the user experiences in different periods of time. This system will also make it easier for the physical therapist and user to compare the pain the user experiences on different occasions.

Not all of the invention's components that may be involved in the above scenario are listed in the discussion of the scenario; The above scenario is just an example and the invention's components, and their interactions, are more thoroughly described below. The user also does not need to use a human body model; The pain indicator units the user activated can be located on any of the components that include pain indicator unit(s), and/or pain indicator virtual unit(s), and/or a pain indicator skin, and are described below. The human body model in the above scenario was an example.

The invention can also be used to combine information from multiple physical therapy sessions. In the scenario above, the information about the time(s), type(s), intensity(s), and location(s) of the pain the user experienced in each of multiple sessions is then saved as data in that user's individual database. The centralized calculation module then performs calculations on that data. The invention makes the calculations' results and information about these results available to the physical therapist. The physical therapist can then examine, and draw conclusions from, the data and results, and possibly notice trends that happened over multiple sessions. These conclusions might be stronger than if the physical therapist only had data from one session to work with. For example, if the pain the user experienced during certain activities decreased, over several sessions, the physical therapist might decide that the activities the user is performing are succeeding and recommend that the user perform more of the same activities.

If the locations and intensity of the pain the user experiences in one session are substantially different from the locations and intensity of the pain the user experienced in different sessions, this may alert the physical therapist to examine the user more closely and draw conclusions about how the user's physical or mental state may have changed.

The invention also eliminates or reduces the problem that, in the above scenario, the user might not have the same physical therapist for every session and this issue might affect the physical therapists' ability to gain and use information about pain the user feels, and other aspects of the user's health. The way the user interacts with the physical therapist, the information the user gives the physical therapist, and the way the physical therapist interprets and records the information might be different from one physical therapist to another, which will affect the amount and accuracy of the information that the user's physical therapists have. One physical therapist also might not have access to another physical therapist's notes. All this affects the physical therapists' ability to help the user. This is true of other healthcare providers, in that one healthcare provider might not have all the same information about a user as a different healthcare provider of the same type, which might decrease one or both healthcare providers' ability to help the user. The present invention allows the user to record his own experiences with pain, himself, in a single format that is the same all the time.

The invention can also be used to learn about a user's experiences after the user finishes therapy sessions, in a similar way. When the user experiences pain after the user has done a physical therapy session, the user can activate pain indicator units on a human body model, or activate the pain indicator units on any other component(s) listed as including pain indicator unit(s), and/or virtual pain indicator unit(s), and/or a pain indicator skin below. The user can do this if the user feels pain at any time after he/she has finished the physical therapy session and the user does not need to press the pain indicator units at a specific time. Then the time, location, and intensity of the pain the user experiences is recorded in the individual database pertaining to that user. The physical therapist can later examine the records of the pain that the user experienced, and draw conclusions. The user can record the time, location, and intensity of pain the user experiences after multiple physical therapy sessions, and this information is entered into the individual database relating to that user. The physical therapist can also examine this information. For example, if the user always experienced pain in his or her arms 6 hours after using a certain physical therapy technique, perhaps the physical therapist should not use that physical therapy technique with that user. On the other hand, if the user experiences pain in his/her arms 6 hours after trying the technique in the first session, 7 hours after trying the technique in the second session, 8 hours after the third, etc., the physical therapist might draw different conclusions about whether the physical therapy technique is effective with that user.

In some versions, the pattern of the locations, intensity, and time of pain that the user experienced may be compared to the pattern of the locations, intensity, and time of pain that other users in similar circumstances experienced. Physical therapists or other healthcare providers can compare the patterns and draw conclusions. One such conclusion might be to investigate further if the user experiences much more intense pain than other users in similar circumstances.

In theory, if granted access to the information, the physical therapist can compare the pain pattern the user experienced, to the pain patterns a large group of other users experienced, or the pain patterns all users experienced. In this example, a specialized database can also be used to compare the pain pattern the user experienced to the pain patterns experienced by users in similar situations, such as users undergoing physical therapy.

In theory, a dentist, physician, nurse, or other healthcare provider could, using the "app" (to be discussed later) on the healthcare provider's cellular phone, receive information about the pain patterns, including time(s), type(s), degree(s), type(s) and location(s) of pain that multiple of the healthcare provider's patients are experiencing, as the patients are experiencing that pain, in real time. The app could then perform statistical calculations about the time(s) degree(s), type(s) and location(s) of pain a specific healthcare provider's patients experienced, possibly showing patterns. Therefore, if, for example, a specific dentist notices that several of his patients are experiencing an above-average pain degree on a certain day (Compared to what they were experiencing before) then he may decide to investigate the cause. He might also discover the cause and make recommendations to his patients about steps they should take to relieve their pain or otherwise take care of their health.

The invention can also be useful to study the effects and prevalence of pain, in that, by comparing the time(s), type(s), degree(s), type(s), and location(s), of pain experienced by large numbers of patients in similar situations (For example, patients undergoing or recovering from similar operations), researchers may be able to draw conclusions about the pain patterns that future patients might expect in those situations, and how to reduce the pain degree, and its type(s) and location(s), that patients experience in similar situations. For example, techniques for operating, or for recovery management, might be changed.

Researchers may also be able to draw conclusions about how the pain some patients experience might be reduced by examining patterns of the time(s), degree(s), type(s), and location(s) other patients of similar age, gender, ethnicity, etc. experience. This has the additional benefit of being cheaper and sometimes faster than organized clinical studies of pain. Instead of creating a clinical study and paying various entities for participation, researchers could simply examine the body of data that already exists, created by the invention, about the time(s), degree(s), type(s), and location(s) of pain patients of similar age, gender, ethnicity, etc. experienced.

By examining the time(s), degree(s), type(s), and location(s) of pain the same person experienced on different occasions, researchers and/or healthcare providers might also be able to recommend a course of treatment for that person, when that person experiences a medical or dental condition, that is more optimal for that specific person but differs from the courses of treatment normally used for patients that have that medical or dental condition. Researchers, and/or healthcare providers, might also be able to understand pain better, and to diagnose when a certain patient may need a course of treatment that is different from the courses of treatment normally used for patients with similar conditions, by comparing the time(s), degree(s), type(s), and location(s) of pain the patient experienced on certain occasions to the time(s), degree(s), type(s), and location(s) of pain other people experienced on similar occasions, because the particular patient is more sensitive to pain in certain areas than most other patients, or for other reasons.

Medical or dental personnel, or other healthcare providers, might also use the invention to discover when something is wrong with a specific user, and to try to find the user's condition's source, and/or alleviate the pain that user faces, by statistically comparing the user's pain pattern on a particular occasion to the user's pain patterns on other occasions, and to note whether the user's pain pattern differs substantially on the most recent occasion from that user's pain patterns in the past. An example is comparing the user's pain pattern after a 2-hour run to his/her pain patterns after past 2-hour runs. Medical and/or dental personnel might also statistically compare the user's pain patterns, and times, degree(s), type(s), and location(s) of pain, either on multiple occasions or on a particular occasion, to other people on similar occasions' pain patterns, and times, degree(s), type(s), and location(s) of pain. An example is comparing the user's pain pattern after a 2-hour run to other users' pain patterns after 2-hour runs.

The invention can also be useful for treating chronic pain. A person suffering chronic pain can record the time(s), location(s), type(s) and intensity(s) of their pain when they feel pain, and the system will note this information. Then the patient or her healthcare providers can review whether the patient's pain pattern changed when specific events happened. These events might include changing the patient's routine, or taking a new medication, or numerous other things. For example, if a chronic pain sufferer takes a new medication and then the number of times per day that the chronic pain sufferer experiences pain decreases by 10% with a 30% decrease in average reported pain level, this might indicate that the chronic pain suffer should keep using that medication. A 10% decrease in number of experiences of pain per day with a 30% decrease in reported pain level might also not be evident to the chronic pain sufferer or his/her doctor if they only rely on verbal reporting and the chronic pain sufferer's memory.

The invention can also be useful in tracking the effects of "Long COVID", which is one of the recent COVID-19 pandemic's symptoms. Long COVID sufferers might experience more pain, in different areas of their bodies, than they did before they contracted COVID-19. Researchers and healthcare providers might be able to learn more about Long COVID, and hopefully about how to relieve or mitigate Long COVID's symptoms, by examining groups of Long COVID sufferers' pain patterns and using them to draw conclusions. Researchers might also learn additional information from the pain patterns of groups of Long COVID sufferers.

The invention can also potentially be used to reduce the harm caused by other diseases of which substantial pain is a symptom, and also to discover better ways of treating those diseases. If the invention is used to compare the two pain patterns of two sufferers of the same disease, where the area under the first user's pain line is substantially less than the area under the second user's pain line, it may be useful to analyze why the differences exist and see if they can be duplicated so that other users with the same condition have less pain, or have relief from other symptoms. This might be possible for users with amyotrophic lateral sclerosis, for example.

In general, the invention can be used to help people with health conditions that cause or increase pain levels to avoid or reduce depression by helping them to reduce their pain levels, which will help them to avoid or reduce depression. This should help people with health conditions to recover better from those health conditions, or manage them better.

The invention can also theoretically be used to monitor the effectiveness of pain-relieving medication. For example, if a user is suffering from pain, the user will indicate this by using an input device. For example, the user can activate pain indicator units on an input device. The user can then take Tylenol, and continue activating pain indicator units on the input device as the pain hopefully becomes less intense. Insights can be drawn about effectiveness of Tylenol to that user from the decrease in the pain the user is feeling. For example, after the user takes the Tylenol, the user's pain may decrease more or less than average, for users with pain in the same location. The user's pain may also decrease faster or slower than average. This information is recorded, if the user continues to activate the pain indicator units on the input device to indicate his/her pain level. Then the user, and the user's healthcare providers, may be able to draw insights from this information.

The invention can also be used to show when a user should be worried about an insect bite, sting, or other injury caused by an animal or other organism. Many people are stung or bitten by bees or other insects, and this causes pain but no permanent damage. However, if a user is bitten or stung and experiences pain, or a pain pattern, that is much more severe than is normally expected, from the bite or sting, this could indicate some larger problem such as an infected bite, and therefore show that the user should seek medical attention. The same is true of other injuries that seem to be minor. The present invention will help detect pain patterns, resulting from minor injuries, that are abnormal enough that the user experiencing the pain pattern should get expert help.

The invention can also help early cancer detection in the following way: If a user experiences an unusual pain pattern, the pain pattern may be caused by a tumor or other cancerous or precancerous condition. With enough study, it may be possible to find pain patterns associated with cancer, tooth abscesses, or other specific, undiagnosed, medical or dental conditions. The invention herein might send an "alert" to a user if the user reports a pain pattern that has been found to be associated with a specific type of cancer or another adverse health condition. The "alert" might tell the user to visit a physician, dentist, or other healthcare provider for an examination, to see if the user has the health condition the alert is warning about. Note that in some embodiments the "alert" does not need to be sent only when a pain pattern is associated with a greater than 50% chance of cancer; In those embodiments the "alert" can be sent when the pain pattern is associated with a lower probability, like 10% or 1%.

The invention can also be used to track users' "low-level" pain and hopefully assist in finding whether this pain has identifiable sources. For example, some people may experience unexplained low-level aches and pains, and by tracking these pains more accurately, researchers may be able to find sources for these pains in the users' environments, or the users' lifestyles. The inventors are informed that a low percentage of the population experience pain when smartphones are used near them. The inventors do not know if this is true, but perhaps the matter should be examined further. The present invention can be used to examine this matter further.

The invention can theoretically be used to track users' experience of other sensations, such as itchiness. The invention can be used to learn information about when a specific person is experiencing itchiness, or when a group of people tend to experience itchiness, in a similar fashion to the way that the invention can be used to learn when a specific person, or group of people, experience pain, as discussed above.

Various examples of users sharing their data with others are discussed herein. In every case, the data may be protected by security features of every kind known in the prior art, to make sure that the data is only shared with authorized people.

DISCUSSION OF THE PRIOR ART

Zuckerman-Stark, et. al.'s, U.S. Pat. No. 11,259,708 created a method of pain classification and pain monitoring, but that method differs a lot from the present invention. Among other reasons, there is nothing in Zuckerman-Stark similar to the current invention's capability for the user to unequivocally voluntarily show that he/she is experiencing pain. Instead, Zuckerman-Stark's invention relies on indirect signs that the user is experiencing pain.

Zeller, et. al.'s, U.S. Pat. No. 11,241,191 discloses a series of systems for detecting, monitoring, and evaluating pain, but those systems are substantially different from the systems in the present invention, for example, nothing similar to the present invention's mouth models, human body models, or part models is disclosed in Zeller. Zeller does discuss body-maps, but these are different from anything in the present invention. Zeller's body-maps seem to be projections on the actual body of a patient, combined with a processor that interprets the images of these projections on the patient. The present invention's mouth models, human body models, and part models, however, are models of human body parts or of a whole human body, with pain indicator units or pain indicator skins which a user can activate to indicate when and where he/she is feeling pain.

Boggs II, et. al.'s, U.S. Pat. No. 11,235,146 discloses a method for treating pain, but Boggs does not disclose any of the features or methods for announcing pain's presence, that are parts of the present invention.

Donovan, et. al.'s U.S. Pat. No. 11,207,100 discusses methods of treating back pain, but Donovan's proposed pain treatment methods focus on detecting chemicals that are emitted when a patient experiences pain. Again, this is different from the present invention, which focuses on self-reporting of pain, and includes models of different body parts which a patient can use to further specify where he or she is experiencing pain.

Osorio's U.S. Pat. No. 11,173,245 discloses a method of automatically treating pain once the pain has been detected, but Osorio's invention differs from the current invention because Osorio relies on physiological signals to determine when a patient is experiencing pain, while the present invention relies on patients voluntarily reporting when they are experiencing pain. Osorio's invention also has nothing similar to the present invention's body part models.

Pulliam et. al.'s U.S. Pat. No. 11,123,562 discusses a pain quantification system, but it relies on observing various activities by the user and reporting the user's pain by analyzing signs the user is experiencing during these activities. Pulliam's patent is different from the present invention, because, among other reasons, the present invention relies on users to self-report the location, type, and pain degree they are feeling.

Moffitt, et. al.'s U.S. Pat. No. 11,110,276 describes a system for using the biosignals a patient creates to detect pain's presence, but the biosignals in Moffitt's invention are brain waves and other signals the patient involuntarily creates, which is different from the present invention, where the patient voluntarily and deliberately creates the indications that the user is experiencing pain.

Mason's U.S. Pat. No. 11,107,591 discusses a system for optimizing treatment plans, but the only time investigating a patient's pain level is discussed in Mason's patent is in the context of having a patient indicate a pain level on a patient interface, which appears to be a computer such as a desktop or laptop, and is different from the devices in the present invention on which the user indicates the presence of pain.

Mason's U.S. Pat. No. 11,101,028 discusses a system that includes displaying a patient's last reported pain level, but that system is limited to monitoring treatment plans' progress, does not specifically try to analyze differences between a patient's responses and the responses that other patients give in similar circumstances (such as the mean and median pain levels patients in similar circumstances reported) and does not include devices for the patient to indicate when he/she has pain, or a combination of signals and sounds which indicates when the user is experiencing pain, or indicates any related information.

Rossi, et. al.'s U.S. Pat. No. 10,019,430 discusses a system and method for electronically filling out forms. The data that goes into the forms is called "forms data". The pain patterns, and responses, of users, once recorded in the present invention, could be turned into forms data used in Rossi, et. al.'s invention.

Application 20160232416 by Rossi, for the vital data assistant system, includes the ability to transfer a user's medical history information to a medical center through use of a medallion. If the system of Application 20160232416 is used, the pain patterns and responses of users, once recorded in the present invention, could be turned into medical history information discussed in Application 20160232416.

Harbut et. Al's application Ser. No. 15/130,712 discusses systems for pain tracking, but Harbut's systems are significantly different from the systems and methods in the current invention. Harbut does not have the concept of using pain patterns from a large number of users to gain insights about treating disease conditions. Harbut also does not have the concept of aggregating responses from a large number of users by having the responses transmitted over the internet to a centralized server or other computing resource that can place the responses in databases.

Harbut's graphical pain representation is based on different concepts from our representations of pain. Harbut seems to use graphical pain representations to represent types of pain. We use colors to represent amount of pain (or results of statistical calculations based on amount of pain) over time, which Harbut does not do. Our invention is also capable of graphing the pain a user experienced, in more ways than Harbut, which means that additional insights can be derived using our invention that cannot be derived using Harbut's invention.

Harbut does not utilize the concept of using a color to represent a mean or medium level of pain experienced by one person or multiple people over a period of time, or the concept of averaging a user's responses to calculate a mean or median pain level. Harbut also does not use the concept of representing a mean or median pain level intermediate between two other pain levels on a pain scale (For example, 3.8 is intermediate between 3 and 4) by showing a body part with some pixels on a body part in the color associated with the lower of the two levels and other pixels on the body part in the color associated with the upper of the two levels on the pain scale.

Harbut's plan of how to enter "pain entries" is different from our method of entering responses, and that is partly because we are trying to make entry of responses easy for the user, to more easily capture response data as users' pain happens. Harbut's "pain entries" are also different from the responses in our invention. Harbut also does not have an "app" that can be used on a user's cellular phone to enter responses or to monitor others' responses.

Harbut's "draw your pain" idea for entering entries when the user experiences pain is different from our method of entering most responses, because our method depends on users activating pain indicator units, and pain indicator virtual units. The method of entering responses in our invention is also simpler than Harbut's, because we do not cause a user to draw his/her pain before making a response. We try to get immediate information about where the user is feeling pain so we make it easy to make a response.

Publication US20160262691 discloses a method of using indirect signs of pain to detect pain in a pediatric population. However, our present invention includes many features that Publication US20160262691 does not disclose. For example, our present invention includes extensive information about how to use responses either individual users or user populations create to learn about disease's effects, which Publication US20160262691 does not disclose, Publication US20160262691 also relies on pain's indirect effects (such as increased heart rate) to detect pain. Our present invention uses direct reporting of pain by users to detect pain.

Publication WO2020156979A1 discloses, in one embodiment, a "handheld device through which" a dental patient "manually registers his/or pain sensations and/or stress levels (xi) wherein the biopotential information and/or the treatment regimen are displayed on a mobile device, e.g. an iPad." It also says "The processor 122 may be adapted to recommend or otherwise identify one or more treatment regimens 52 for one or more detected stress levels and display said treatment regimens 52 to the clinician 10". However, Publication WO2020156979A1 does not include numerous features of the present invention. For example Publication WO2020156979A1 does not include the ability to communicate whether the patient is experiencing one pain level or a different pain level, and Publication WO2020156979A1 does not include the ability to specify whether the patient is experiencing different pain level in different body parts.

Publication WO2021050972A1 discloses a wearable system for automated and continuous quantification of pain, but WO2021050972A1 relies on sensing pain based on indirect indicators of pain, while our invention relies on users directly reporting pain. Publication WO2021050972A1 also does not allow users to specify where they are feeling pain.

Publication WO2021062358A1 discloses a system for indirectly detecting the amount of pain that a user is feeling based on the user's speech patterns. However, this is different from our invention, which focuses on user directly reporting the amount of pain they are feeling.

Publication WO2020257874A1 discloses a pain assessment method focused on monitoring the facial expressions that the user makes when he/she experiences pain, but that is different from the present invention, which detects pain through the users directly reporting the amount and location of the pain they are feeling.

U.S. patent application Ser. No. 15/656,701 discloses a dental patient pain notification system, but that system does not include many of the current invention's features, such as the ability to record data based on when users in a population experience pain, and the amount of pain they experience, and the ability to do statistical analysis on this data.

U.S. Pat. No. 9,788,917 by Mah discusses methods of using artificial intelligence in automated orthodontic diagnosis and treatment planning. U.S. Pat. No. 9,788,917 does use data sets to create treatment plans, and U.S. Pat. No. 9,788,917 does not consider the pain the user experienced at all, or consider data sets based on the pain experienced by either a single user or a group of users, Publication US20030233053A1 by Woolf et. al. discusses pain assessment systems, but lacks many of the concepts and components this application discusses. Woolf et. al. discuss something called a "pain profile", but their "pain profile" is different from the new concepts discussed in this application. Woolf et. al.'s "pain profile" is a cluster of multiple pain-related symptoms and signs, displaying all the pain-related symptoms a patient reports during an interview and the signs a physical examination elicits. Woolf's method of gathering information for databases, about the pain users experienced, is different from our methods of gathering responses related to users' pain for databases. Woolf et. al. also do not propose any specific device or app that can be used to gather information about the pain experienced by users. Our invention includes such devices and apps.

Publication US20170055915A1 discloses a method and system for detecting users' pain based on biomarkers, which is fundamentally different from the present invention, which detects pain based on users' direct reporting of pain.

Publication US20180085055A1 discloses a system for pain management. Our invention includes many features that their invention does not include. For example, the invention of publication US20180085055A1 does not include the concept of use of the pain patterns from a group of users to suggest a single user's medical conditions. Our input devices also are of different types from those of Publication US20180085055A1.

Publication US20190335999A1 discloses a method for providing medical advice, and an associated device. However, Publication US20190335999A1 does not include many features of the present invention. Publication US20190335999A1 does not include any of our invention's devices for users making responses, such as the mouth model. Publication US20190335999A1 also does not include any attempt to use a database created from the responses of other users to help diagnose a single user.

The correlation between any sign of pain and actual experience of pain is not absolute. We also cannot currently understand the correlation between any type of brain activity, and pain in a specific body part, well enough to make an absolute correlation between that type of brain activity and pain in any specific body part. Perhaps the present invention will help us to establish correlations between brain activity in some brain areas and pain in some body parts, but that is not the invention's main goal.

Booz Allen & Hamilton (BAH) has partnered with the U.S. National Health Institute (NIH) to analyze the cancer-related pain experienced by a set of about 100 cancer patients, by using facial recognition software to analyze videos of the cancer patients for visual cues, which Booz Allen & Hamilton believes are correlated to pain. BAH claims that this is the largest cancer patient pain database presently available.

Our approach is superior to that of Booz Allen & Hamilton for at least the following reasons: First, we are using direct reports from the users themselves about the pain that they feel. There will be no error, or very little error, in the reports of users' pain levels. BAH, by contrast, is using indirect indicators of pain. A patient's facial expressions may be correlated to the person's pain level, but the correlation is not absolute, so BAH's approach will include more error in the reports of users' pain levels. Second, our approach contemplates gradually building a much larger dataset than BAH's approach. Our approach aspires to record responses from all or a large percentage of, users, to gradually build a centralized integrated database of millions of users' responses. BAH's approach, by contrast, seems to rely only on the data from 100 people. With data from more users, our system should be able to make more accurate predictions. Third, our system has the capacity to create sub-datasets of patients with more kinds of cancer than BAH's method, because BAH's method relies on a dataset of only 100 patients. Fourth, our system relies on users making responses when they feel pain, so for example, if a user feels pain at 3 P.M., our system records the pain level the user reports at 3 P.M. Therefore the users are less likely to "misremember" the amount of pain they felt at a specific time. It is not clear whether BAH's system includes keeping records of the pain a patient feels at multiple times during a day, or records a user's pain as a user experiences that pain.

Kristen Sosulski's book "Data Visualization Made Simple" includes the concept that it is possible to discern insights about patterns in data from creating graphs of multiple kinds about the data.

"Ox Educ" created a Youtube series on Bayesian analysis, which is useful for learning about how Bayesian statistical analysis works.

The inventors would like to thank California State University, Los Angeles, (CSULA), University of Miami Herbert Business School, Ave Maria Law School, and New York University Stern School of Business, Queens College, Georgetown (Guyana), University of the West Indies (Jamaica) and State University of New York at Buffalo for what the inventors learned there.

Many embodiments of the invention attempt to measure the intensity of the pain a user experiences. They use a scale, so that users can rate the intensity of their pain on one occasion to the intensity of their pain on a different occasion. A known scale can be adapted and/or modified for this purpose. For example, headache pain intensity can be measured using ratings of average pain in the last 24 hours on a 0-10 numerical rating scale, where 0 on the BPI-SF (Brief Pain Inventory-Short Form) indicates "no pain" and 10 indicates "pain as bad as you can imagine". The BPI-SF is a widely used assessment designed to measure pain intensity and the interference of pain with daily activities and moods. In addition, the BPI-SF has been used in many chronic pain studies, including studies evaluating peripheral nerve stimulation.

The Headache Impact Test (HIT-6) may determine the effect of headache on social functioning, role functioning, vitality, cognitive functioning and psychological distress. The HIT-6 consists of 6 items and is a validated, reliable, and common measure of headache-related disability, including in patients with headache following traumatic head injuries. Change in physical functioning and the impact of pain on activities of daily living (ADL) can be measured using the Pain Disability Index (PDI), a seven-question survey that asks the subject to rate the level of disability they experience related to family/home responsibilities, recreation, social activity, occupation, sexual behavior, self-care, and life-supporting activity on a scale of 0 to 10, where 0 is "no disability" and 10 is "worst disability". The PDI is a simple and rapid tool for evaluating the impact of pain on physical functioning with established reliability and validity.

A scale based on one of these scales can be adapted for use with the current invention; For example, the intensity of the pain the user is presently feeling, that the user indicates when he/she activates one of the pain indicator units, can be on a scale of 0 ("No pain", in which the user would not activate any of the pain indicator units) to 10, which indicates "pain as bad as you can imagine". This scale would have some similarities to the scale used in the BPI-SF, but also some differences. For example, this scale would be applied to all pain instead of only headache pain, and also the user will indicate the amount of pain he/she is feeling at the time when he/she activates the pain indicator unit, not the average amount that the user is feeling over any period.

One difference between the way the BPI-SF is normally used and the way the pain scale will be used in the present invention is that with the present invention the user will be giving information about his/her pain as the pain happens, which allows the user and his/her healthcare providers to document precisely what time(s) of day the pain is happening. The way the BPI-SF is normally used, the user documents the average amount of pain that he/she is feeling over the day's course. The present invention's ability to precisely measure when the user is feeling pain may allow users and their healthcare providers to develop additional insights about the pain.

Another scale can also be used, where the user indicates the severity level of his/her pain ("intensity") using one of multiple levels. The meaning of each level on the pain scale, such as the meaning of "1", the meaning of "2", etc. should preferably be known and/or explained to the user ahead of time.

By examining patients brought into an emergency room's pain patterns, emergency room doctors might be able to diagnose those patients faster by seeing whether a patient's pain pattern is similar to the pain patterns of patients who experienced other specific conditions. Then, the emergency room doctors might conclude, more quickly than they would otherwise, that the patient before them has the same condition(s) as these other patients.

Emergency room doctors might also be able to detect undiagnosed conditions this way, by realizing that something within a user's previous pain patterns that is unrelated to the condition for which the user was brought into the emergency room indicates another condition. An emergency room doctor might also conclude something about the severity of the injuries that a patient who has been brought in is suffering from by comparing the patient's pain pattern in the present to the patient's pain patterns in the past.

An emergency room doctor might also find examining a patient's current pain pattern to be useful because if the patient's current pain pattern indicates that the patient is in greater pain, the patient's condition might be more serious. An emergency room doctor, or a doctor in a "triage" situation, might also use information about different patients' pain patterns to decide who to treat first, or who needs painkillers fastest.

SOME OF THE PRINCIPLES BEHIND THE INVENTION

A few of the principles behind the invention are listed here.

First, the network of nerves throughout the human body might transmit a pain signal when a person is experiencing a suboptimal physical condition. The user might notice this pain, and/or also be able to record this pain as evidence of the suboptimal physical condition.

Second, by analyzing the pain patterns felt by a large number of people, and seeing if there are relationships between the pain patterns those people experienced and the physical conditions those people experienced, the researchers might be able to discover what pain patterns are associated with which physical conditions. They might also be able to find out what pain patterns point to susceptibility to certain physical conditions, or show that a patient is experiencing a certain condition. For example, physicians now know, from interviewing heart attack patients, that pain shooting along a patient's arm is a potential indication of a heart attack. If a patient experiences pain shooting along his/her arm, the patient's attending physician may take this as a sign that the patient is experiencing a heart attack and investigate appropriately.

Third, by capturing information about pain as the pain happens, researchers might be able to discern patterns that they could not discern otherwise. For example, they might find that a large number of patients experiencing a certain physical condition experience pain in their arms at around 5 P.M. The researchers might be able to recommend improvements to the patients' lifestyles based on this.

Fourth, researchers, or the user experiencing the pain might also be able to learn more about the user's health or discern patterns that they could not discern otherwise, by capturing and recording information about pain as the pain happens. For example, if the user records, on a scale of 1 to 10, the amount of pain he is feeling in a certain part of his/her body, and the amount varies, but the user notices that the average of the amounts of pain that he/she feels in that body part in the days of one month is lower than the average in a later month, the user may need to visit a healthcare provider and have that body part examined more closely.

Fifth, patient experiences will generally be improved if healthcare providers who are treating the patients have near-instantaneous information about the pain that the patients are feeling, so the healthcare providers can try to alleviate the pain.

Sixth, capturing information about the users' own perception of the pain they are feeling is more reliable than capturing information about other events that might indicate pain, such as increased heart rate.

Seventh, users may not always notice an increase or decrease in the amount of pain that they feel over a time period. For example, if a user's average reported pain level decreases by 20% from one month to the next, the user might not realize that a 20% decrease has happened, especially if the user's reported pain level each day fluctuated within both months. If, however, the invention is tracking the user's experience of the amount of pain the user is feeling, the user will learn from the invention that a 20% decrease has happened, and will be able to use this information. For example, the user may be able to keep doing whatever new activities the user did during the second month, and see if the 20% decrease versus the first month continues into later months. If it does, the user may have found a way to improve the user's quality of life.

Eighth, some input devices may not be able to register all the information discussed in this application that could theoretically be part of a user's responses. For example, if a mouth model contains only pain indicator units, and these pain indicator units cannot register the intensity or type of the pain that a user is feeling when he/she activates the pain indicator units, then the intensity and type of pain that the user feels when he/she activates the pain indicator units will not be registered or transmitted anywhere. As another example, if a pain indicator unit is a lever and the user can only move a pain indicator unit with his/her tongue, and the input device can only accept input through the pain indicator unit, and the only input the input can accept is that the pain indicator unit has been turned, not the amount that it has been turned, then the only input that the input device can register or transmit about the response is that the user is in pain somewhere.

A related ninth principle is that if the input device cannot register all the information pertaining to a response that would ideally be registered, then statistical analysis may still be performed, using that data which the input device does register. For example, if the input device a user is using does not have the ability to register the user's pain's location, then statistical analysis may be performed without an entry for the user's pain's location, or, in some systems and embodiments, with an "NaN" to show that no entry was made.

A tenth principle is that, ideally, each response should include information about the intensity, type, and location of the pain the user is feeling's, and information about the user's age, gender, ethnicity, the user's physical location, and information about any health conditions the user has, along with information about other physical and/or mental conditions of the user, and whether the user is engaged in any special activity like a physical therapy session. However, this information will often not all be available. Many input devices will simply not have the capacity to register or record the user's pain's intensity, type, and location. For example, the user could be using an input device with pain indicator buttons that, when pressed, only can register the fact that the user is experiencing pain, and not the pain's degree, intensity, or location. Not all users will have given the above information such as information about their ethnicities and health conditions. If a response cannot include all of the above information, the response should be recorded in the individual database, the centralized integrated database, or any other relevant databases with whatever information is registered. In the above example, the fact that the user is experiencing pain, and not the pain's degree, intensity, and location is recorded, and the pain's degree, intensity, and location will simply not be factored into most resulting statistical analyses.

An eleventh principle, related to the ninth and tenth, is that if not all the desired data from a response is available, then it is better to record the data that is available than to record no data.

A twelfth principle is that if the amount of pain a user is feeling is either a lot more or a lot less than other users have felt with similar conditions, or is a lot more or less than the user themselves can be expected to feel in similar situations, this increases the chances that healthcare providers should be concerned about the user's condition.

A thirteenth principal is that in embodiments where pain types are recorded, statistical analysis of the pain types of the pain users experience can be performed, and useful insights possibly generated.

For example, for purposes of statistical analysis, different pain types in users' registered responses could be represented by different numbers. Then users' registered responses that contain pain types could be statistically analyzed, using the numbers, using similar concepts to those used in statistical analysis of registered responses that include degrees of pain. However, anyone interpreting the results of statistical analysis of the types of pain that users feel should consider the underlying data's nature when drawing conclusions.

TERM NUMBERS

The following term numbers shall apply to different components of the invention: Pain indicator unit (1). Display section (2). Alarm light (3), Server (4). Receiver (5). Battery charger (6). Solar panel (7). Mouth model (8). Human body model (9). Centralized integrated database (10). Individual database (11). Human body display (12). Suction cup (13). Alarm (14). Transmitter (15). Coordination module (16). Part model (17). Memory (18). Position Sensor (19). Remote program (20), Battery (21). App Calculation module (22). App coordination module (23). App receiving module (24). App display module (25). Proxy model (26). Integrated statistical display (27). Centralized calculation module (28). Processor (29). Centralized receiving module (30). Cover (31). Pain Indicator Piece (32). Specialized database (33). App transmission module (34). Pain indicator virtual unit (35). App input module (36). Display device (38). Time division indicator (39). ID input port (40). Data export port (41). PC (42). Pain indicator skin (43). App database (44). Centralized program (45).

Mouth models (8), human body models (9), part models (17) and proxy models (26) may be collectively referred to as signaling models in this application. Pain indicator virtual units (35), Pain indicator units (1), and pain indicator skins (43) may be collectively called indicator parts herein. Display sections (2), human body displays (12), app calculation modules (22) and centralized calculation modules (28) may be collectively called processing parts herein.

A scale of pain, or "pain scale", to be used with the invention, can be made known to the users before they use the invention. When users then indicate how much pain they are feeling, they can do this in accordance with the scale, and the amount of pain a user is feeling on one occasion when he/she uses the invention can be more easily compared to the amount of pain he/she feels on other occasions that he/she uses the invention, and the amount of pain that other users feel. The invention does not need to use a pain scale, but many of the invention's most effective embodiments will use a pain scale.

In embodiments using a pain scale, the user should ideally be able to easily indicate how much pain he/she is feeling each time he/she activates a pain indicator unit. For example, in embodiments where how hard the user presses a pain indicator button shows how much pain the user is feeling, the user can put more pressure on the pain indicator button until he/she reaches the pressure level that corresponds to the point on the pain scale that indicates the pain level the user is feeling.

One Example of a Pain Scale that can be Used with the Invention

One example of a pain scale to be used with the invention is:
0="No pain", most likely meaning that the pain indicator unit or pain indicator skin or pain indicator virtual unit is not being activated, 1="Slightly noticeable pain", 2="Slight pain", 3="Annoying pain", 4="Moderate pain", 5="More than moderate pain" 6="Severe pain", 7="Pain so bad the user cannot concentrate", 8="Pain so bad the user cannot perform regular activities such as walking", 9="Terrible pain", and 10="Pain as bad as you can imagine".

If this scale, or another scale with 10 levels is used, there can be a series of grooves with the numbers 1-10 in the input device next to each of the pain indicator buttons, and the harder the user presses a pain indicator button, the more grooves are shown, showing that the user is indicating a higher pain level. Alternatively, the grooves can be on the pain indicator button itself, and the more grooves are covered, as the user presses the pain indicator button, the higher the amount of pain the user is indicating.

In some embodiments each of the pain indicator units can shine or flash light of a different color, for each level of the pain scale. For example, on the scale of 1-10 above, the pain indicator units can flash light of a different color for each level when the user is indicating pain of each of the levels 1-10.

The user will decide which level is appropriate for the pain that he/she is feeling in each body part. This will be up to the user, who is the only person who knows how much pain he/she is feeling. The user's decision about which level of pain he/she is feeling may sometimes be subjective, but the user's experience of the amount of pain he/she is feeling will usually be the only, or the best, information available.

For this application's purposes, from here on, a user's or group of users' "pain level", is understood to mean the user's or group of users' "pain level on the pain scale being used with the embodiment of the invention being used". The same will hold true of a specific pain level experienced by a user or group of users; For example, a user's "nominated pain level" is understood to mean the user's "nominated pain level on the pain scale being used with the embodiment of the invention being used". For this application's purposes, whenever a level of pain, or pain level, is specified from this point on, in this application, it means "a pain level on a pain scale being used".

THE COMPONENTS

A pain indicator unit (1) is a physical unit that the user manipulates when the user is experiencing pain. "Activating" a pain indicator unit means using the pain indicator unit to send a signal. In most cases, the pain indicator unit (1) will be a button that the user presses when the user is experiencing pain. Buttons designed similarly to pain indicator units that are buttons can also theoretically be used when the user is experiencing other feelings, as explained above, but for the invention to work optimally, a user should only activate a pain indicator unit when he/she is feeling pain.

The pain indicator unit could also theoretically be in another form, such as a lever, which the user would move to show the pain degree that the user is experiencing. Pain indicator units that are levers could be placed in most of the locations where pain indicator units that are buttons can be placed, especially on a mouth model, human body model, part model or pain indicator piece. Input devices equipped with pain indicator units that are levers can be highly useful to users who cannot move their hands or feet, or who otherwise are unable to press pain indicator buttons. For example, a user whose hands and feet are paralyzed may most conveniently be able to move a pain indicator unit that is a lever with his/her tongue. The more the user moves that pain indicator unit, the higher is the pain level that the user indicates that he/she is feeling.

In some embodiments, when the user manipulates a pain indicator unit, for example, when the user presses a pain indicator button, or moves a pain indicator level in a pre-specified way, the manipulation causes an alarm to sound, causes an alarm light to sound, or both. Methods known in the prior art will allow pain indicator units of these types to be constructed.

Using methods known in the prior art, a pain indicator unit (1) that is a button can also be designed that monitors how hard it is pressed. With this type of pain indicator unit, the user could indicate the degree of the pain he or she is experiencing by pressing the pain indicator unit harder— The more pain the user is experiencing, the harder the user should press the pain indicator unit.

One way to monitor how hard the pain indicator unit is being pressed is to design the pain indicator unit to be pushed down more, as the user presses it harder. Grooves or markings can also be placed alongside, or on, the pain indicator unit, so that the user can approximately measure how far down the pain indicator unit goes when the user presses it. For example, the grooves alongside the pain indicator unit might include a "1" for when the user depresses the pain indicator unit a certain amount, a "2" for when the pain indicator unit is depressed more, and a "3" for when it is depressed still more. Then the user can depress the pain indicator unit even more if the user is experiencing greater pain and desires to depress it more.

A pain indicator unit, such as a pain indicator button might also be designed with an alarm light (3) underneath, inside, or next to it, wherein the alarm light will glow when the pain indicator unit is pressed, and the color, in which the alarm light glows will change depending on how much the pain indicator unit is being depressed, or some other characteristic of the alarm light (Like the pattern in which it flashes) will change depending on how much the pain indicator unit is being depressed: In one example, the alarm light can glow yellow for the pain indicator unit being depressed a small amount, orange for the pain indicator unit being depressed a larger amount, and red for the pain indicator unit being depressed more than that. Here, the amounts by which the pain indicator unit is pressed when the alarm light flashes, yellow, orange, and red, respectively, are "levels" to which the pain indicator unit can be pressed. The colors do not need to be red, yellow, and orange, but can be whatever colors the pain indicator unit and/or alarm light's manufacturer desire. If there are fewer or more than three "levels", respectively, to which the pain indicator unit can be depressed, then the alarm light can still be designed with the capacity to flash in a different color(s), with each color representing a different level to which the pain indicator unit is depressed. For example, if there are ten "levels" to which the pain indicator button can be depressed, then the alarm light can be designed to flash in a different color for each of these levels. Methods already known in the prior art will allow this, and any of them can be used.

A pain indicator unit, such as a pain indicator button can also be designed wherein an alarm will make a different sound, or a different alarm will be sounded, for each level to which the user depresses the pain indicator unit. For example, if used with a pain scale that has ten levels of pain, the pain indicator unit will cause an alarm to make a different sound, or cause a different alarm to make a sound, depending on which of the ten levels of pain the user indicates that he/she is feeling by pressing the pain indicator unit.

If a pain scale is used (Such as the pain scale discussed in the section "One example of a pain scale to be used with the invention"), then the alarm light should ideally glow in a different color for each level of the pain scale.

If the pain indicator unit is in the form of a lever, then the user can indicate the amount of pain he/she feels by turning this lever more. For example, in some embodiments, each 30-degree turn on this lever will show the user is indicating he/she is feeling a pain level that is "1" higher on the pain scale. An alarm light in, or under, the lever, can also glow in a different color for each level of pain the user indicates he/she is feeling. An alarm can also sound in a different color, or a different alarm can sound, for each level of pain the user indicates he/she is feeling.

In theory, the user can communicate to the pain indicator unit how much, or how little, pain the user is feeling based on some other method besides how hard the user presses a pain indicator unit that is a button or turns a pain indicator unit that is a lever. For example, in some embodiments, the user could communicate that the user is feeling more pain by moving the user's finger in a certain pattern, like a circular pattern, on the pain indicator unit, or moving the user's finger faster across the pain indicator unit, to communicate more pain.

The pain indicator unit can cause an alarm (14) that is part of the input device of which the pain indicator unit is a part, to sound when the pain indicator unit is activated, in addition to, or in replacement of, an alarm (14) located somewhere else that is in communication with the pain indicator unit (1).

An alarm light that flashes a different color depending on how hard the user presses a pain indicator button, turns a pain indicator unit that is a lever, or otherwise manipulates a pain indicator unit does not need to be part of the input device that includes that pain indicator unit. The alarm light can be operatively connected to a receiver that is in communication with a transmitter, where the transmitter is operatively connected to the pain indicator unit.

Multiple patients in a group can each have access to one or more pain indicator units, each of which causes a different-sounding alarm to sound, and each of which causes a different-looking alarm light to flash. Then, healthcare providers who are treating the group of patients can easily figure out which patients are experiencing pain, and the pain's degree(s) and/or location(s), by looking at the flashing alarm lights and listening to the alarms that are sounding.

For example, a system could be created with multiple pain indicator buttons, that covers multiple rooms with patients, where an orange alarm light means the patient in a first room has pressed a pain indicator button, and a red alarm light means the patient in a second room has pressed a pain indicator button, and a high-pitched alarm means that a patient's leg hurts, while a low-pitched alarm means that a patient's arm hurts. Each patient, in this scenario, is able to indicate which body part hurts by pressing a pain indicator button that represents that body part. Therefore, an orange alarm light combined with a low-pitched alarm means that the patient in the first room's arm is hurting. The specific colors and sounds the alarm lights and alarms make here are exemplary, and other and more colors and sounds can be used. The system's needs and the number of users, and number of separate body parts where each user can indicate, using the system, that he/she is experiencing pain, might influence which colors and sounds the alarm lights and alarms, respectively, will be designed to make.

Healthcare providers in an emergency might use a system of this type to prioritize which patients to visit, treat, check on first, or check on more often. For example, if alarms or alarm lights show that some patients in a ward are experiencing more pain than others, healthcare providers working in the ward might decide to check those patients more often, or investigate why those patients experience more pain. If two patients are in pain but one is experiencing much more pain than another, the healthcare providers working in the ward might decide to give the first patient morphine before the second.

In some embodiments where statistical calculations are performed, using the users' responses, each response is considered to have a "minimum duration", for purposes of statistical calculations using that response. This may be useful for giving appropriate weight to responses that have short duration but indicate pain. For example, when trying to calculate the average pain level, on a pain scale, that a user expressed in a body part, in a time period, it is necessary to find out how long the user expressed pain of each level on the pain scale in that body part. In some embodiments, the program or computer hardware component doing the calculating may then assume that each of the user's responses relating to that body part has a minimum duration of 1 second. This will give the user's short responses an appropriate significance level. If the user activated a pain indicator unit for less than 1 second, that response is considered to be 1 second long. If the user activated a pain indicator unit for more than 1 second, the response is considered to have whatever length the response had.

In general, increasing the minimum response duration increases the significance of a user's short responses.

Many embodiments that use statistical analysis of responses will have a minimum response duration of 1 second, but others may have longer or shorter minimum response durations. The minimum response duration would also apply to periods where the user is expressing information but not making a response; the minimum duration for expressing information would be the same as the minimum response duration.

Some Situations where Identifying the User is Helpful

In some embodiments, and for some uses of the invention, it is helpful to identify the responses the same individual user makes on different input devices. One reason might be to create a long-term picture of the pain the individual user feels in different body parts, to detect patterns in this pain, and to use information about the individual user's pain as part of a study of the pain felt by a user population that includes the individual. All methods of identifying the individual user who registered responses are explicitly part of the present invention. One such method is to have ID input ports on some input devices, where the user inputs the user's user ID, and then starts using the input device to register responses. The user may also indicate on the ID input port that a new user is using the input devices, then input the user's user ID, and then start using the input device to register responses.

Another method may be to have a person working for the entity that controls a large number of input devices and is letting users borrow and use them to ask each user for that user's input ID, when the user borrows the input device, and then the person working for the entity programs the input device with the user's user ID. Then, when a new user borrows the same input device, the person working for the entity programs the input device with the new user's ID, etc.

Some Ways to Account for Equipment Limitations
Re: Input Devices

Equipment limitations might cause a scenario where some input devices which send users' registered responses to the display section (2) or human body display (12), or to a location such as an individual database (11) or the central-ized integrated database (10) where the registered responses can later be examined by a centralized calculation module (28), or app calculation module (23), allow users to give more specific responses than other input devices concerning the location and degree of users' pain. For example, some of the input devices operatively connected to a display section (2) or human body display (12) might have a single pain indicator unit for the user's right arm and hand, allowing a user to designate his/her right arm and hand as an area where the user is feeling pain, while other input devices operatively connected to the same display section (2) or human body display (12) might have separate pain indicator units for the right, arm, the right hand, and each of the right hand's fingers, allowing the user to express which of these body parts, specifically, is a location of pain.

In this example, a response indicating that the user feels pain in one of the user's right fingers is considered "more specific" than a response indicating that the user feels pain in the part of the user's body including the right arm, hand, and fingers, because healthcare providers and caregivers cannot know from the less specific response whether the user is feeling the pain that she reports in one part of the group of body parts or in all of the group, or, if the user is feeling pain in one part of the group of body parts, then which body is the pain's location (For example, in the entire right arm and hand vs. one of the right fingers, or one of the right fingers versus higher up on the right arm).

Caregivers and healthcare providers also cannot know from a less specific response whether the user is distorting the amount of pain the user is registering through subjective criteria (A user might decide that a large amount of pain in one finger is "less important", and erroneously conclude that it is therefore less intense, than the same amount of pain felt in a larger area, such as all of his/her arm, hand, and the fingers attached to the hand). This effect can be reduced by instructing a user ahead of time to record the "highest" amount of pain they are feeling in any part of the area which a pain indicator unit on the input device available to the user is supposed to represent.

Every method of detecting whether a less specific response indicates pain in more body parts than a more specific response that indicates pain in one or more of the same body parts in which the less specific response indicates pain, that is within the prior art is explicitly within this application. One such method in some embodiments, is for the human body and its internal features such as bones and organs, to be divided into a large number of "sections" for the purpose of analyzing pain's source. Each section will have a "marker", which is a short code that, when included in a response, indicates that the section was part of the body part to which a response applies. Some input devices will include the capability that each response transmitted from those input devices will include the markers for the body part the pain indicator unit, pain indicator skin, or virtual pain indicator unit that the user activated to make the response represents. Such a capability can be created in various ways. One way, present in some embodiments, is for, in an input devices that includes a processor a processor to be pre-programmed with a record of the markers for the sections for which each of the input device's pain indicator units, when activated, indicates pain. Then, the processor will cause each response sent from the input device's transmitter to include the markers relating to the pain indicator unit(s) the user activated to make that response. Another way, present in some embodiments, is for the pain indicator units to be designed so that when each pain indicator unit, when activated, sends out an impulse, that impulse will contain the markers for all the sections in which that pain indicator unit, when activated, is supposed to indicate pain. If the marker for a section is present in a registered response, the processing part assumes the regis-tered response to represent that the user felt the indicated pain level in that section. Some input devices are pro-grammed so that each response registered using one of these input devices is coded to include markers for the sections to which that response is supposed to apply. Then, a processing part analyzing the user's responses will examine the markers in the response and count a first response as more specific than a second response that includes all the markers in the first response and also includes other markers.

The display section (2), human body display (12), cen-tralized calculation module (28) or app calculation module (22) can be programmed or designed in multiple ways to deal with the scenario of some input devices not being able to register more specific responses than others. For example, in the above case, the pain level that the processing part displays for the whole arm can be calculated by including the responses from each input device on which the user expressed information: When calculating the average pain level in the arms, hand, and fingers the responses from the input devices that only include one pain indicator unit to indicate pain in the combined area of the arm, hand, and fingers would each count as one response for the pain level of the combined area including the arm, hand, and fingers. The responses from the input devices showing pain in a more specific area, including one of the fingers, would also each count as one response for purposes of calculating the average pain level of the combined area including the arm, hand, and fingers. The processing part then calculates the average pain level in the arm, hand, and fingers by averaging the responses pertaining to any part of the arm, hand, and fingers received from the input devices sending the user's expressed information. In other words, the processing part calculates the average pain level in the less specific area, and also other statistics concerning the pain level in the less specific area, by assuming that a) each response pertaining to the whole of the less specific area, and b) each response pertaining to any more specific area that is part of the less specific area, has equal weight and is counted as a response applying to the whole of the less specific area. In embodiments of this kind where different colors represent different ranges on a pain scale being used, in a human body display (12) where the colors of body parts in the human body display (12) change based on users' calculated average pain level in those body parts, the arm, fingers, and hand on the human body display (12) will glow in the appropriate color based on the calculated average pain level the human body display (12) calculated. Likewise, in embodiments of this kind using a display section (2) where the colors of images of body parts change based on users' calculated average pain level in those body parts, the images on the display section (2) representing the user's pain level in the arm, fingers, and hand will glow in the appropriate color based on the calculated average pain level.

Alternatively, the average pain amount being shown for a more specific body part (Such as a certain finger, in the example above) can be calculated through the processing part assuming that each response indicating pain in a less specific area also indicates pain in more specific areas that are part of the less specific area, and making the following calculations, where S represents a less specific body part, S1, S2, . . . SN represent more specific body parts that are parts of S, CS represents less specific responses for body part S, and CS1, CS2 . . . CSN represent responses for body parts S1, S2 . . . SN.

A. Average pain level for those parts of body part S for which more specific responses are not available is calculated, by averaging the responses, that include markers for those parts of body part S.

B. Average pain level for each part S1, S2, . . . SN of the less specific body part S for which responses CS1, CS2, etc. are available is calculated, by averaging CS1, CS2, etc. and CS. Essentially, when determining pain level and doing other statistical analysis for those portions of a body part for which more specific responses are available, counting both the more specific responses and the less specific responses that applied to any larger portion of the body part which included the portion of that body part to which the more specific responses applied.

Other methods exist of calculating the average pain levels in parts of users' bodies, when a user has indicated the amount of pain the user is feeling in a body part using both less and more specific input devices. For example, the device or program (The human body display (12), display section (2), app calculation module (23) or centralized calculation module (28)) can include any combination of the user's registered responses from the following categories (A, B, and C) of input devices, and/or other information the user expressed, while using registered responses from categories A, B, and C in the data used to calculate the user's average pain level in a body part or make other statistical calculations related to the pain the use felt in a body part. The three input device categories are: A. Input devices using pain indicator units that indicate pain in a body part, that the user used to register pain levels. B. Input devices using more specific pain indicator units that indicate pain in part of said body part and that the user used to register pain levels. C. Input devices using less specific pain indicator units that indicate pain in a group of body parts that includes said body part. For example, the user's registered responses in one, two, or three of these three categories, can be added into the numerator used to calculate the relevant average, with the denominator used for calculating the average increased by the number of relevant data points in the same category(s). The processing part calculating the average can add the relevant categories to the numerator and denominator.

Variations of the above calculation methods can also be used where the average pain level for each marker is calculated based on any responses that included that marker, from any input devices the user used.

The need to reconcile responses from input devices with differing exactness amounts is only important when the same user has used input devices with different exactness amounts.

Some embodiments of the human body display (12), display section (2), app calculation module (23) or centralized calculation module (28) can use the user's combined response data and other expressed information in categories A, B, and C above, when making statistical calculations about the user's responses, some embodiments will use categories A and B, some embodiments will use categories A and C, some embodiments will use categories B and C, and in some, the person commanding the processing part can pick which of categories A, B, or C to use.

Another way that the display section (2), human body display (12), app calculation module (23) or centralized calculation module (28) can make statistical calculations concerning the user's pain levels, in a body part, when the user has been using both less and more specific pain indicator units is by assuming that each response that includes a marker for a section applies to that section. Then, the processing part can make statistical calculations regarding each section. This may be especially helpful when a user registers, on a first input device, responses which includes some markers, and later registers, in one or more second input devices, responses that include some, but not all, of the markers in the user's responses from the first input device, while at least one of the responses on the first input device include at least one marker that was not present in at least one of the user's responses from at least one of the second input devices.

In some embodiments of the invention, the markers will be "grouped" into clusters, for certain display purposes. The clusters will each represent a specific body part, will each include all the markers pertaining to areas of that body part, and which markers go into each cluster will be decided ahead of time. Then, for purposes of performing statistical analysis and displaying graphs and other visual representations of the analysis' results, the analysis will be performed on the cluster as a whole. The responses pertaining to all of the individual markers in the cluster will be added together, the refining function will be applied to them, and the result displayed on the whole of the body part, on the human body display (12), or shown on any field pertaining to the whole of the body part, on the display section (2).

In some embodiments of the invention, a user using a processing part can also command the processing part to calculate and display, a statistic such as the average pain level, over a certain time period, for a subgroup of the users of the input devices directly or indirectly transmitting to the processing part.

For example, in some embodiments using the display section (2) or human body display (12) the viewer can gain the following information: The average pain level the users in the subgroup experienced in a body part, and other statistical information regarding the pain level the users in the subgroup experienced in that body part, based on the responses registered through the input devices that both A) The defined subset of users is using and B) Are operatively connected to the display section (2) or human body display (12). Examples are A. A group of input devices being used by users who have a certain medical condition, or B. A group of input devices being used by specific users, or C. A group of input devices defined in some other way. The command can be given to the display section or human body display in any of the ways known in the prior art, including, but not limited to, the command being typed into the display section (2) or human body display (12).

If a viewer using the display section (2) or human body display (12) wishes to focus on a subgroup of a group of users, and the viewer, display section (2), or human body display (12) has access to the user IDs of the users in the subgroup, then in some embodiments, some of the ways that a viewer could define the subset of users are A. Inputting the individual users in the subgroups' user IDs into the display section (2) or human body display (12). B. Inputting a common characteristic, or group of characteristics, of the individual users in the subgroup being studied, into the display section (2) or human body display (12). The display section (2) or human bodV display (12) can then request the centralized calculation module (27) to find the user IDs of all the users in the group in the centralized integrated database, and find responses belonging to those users in the group that have, listed in their individual data, all the characteristics the viewer inputted. The centralized calculation module sends these group members' user IDs back to the display section (2) or human body display (12). The display section (2) or human body display (12) then bases the display data on its screen on input received from input devices being used by these group members. Alternatively, in some embodiments, the display section (2) or human body display (12) directly searches the centralized integrated database (10) for responses belonging to those users in the group that have, listed in their individual data, all the characteristics the viewer inputted, and then the display section (2) or human body display (12) "filters" the input data it is receiving, to only consider information expressed through the input devices the targeted user subgroup are using, when making calculations to create display data. C. If the display section (2) or human body display (12) uses an app database (44) with individual data, then the display section (2) or human body display (12) can search the individual database for responses belonging to those users in the group that have, listed in their individual data, all the characteristics the viewer inputted. Then the display section (2) or human body display (12) will base the display data shown on its screen on the input received from the input devices the users in the subgroup received. D. Having the display section (2) or human body display (12)'s programming include a database that includes the user IDs of the users in the group, and those users' individual information. Theoretically, this database could include information added by the entity maintaining the display section (2) or human body display (12). Examples are how long users have been in a hospital ward, or how long since users have had braces installed on their teeth. All the input devices users in the group are using will send information to the display section (2) or human body display (12), and the display section (2) or human body display (12) will refer to the database with the users in the group's user IDs, and will search that database's individual information for users with the characteristic or combination of characteristics that the viewer inputted. The characteristic or combination of characteristics could also potentially include information added by the entity maintaining the display section (2) or human body display (12), like a specific length of prior stay in the hospital ward. Then, the display section (2) or human body display (12) will only incorporate the data received from the input devices those users are using into the calculations underlying the display data the display section (2) or human body display (12) displays on its screen.

In some situations, healthcare providers can organize the provision of input devices to the users and track which user gets which input devices, so the viewer knows which user has each input device ahead of time. If the individual users have inputted their user IDs into the input devices they are using, the viewer can find out more information about the pain experienced by a subgroup of the users who are using the input devices sending expressed information to the display section (2) or human body display (12). The display section (2) or human body display (12) can also send a request directly or indirectly to the centralized calculation module (28) to find members of the subgroup, or their registered responses, in the centralized integrated database.

A display section (2) is an electronic display that displays information about whether one or more users have activated pain indicator unit(s), pain indicator virtual units, or pain indicator skins, that either A) Are operatively connected to the display section, or B) Directly or indirectly sent the registered responses to the centralized integrated database (10), specialized database (33), an app database, or individual databases (11), where the responses can be sent to the display section (2), or C) Directly or indirectly sent the registered responses to an app database (44) saved in the display section (2). If the input devices the users were using registered the amount(s) of pain the users indicated that they felt, the display section can also display indicators of the amount(s) of pain these users indicated they felt. The display section (2) can be operatively connected to a device such as a receiver that receives input from the transmitters operatively connected to the pain indicator units, virtual pain indicator units and/or pain indicator skins the users are using. Alternatively the display section can receive input from those input devices themselves, or from another device that is otherwise operatively connected to those input devices. In some embodiments, the display section (2) can also receive, and make statistical calculations about, input from the centralized integrated database (10) or one or more users' individual databases (11), a specialized database, or an app database saved within the display section (2). The display section (2) also has the capacity to make statistical calculations about the expressed information it receives, and display statistical calculations' results on its screen.

This allows dental personnel or other healthcare providers to quickly learn, by looking at the display section (2), which of the users under their care is experiencing pain or has experienced pain in the recent past, and where, and how much pain, the users experienced or experience. The healthcare provider(s) can then try to find solutions for the user's pain, or the users' underlying health conditions. Healthcare providers can also find differences between the degree, location, and other characteristics of the pain that different individual users, and different user groups, experience, then try to find why the differences exist, and help the users with this information.

A display section (2) is different from a "human body display" (12), which specifically displays an image of a human body or part thereof. A display section (2) does not display an image of a human body or part thereof for purposes of showing where the user is feeling pain.

In all embodiments of the display section (2) or human body display (12) that use a pain scale, with different pain levels represented by different colors, shades of gray, patterns, or something else which is visually distinguishable to viewer, the pain scale, and the colors, etc. representing different pain levels on the pain scale should be made known to the viewer, so the viewer can more easily interpret what the viewer is seeing. In some embodiments, explanations of the colors, etc. that represent pain levels are backdrop data displayed on the screen for the viewer to see and review them.

The users whose expressed information was used to create the display data shall sometimes be called the "source users" herein. The specific subcategory(s) of the source users' expressed information, on which the display data is based is called the "source data" herein.

In some embodiments, the viewer can use the display section (2) or human body display (12) to further explore the pain patterns of individual users, or a user population, to understand the users' pain, what is causing the users' pain, to use the users' pain patterns to detect any health conditions the users may have, and hopefully create and/or improve solutions for the users' pain and underlying conditions that cause the pain. To further explore users' pain patterns, the viewer can use the display section (2)) or human body display (12) to change one or more of the below parameters ("Parameters A-G") in some embodiments, which will help the viewer to find patterns in users' pain, understand differences between the pain different users or user groups experience and possibly how to alleviate users' health conditions. The function the viewer wants to apply to the source data, to generate the display data the display section or human body display (12) is showing, is called the "refining function". In some embodiments, such functions can include relationships between the results of other functions and/or may be constructed using processes based on SQL (Structured Query Language) or other programming languages. In some embodiments, the viewer can pick a source data category, such as the registered responses, and apply another function to the category. Picking the category is considered part of the "refining function".

Parameters A-G are: A. The number and length of the time periods from which the source data is drawn. Examples of number and length are, respectively, 24 1-hour time periods. "24" is the number and "1 hour" is the length. Other examples of number and length of time periods are possible. B. Whether the display section shows the results of application of the refining function to the source data in one time period, shows the results of application of the refining function to the source data expressed during each time period in succession (which would result in showing the results of the refining function's application to the source data expressed during one of the chosen time periods, the results of the refining function's application to the source data being shown for another of the chosen time periods, etc.), or results of the refining function's application to the source data from the group of time periods, (such as a taking a quantity's value in each of the time periods and averaging those values) or the combined source data from all the time periods (such as the average of a quantity's value during the entire time period from the first time period's beginning to the last period's end). Source data from each of the selected time periods for which source data is available will be used with the function applied to the source data. C. What the "refining function" is. D. If the viewer wants the source data to be drawn from specific users, the user ID(s) for the individual user or users, or characteristics of the group of users, or subgroup of a group of users, who are the source users, and if the viewer wants the source data to be drawn from specific input devices, the device ID of the individual input device or input devices (The device IDs of input devices are broadcast in the responses that the input devices broadcast, and in some embodiments these device IDs are also saved in the Databases in which the responses are saved, so they can be searched for) or characteristics of the group of input devices, that are the sources of the source data. For example, "characteristics of the user group" could be that a specific health condition is mentioned within the users' individual information, during a certain, defined, time period. E. Whether the viewer wants the refining function to apply to the source data received at a certain point within the time periods (Example: At 9 A.M. GMT during each 24-hour period), or to apply to the source data received throughout each time periods (Throughout each 24-hour period, in this example). F. Whether the viewer wants a nominating period and nominating rule to be used, and, if so, what the viewer wants the nominating period and nominating rule to be. G. Whether the viewer wants each piece of the display data to be shown on the body part to which it pertains, or close to that body part, or (in some embodiments) in another location.

Forms in which the display section can display the display data can include, but are not limited to, A. Numbers including the results of the refining function's application to the source data. Nonexclusive examples of such numbers are the mean, median, mode, standard deviation, and moving averages over the current time period or the number of time periods the viewer desired, and other statistical measures for the pain levels the source data represented; B. The colors of fields that indicate pain levels expressed in the source data, and C. The colors of fields indicating the results of the refining function that the viewer commanded the display section (2) to apply to the source data. Nonexclusive examples of such fields are small circular or rectangular fields, shown on the display section (2)'s screen, where each small circular or rectangular field glows in a certain color reflecting the refining function's result for a group or subgroup of source users. In one example, the refining function's result is the average expressed pain level the display section has received from a subgroup of the input devices (The display section will label each of the fields with a name for the subgroup that field represents) within a certain time period, the viewer picked. In this example, the refining function's result for each source user subgroup falls within a certain range (Different colors show the average expressed pain level falls within different ranges), represented by a color, and each of the small circular or rectangular fields changes colors when the average pain level the display section has received from the input devices used by that subgroup within the time period moves to a range represented by another color. Here, the fields, the fields' labels, and any label showing which color represents which range are backdrop data, and the fields' colors are display data.

This is also true of situations where an individual's data is being examined, a.k.a. situations where there is one source user.

The visual indications holding the display data of the refining function's result applied to the source users' data can have other forms, and if the visual indications take the form of small fields shown on the display section's screen, the small fields can have another appearance besides being circular or rectangular.

In some embodiments, if the viewer adjusts any of parameters A-G above, the display device will recalculate the results of the refining function (which may have been adjusted)'s application to the source data (the group of users who count as source users may have been adjusted) and the display section will adjust the background data (Displayed items such as field labels and other information explaining what the display data means) appropriately and show display data reflecting the new results.

In some embodiments, the display section (2) will show display data concerning an individual user's pain levels, and in some of these embodiments the viewer can adjust one or more of parameters A-G above to get a better understanding of the individual user's pain and physiological state.

An example is if the viewer selects a nominating period of 1 hour and a nominated pain level of the highest pain level in that hour. Then the viewer asks the display section to show a moving average of the single user's nominated pain level for the preceding 5 hours during each of the past 10 hours in succession. The display section (2) will then calculate the moving average of the source user's highest pain levels during each of the preceding 5 hours in each of the past 10 hours (a.k.a. the average of the source user's highest pain level from the hour 10 hours ago, and the hours 11, 12, 13, 14, and 15 hours ago, and the average of the source user's highest pain level from the hour 9 hours ago, and the hours 10, 11, 12, 13, and 14 hours ago, etc.), and will show these number in succession and show the appropriate color in succession representing these numbers in a field on the screen.

In some embodiments, the display section can have multiple fields showing the display data, broken down between display data based on expressed information for multiple body parts of the source users, and, if appropriate, multiple numbers showing the results of the refining function applied to multiple of the source users' body parts. The display section (2) would generally be programmed to show a field and number for each body part which part of the expressed information is designated as representing, either designated by the input device that sent the expressed information to the display device, or designated in the database the display device got the expressed information from. For the display section to show this field and number, the source data would have to include information about which response(s) applied to each body part. One such way is use of responses containing markers, so that the display section (2) or human body display (12) can find which body part(s) each response applies to, by examining the markers in that response and concluding that the response applies to the body areas with markers that appear in that response. One way is for the source user(s) to have access to input devices that allow the user to indicate each source user's pain level in each of multiple body parts. If the source data is specified as being drawn from specific input device(s), instead of specific users, the responses from these input devices would need to include information about what body part is being represented as a source of pain in each response. Responses containing markers is one such way, so that the display section (2) or human body display (12) can find which body part(s) each response applies to, by examining the markers in that response and concluding that the response applies to the body areas with markers that appear in that response.

Likewise, in some embodiments, if the display section is analyzing the source data of a user group, with multiple subgroups, and with each user in the subgroups having access to input devices which can be used to register responses for multiple body parts, the display section can show a field on its screen which shows the color representing the range into which the refining function's result for each subgroup falls, for multiple body parts (In other words, multiple fields per user subgroup, each field representing a body part) and the display section can also show the refining function's numerical results for each subgroup, for multiple body parts.

A human body display (12) can show statistical information about pain levels an individual user or user group feels, and in some embodiments this can be further broken into statistical information about subgroups of the user group, and into statistical information about the pain the source users in the user group, or subgroups of the user group, felt in different body parts. This is in addition to showing an image of a human body or part thereof. If a human body display (12) shows any display data in addition to an image of all or part of a human body, some or all of this display data can be, but does not have to be, superimposed on the human body display's electronic image of all or part of the human body.

Any electronic device with the needed capabilities can function as the display section (2) or human body display (12). The same electronic device can theoretically perform the function of a display section (2) and also perform the function of a human body display (12) by showing the image of all or part of the human body. Both the display section (2) and human body display (12) can be considered specially programmed computers.

In some embodiments, the display section (2) or human body display (12) can include one or more of the following: A computing system including a processor for processing digital data, which, in most embodiments, is the information the processor has directly or indirectly received from one or more of the Databases and/or the information the processor has directly or indirectly received via a receiver(s) from pain indicator units, pain indicator skins, and pain indicator virtual units in input devices with transmitters; A memory coupled to the processor for storing digital data (in some embodiments this may not be strictly necessary); An input digitizer coupled to the processor for processing digital data; And an application program stored in the memory and accessible by the processor for directing the processor in processing of the digital data. The electronic device that displays video, coupled to the processor and memory will display information derived from digital data the processor processed. As those skilled in the art will appreciate, the computing system may include an operating system (e.g., Windows, OSX, iOS, UNIX, Linux, MacOS, Android, etc.) as well as various conventional support software and drivers.

A display section (2) or human body display (12) can be operatively connected, wirelessly or otherwise, to multiple input devices being used by multiple users. One way this can be done is if the users have inputted their user IDs on the input devices, and the input devices have transmitters and transmit the responses uses make on the input devices to the display section (2) or human body display (12). The display section (2) or human body display (12) can also display information about whether multiple users have activated pain indicator units, pain indicator skins, and/or pain indicator virtual units, especially in cases when the users each have access to more than one indicator part (For example, when the users each have access to a human body model with multiple pain indicator buttons).

A display section (2) or human body display (12) can be designed or programmed to receive input from multiple users, as identified by each user's unique ID, and to show display data based on those users' registered responses and other information the users expressed. The input can be broadcast by transmitter(s), operatively connected to the input devices those users are using, and the input can be received wirelessly or via the internet by a receiver operatively connected to the display section (2) or human body display (12). The processor(s) in the display section (2) or human body display (12) can then further process the input in various ways, some of which are described herein. For example, a display section (2) or human body display (12) could receive input from the indicator parts on the input devices that multiple users use at their homes, and then process this input.

A display section (2) or human body display (12) can also be designed or programmed to receive input from multiple input devices, which may be used by multiple users or one user, and the display section (2) or human body display (12) will calculate and show, on its screen, display data which can include which of those input devices is being user to register a response, the degree(s) of the response(s), the average degree(s) of subcategories of the responses, and possibly other information concerning the responses and the users and/or input devices that are their sources. For example a display section (2) or human body display (12) can receive input from all the input devices the patients in a hospital ward are using, in a situation where the users have not entered their user IDs or other identifying information on the display devices. Below, the term "multiple sources" encompasses both "multiple users" and "multiple devices" and can refer to either or both of these scenarios.

Some embodiments involve the display section (2) or human body display (12) showing information about A. Whether one specific user has activated the pain indicator units, pain indicator virtual units, and/or pain indicator skins operatively connected to the display section (2) or human body display (12) (In some versions the display section (2) or human body display (12) will show whether that specific user has activated these pain indicator units, pain indicator virtual units, and/or pain indicator skins within a specified time period, such as 3 to 4 PM on a specific date or a specified time period before the present (the time the information is being viewed), such as the last 4 hours before the present), B. Which indicator parts, the user activated, and C. The pain degree(s) the user indicated when activating the indictor parts. In some of these embodiments using the human body display (12), the parts of the electronic whole or partial human body image shown by the human body display (12) will glow, that correspond to the user's body parts the activated pain indicator units, pain indicator virtual units, and/or activated parts of the pain indicator skins represent. For example, if the user has pressed a pain indicator button, that, when pressed, shows that a user is feeling pain in his/her shoulder, where the pain indicator button is on a proxy model (26), the shoulder in an electronic human body image, on the human body display (12) will glow. If a pain scale is used, the shoulder in this example can glow in a color representing the pain degree the user indicated by activating the pain indicator button. For example, the shoulder of the image of the human on the human body display (12) will glow red if a pain scale is used, and "red" is the color indicating a pain level of 6, and A. The pain indicator button is designed so that the user indicates the user is feeling a higher pain degree by pressing the pain indicator button for more time, and B. The user pressed the pain indicator button that, when pressed, shows that the user is feeling pain in the user's shoulder for enough time to indicate the user is feeling pain level 6, which is the pain level the color "red" represents.

When used with a pain scale, a display section (2) or human body display (12) can be designed to quickly show the average pain levels a group of users feel in multiple body parts, in a system where different colors represent different pain levels, in the following way: First, the display section (2) or human body display (12) receives input comprising multiple source users' registered responses for different parts of their bodies. The nominated pain levels each source user registers for each body part will then be averaged with the nominated pain levels each other source user in the user group registers for the same body part (For example, the nominated pain levels for the left foot, registered by these source users can be averaged, and, the nominated pain levels for the right foot, the source users registered can be averaged), either in a processor attached to the display section (2) or human body display (12), a processor in the display section (2) or human body display (12) itself, or a processor in another device.

If a human body display is being used, the human body display (12) can then display each body part in the color that represents, on the pain scale being used, the pain level represented by a color that is closest to the average of the pain levels the source users registered for that body part.

If a display section (2) is being used, in the above example, the display data that the display section shows, that represents the users' pain levels in a body part, can be displayed in the solid color representing, on the pain scale being used, the pain level represented by a solid color that is numerically closest, to the average of the pain levels the users registered for that body part.

For example, if the average pain level in the left leg the source users report using the input devices operatively connected to the human body display (12) is closest to the pain level "green" represents, then the left leg on the human figure on the human body display (12) will glow green.

The display section (2) or human body display (12) can also be designed to show the display data representing the pain level in each body part in a) The whole color that, on the pain scale being used, represents the closest pain level represented by a whole color to the average pain level the users are expressing, b) A whole color that, on the pain scale being used, represents a range into which the average pain level falls, or c) An "intermediate level" color scheme representing a blend between the colors that, on the pain scale being used, represent two pain levels that the average pain level in a body part source users are registering is in between, if the average pain level in a body part source users are registering using the input devices operatively connected to the display section (2) or human body display (12) is between two levels on the pain scale being used (For example, between 1 and 2).

A nonexclusive example of an "intermediate level" color scheme is: When the refining function's result for the body part is between two pain levels, represented by different solid colors, on the pain scale being used, the ratio of pixels in the solid color representing the lower pain level to pixels in the solid color representing the higher pain level, in the body part, will be expressed as follows:

LNSC is the lower number represented by a solid color, and that color is designated SC1. HNSC is the higher number represented by a solid color, and that color is designated SC2. SFRAN is the actual result of the refining function applied to the viewer's chosen category of expressed information shall be:

$$((SFRAN-LNSC)/(HNSC-LNSC)=\% \text{ of pixels in body part colored SC1.}$$

$$1-\% \text{ of pixels in body part colored SC1}=\% \text{ of pixels in body part colored SC2.}$$

An example of this color scheme in use is: If the average nominated pain level in a body part the users are expressing using the input devices is 3.7, and the color representing the pain scale's level 3 is blue and the color representing the pain scale's level 4 is yellow, the human body display (12)'s processor(s) will cause the pixels in the image of that body part in the human body display to glow, with a ratio of 7 blue pixels for every 3 yellow pixels.

The blue and yellow pixels are intermixed with each other.

In some other versions of the display section (2) and human body display (12), the percentage of pixels in the body part that glow in color SC1 and the percentage that glow in color SC2 are governed by the above formula, but the pixels glowing in color SC1 are clustered together and the pixels glowing in color SC2 are also clustered together.

In some other versions of the display section (2) and human body display (12), all the pixels in the body part will change shades for every difference of a certain amount between LNSC and HNSC (Often each 0.1 difference between LNSC and HNSC when a pain scale that goes from 1-10 is being used).

There are other ways that the display section (2) or human body display (12) can also display, for each body part, the result of the refining function applied to the source data. For example, the display section (2) or human body display (12) can display the number which is the result of the refining function being applied to the source users' expressed information for each body part by superimposing that number on the image showing the visual indication of the refining function's result for that body part, for the source users (In the human body display (12) this is the image of the body part in the human body display (12)), or alternatively the human body display (12), in particular, can show the numbers above, the image of the body or body part(s) in the human body display or next to the image of the body shown in the human body display. The human body display (12) can also display each body part in a color based on the numerical result of the refining function applied to the source users' expressed information for that body part (Either the color for the number closest to the average or an "intermediate" color as discussed above) and also display the numerical result itself on the image of the body part.

The screen on a display section (2) or human body display (12) may be a glass display embedded in housing and capable of reading touch input. For example, the screen on a display section (2) or human body display (12) may comprise a capacitive touch screen with a conductor coated over a glass insulator. The screen in a display section (2) or human body display (12) may also be a screen of any of the kinds known in the prior art.

Another example of a display section is a computing system including a specific processor for processing digital data; a memory coupled to the specific processor for storing digital data; an input digitizer coupled to the specific processor for inputting digital data from the pain indicator units connected to the specific processor; an application program stored in the memory and accessible by the specific processor for directing the specific processor's processing of digital data, and a device that displays video coupled to the specific processor and memory for displaying information derived from digital data the specific processor processed. This device that displays video is needed so that summaries of information about the pain felt by user populations, in different body parts, is quickly displayed for viewing.

In some embodiments, a display section (2) or human body display (12) should be able to record, responses that it has received over a period of time in an internal memory, and display how those responses changed during that time period. In the human body display's case, the sections of the displayed body could glow in colors that shows the average pain levels of the responses in sub-periods of the time period(first, the color representing the average pain level of the responses received in one sub-period, then the color representing the average pain level of the responses received in another sub-period, etc.), or the range in which each of those average pain levels falls, or shows the absolute pain levels of the responses that were received at different points in the period of time, or the ranges where those absolute pain levels fall.

A display section (2) or human body display (12) can also be used to show an individual user's reported pain level in one or more body parts over a larger time period by showing how the user's reported pain level in those body parts changed during that time period. For example, the display section (2) or human body display (12) could a) display a human body, representing the user, and b) display the average reported pain level in each body part for sub-periods that are components of the larger time period, by showing each body part in a color that represents the average pain level in that body part during the sub-period. The display section (2) or human body display (12) can then display in succession the user's average reported pain levels in the user's body parts, for each of the sub-periods that make up the larger time period. For example, to view how the user's pain level in several body parts changed over the course of 100 days, the display section (2) or human body display (12) might display the user's average reported pain level in each body part for each of the 100 days, in succession. Then the persons viewing the display will see how the user's pain level in each body part changed over the course of the larger time period (The 100 days).

The display section (2) or human body display (12), in the above example, could also display the user's average reported pain levels in a different way, for example, showing the user's average reported pain levels at 7 P.M. then 8 P.M., then 9 P.M. by calculating the average pain levels the user reported at 7 P.M., then 8 P.M., then 9 P.M. during the 100 days. One way the display section (2) or human body display (12) could do this is by taking the pain levels the user registered at, or closest to, 7 P.M., on each of the 100 days and averaging them, then doing the same concerning the pain levels the user registered at, or closest to, 8 P.M., and the pain levels the user registered at, or closest to, 9 P.M.

The human body display or display section (2) might also include an app database (44), saved on a memory that is part of the human body display or display section (2) respectively, so that the human body display or display section (2) can keep the information it is being sent, about users' source data. The human body display or display section (2) might also include a processor, to make calculations concerning the source data. In some embodiments, the human body display or display section (2) will include a version of an app calculator module (22), which is able to perform the calculations needed to have the human body display or display section (2) show the correct images.

A human body display (12) could also theoretically display an image of a certain individual user, or body part(s) thereof, instead of a "generic" image of a human body, or male or female human body, or part(s) thereof (The human body display would show one of these three things in most embodiments that include a human body display (12)). The human body display (12) could then show display data on, or next to, the image of that individual's body or body parts. This can be used, for example, in cases where the human body display (12) is showing display data based on one source user's source data. The display data can include, but is not limited to, all the display data pertaining to the user that can be displayed on, or next to, a human image on the screen that is a "generic" male or female human image, or part thereof, on a human body display's screen. The image can be scanned from a picture of the source user which is uploaded or otherwise saved into the human body display (12).

A human body display (12) can also theoretically display an image of a part of a human body, instead of all of the human body. For example, a human body display (12) can display the user's teeth, user's head, or the user's mouth.

The human body display (12) is a digital display that shows a digital image of the human body or a part thereof. The image of the human body or part thereof the human body display shows shall be called the "display image" herein. The human body display (12) also shows display data on, or close to, the display image. This display data is based on a) The pain that one or more users have expressed or b) The pain expressed through one or more input devices. The human body display (12) can be operatively connected to one or a group of input devices (including input devices of any kind(s)) and/or pain indicator pieces with pain indicator units and/or pain indicator skins attached. These input devices will feed source data to the human body display.

The human body display will display visual representations of the pain felt by a user or members of a user group, which allows healthcare providers viewing the human body display to learn more about relieving the users' pain and other symptoms, and to observe patterns in the response data. The human body display can mark boundaries between parts of the display image, and can show one or more pieces of the display data on or next to the part of the display image to which that piece of display data pertains. Some examples of statistics that are display data are: A. The source users population's average pain level in each of their body parts during the last timestretch, or B. The source user population's average nominated pain level in each of their body parts averaged over the source users' nominating periods for a set amount of time in the past (Such as the past 24 hours with a nominating period of 1 hour), or C. The source users' average nominated pain level in each of their body parts averaged over the past 48 hours. Some ways of showing, as display data, the amount of pain, or average amount of pain, or a statistic representing some other function of the amounts of pain that the source user population has felt (such as the median or mode of the nominated pain levels over a certain time period), are A. Through a number representing the statistic being displayed on the relevant body part to which the statistic applies (Such as the median nominated pain level in users' right knees being displayed on the right knee in the image of a human on the human body display), or B. Through the relevant body part glowing in a certain color, where the color changes as the refining function's result concerning the user population's expressed information or a category thereof varies. Multiple ways that the color could change as the users' registered responses changes are discussed elsewhere in this application.

In some embodiments, the healthcare personnel or other users viewing the human body display can select what information they want the human body display to show, on, or close to, each part of the image of the human being displayed, by manipulating the 7 parameters.

In some embodiments, if the display section (2) or human body display (12) is receiving input from one or more input devices, and the viewer has commanded it to apply the refining function to input from some of these input devices that fit criteria the viewer defined, the human body display will search through the input it is receiving, from all input devices, to find the ones that fit the criteria the viewer entered. Then the human body display will apply the refining function to the input is receiving from these input devices.

This is one of the ways that the display section (2) or human body display (12) can be used to analyze a group of users' pain patterns when the users' user IDs are not known.

A viewer might also arrange for certain users to use certain input devices (For example, if the input devices' device IDs fit a pattern, distributing the input devices in a sequence so that the viewer can know the device ID number of the Xth device in the sequence and know which user was given that input device) and then select the input devices which are the source data's sources, knowing which users are using those input devices.

If the viewer wants to apply the refining function to source data from specified input units that is stored in one of the databases, the display section (2) or human body display (12) can look through the Centralized Integrated Database, or any available app database, to find expressed information that came from the specified input units and fit any other criteria the viewer designated. The display section (2) or human body display (12) can then apply the refining function to this expressed information or, if the viewer desires, a subgroup thereof. This approach can also work when the viewer has access to information about which user used which input device.

In some embodiments, if the display section (2) or human body display (12) is receiving input from one or more input devices, where the user ID of the user using each input device is accessible to the display section (2) or human body display (12), and the viewer has commanded the display section (2) or human body display (12) to apply the refining function to input from some of these users that fit the criteria the viewer defined, the display section or human body display can search through the centralized integrated database (10) for expressed information and individual information made by the users using the input devices sending input to the display section (2) or human body display (12), and will search through those users' individual information and expressed information, in the centralized integrated database (10) if needed, to find the users who fit the criteria the viewer defined, and apply the refining function to source data from those users. The criteria the user defined could be, for example, users who have certain words appearing in their individual information within a specified length of time before the present, or users of a certain age, or users of a certain gender.

In some embodiments, if the viewer commands the display section (2) or human body display (12) to use source data from a defined user or user group the viewer defined, expressed during a previous time period, the display section (2) or human body display (12) will search through its own app database (44) or the centralized integrated database (10) to find responses by that user or users who fit the criteria the viewer defined, respectively, and then apply the refining function to the source data from that user or users. The display section (2) or human body display (12) may download and save source data that it found in the centralized integrated database (10) in an app database saved within the display section (2) or human body display (12).

In some embodiments, if the display section (2) or human body display (12) has to retrieve data from the centralized integrated database or a specialized database, the display section (2) or human body display (12) may directly or indirectly communicate with the centralized calculation module (28), which will find the desired data by searching through the centralized integrated database or a specialized database, respectively, and send the desired data to the display section (2) or human body display (12).

In some embodiments, if the display section (2) or human body display (12) has to apply the refining function to source data being presently transmitted to it, and also to source data in Databases, the display section (2) or human body display (12) will directly or indirectly retrieve the source data located in the Databases and then apply the refining function to the retrieved source data and the data being presently transmitted to the display section (2) or human body display (12).

In many embodiments, the processor in the human body display is programmed with, or connected to a memory which includes, a list of colors that represent different pain levels on the pain scale being used.

The display section (2) and human body display (12) can allow a viewer, such as a member of a team caring for multiple people, to quickly view summaries and trends relating to the pain levels in different body parts that a population of users have experienced in a certain time period or group of time periods, by creating a refining function that focuses on information the user desires and applying the refining function to source data from the user population or subgroups thereof. This can be useful for understanding the users' health, and what is causing the users' pain, and how to relieve the users' pain and other symptoms. It can also help the viewer to get insights about how the users' health conditions are changing and, if the health conditions were expected to improve, whether they are improving at any rate that was expected, and to understand information about the user's recovery from any health conditions. It can also help the viewer to get insights about how and why a user group's health conditions are changing relative to those of another user group. This may help the viewer discover methods of helping users' health conditions to positively change, and also discover ways to reduce the areas under users' pain lines.

A viewer can also quickly visually see how user groups' registered responses are different from each other, or have different trends from each other, by causing the display section (2) or human body display (12) to show display data for one group and then another. The viewer might therefore be able to figure out why the user groups' registered responses are different, and use this information to make recommendations that reduce the user group members' pain levels or otherwise help their health.

The display section (2) and human body display (12) can also allow a viewer, to quickly view summaries of, and trends concerning, the pain levels that a single user has experienced in a certain time period or group of time periods in different body parts. This can be useful or understanding the user's health, and what is causing the user's pain, and how to relieve the user's pain and other symptoms, and understanding information about the user's recovery from any health conditions. It can also help the viewer to get insights about how the user's health conditions are changing and, if the user's health conditions were expected to improve, whether they are improving at any rate that was expected. It can also help the viewer to get insights about how and why the user's health conditions are changing relative to those of another user. This may help the viewer discover methods of helping the user's health conditions to postively change, and also discover ways to reduce the areas under the user's pain lines.

A viewer can also learn more information about an individual's recovery from surgery, or groups of surgical patients' recovery from surgery, using the display section or human body display. The viewer can see trends in the pain an individual user experienced. The viewer can also learn whether the pain an individual user experienced is "different from what is expected" for users in a similar situation (such as users who experienced the same health condition), and, if the pain the individual user experienced is, in fact, "different from what is expected", the viewer may be able to try to find out why the differences exist, and create a strategy for helping the individual user.

The viewer can also quickly, visually, compare the pain experienced by different user group who underwent the same surgery under different conditions (Such as through use of different surgical techniques, or using different anesthetics), and notice which user group experienced less pain, or statistically significant lower pain levels, during their recoveries. The viewer would compare the pain the two groups experienced by using the display section (2) or human body display (12) to view the results of the refining function applied to one group's source data and then viewing the results of the same refining function being applied to the other group's source data. The viewer can then use this information to design, use, and select better surgical techniques that involve less painful recoveries. One way for a viewer to do this is by comparing the pain patterns of a user population, that has as a registered event a surgery, which used a surgical technique, and another user population, that has as a registered event the same surgery, but using a different surgical technique, and seeing which group has a lower pain distribution.

A viewer can also quickly visually see how individual users' registered responses are different, by causing the display section (2) or human body display (12) to show display data for one individual and then another individual, using the same refining function. The viewer might therefore be able to figure out why the users' registered responses are different. The user can also clearly, quickly, observe how a single user's registered responses differed between time periods, which may help the viewer learn why the user's registered responses differed between time periods.

In some of the display section (2)'s and human body display (12)'s embodiments, shades of gray or patterns can be used instead of colors to represent different pain levels.

An alarm light (3) is a light that "turns on" and makes light and/or flashes when a signal is received by, depending on the embodiment, the alarm light or a receiver operatively connected to the alarm light, and the signal says that the user has activated a pain indicator unit. In some embodiments, the alarm light will make light or flash when the alarm light or a receiver operatively connected thereto receives a signal that a user has activated a pain indicator piece or virtual pain indicator button. The alarm light can also be designed, using methods known in the prior art, to turn on and/or flash in different colors, depending on how strongly the user has activated the pain indicator unit or other indicating part. For example, when the user activates a pain indicator unit to a low degree, an alarm light on a dentist's desk may turn on and glow yellow, but the alarm light may be designed to glow red when the user activates the pain indicator unit to a high degree. An alarm light (3) can also be a group of lights, for example, a row of lights where each light represents a different patient, or a patient located in a different place, and flashes when that patient activates pain indicator unit.

The server (4) is a computer server, as known in the prior art. The server may be implemented as a conventional computer system, an embedded controller, a laptop, a server, a mobile device, a smartphone, a set-top box, over-the-top content TV ("OTT TV"), Internet Protocol television ("IPTV"), a kiosk, one or more processors associated with a display, a customized machine, any other hardware platform and/or combinations thereof.

The receiver (5) is a machine that can receive wireless signals from a transmitter.

A battery charger (6) is a charger for one or more of the batteries for those components of the invention that use electricity. A battery charger can use wires or be wireless. A battery charger may sometimes be connected to a solar panel. Charging ports are included in "battery chargers" here.

A solar panel (7) is one of any of the variations of solar panels, that are known in the prior art. A solar panel can be attached to one of the invention's components, to directly or indirectly provide electrical power for some of the invention's electronic components. For example, a solar panel can be attached to a human body model, to provide power to the pain indicator units (1) on that human body model. A solar panel can also be attached to a battery. The solar panel in that case can be connected to each of the pain indicator units to provide power to them.

A mouth model (8) is a model of a human mouth, preferably including models of all the teeth. Pain indicator units can be placed on the mouth model, so that a user can activate one of the pain indicator units to indicate that he/she is experiencing pain in the area of his/her mouth which corresponds to the area of the mouth model where that pain indicator unit is placed.

Orthodontists sometimes create molds of their patients' mouths. A mouth model can theoretically be made that corresponds to a specific patient's mouth, or can be made to represent mouths in general.

Alternatively, parts of the mouth model may be made of somewhat flexible material, with parts that are moveable, but with the parts imitating the teeth made out of a harder substance such as metal or a hard plastic.

This way, a user or dentist could move the mouth model's parts to approximate the shape of a specific person's mouth. For example, parts of the mouth model could be made out of a flexible material such as clay or Composi-Mold, alginate, through an "alginate impression", using polyvinylsiloxane, using dental putty, using a stone mixture, or a plaster mixture, or polyvinyl siloxane, or the other materials of which orthodontists or dentists build molds.

Parts of the mouth model could also be made out of rope, to allow components of the mouth model to be moved around to approximate the shape of a specific person's mouth.

Other methods of making the parts of the mouth model flexible are known in the prior art.

A mouth model customized to a specific person's mouth, with the locations of features like teeth customized to that person, might be more useful than a regular mouth model in some circumstances. The locations of the nerves and blood vessels in the mouth of each person (and therefore the pain sensitivity of different areas of that person's mouth) are influenced by locations of other features in that person's mouth (such as teeth to which the nerves connect). Locations of nerves, blood vessels, and other features in a specific person's mouth influences the pain sensitivity of areas of that person's mouth. Therefore, it might be possible to get more accurate information about a specific person's experience of pain in different areas of their mouth by using a customized mouth model.

A mouth model, especially a flexible mouth model, may also include a first position sensor at a pre-defined point, such as the center of the back of the mouth model, and other position sensors scattered around the mouth model. The other position sensors will determine their distance from the first position sensor at the pre-defined point, and from each other, to create an understanding of where the mouth model's components, such as models of teeth, and pain indicator units, are located. Here, each pain indicator's location unit relative to at least one position sensor should be programmed, and preferably programmed into one or more position sensors. Then, when the user activates a pain indicator unit, there will be information about where the pain indicator unit is, and where the part of the user's mouth to which the pain indicator unit is attached is located. The activated pain indicator unit's position relative to at least one position sensor will be known, and all position sensors' positions relative to the first position sensor will be known. Each position sensor may be attached to a pain indicator unit.

The mouth model can also have position sensors scattered around the mouth model that communicate their relative locations to each other. Here, the location of each pain indicator unit relative to at least one position sensor should be programmed, and preferably programmed into one or more position sensors. For example, "position sensor X" can be programmed that "pain indicator unit A" is located 1 cm away from it, or located next to it.

A human body model (9) is a model which looks like a human body, and which has pain indicator units (1) and/or a pain indicator skin (43) on it. The user can activate the pain indicator units or parts of the pain indicator skin (43) to indicate when and where the user is feeling pain. In principle, a human body model (9) can be made to look like the body of a specific person, and "customized", or made to resemble a "generalized" model of a human body. A human body model (9) can also be made that represents a generalized male or female body.

A human body model (9) can also have multiple components (These are considered part models herein) in which it can be divided. For example, a human body model (9) can have, as components, part models that represent the right arm and left arm, and part models that represent the chest's upper half and lower halves, and part models that represent the abdomen's upper and lower halves. Each of these part models can include one or more pain indicator units and/or a pain indicator skin.

In some variations of the human body model (9), the human body model, or parts thereof, will include alarm lights that glow in different colors, and/or intensities, with the color and/or intensities depending on how hard the user is activating the pain indicator unit(s) and/or pain indicator skin.

In some embodiments, the specific pain indicator unit, part model or part of the pain indicator skin that the user is activating may glow in the color and/or intensity that reflects how hard the user is activating the pain indicator unit(s) and/or pain indicator skin. Whether all or part of the human body model, pain indicator unit, or pain indicator skin glows in a certain color or intensity depending on how hard the user activates it, this helps the user calibrate how hard the user wants to activate the pain indicator unit(s) or pain indicator skin, to express the pain degree the user is feeling. This also helps the user, and others, to observe how much pain the user is feeling, and the location where the user is feeling pain.

The centralized integrated database (10) is a database which combines all the registered responses from multiple users, preferably a very large number of users or all users. The centralized integrated database should also include the individual information that users entered when they estab- lished their individual databases. This individual informa- tion can include the ages, genders and ethnicities of indi- vidual users, and other individual information concerning individual users. The centralized integrated database (10) preferably also records as many as possible of the dental/ medical procedures performed on these users, and other conditions, including health conditions, that the users have experienced. This is a form of individual information. This individual information can be imported into the centralized integrated database through a variety of methods in different embodiments. For example, in some embodiments the user can import them through a calendar app or a spreadsheet. In some embodiments the user can also import the individual information using the Iforms method of Rossi et. Al. In some embodiments, the user can also manually import the indi- vidual information into the centralized integrated database, or enter it manually, and/or a healthcare provider can import the individual information into the centralized integrated database, or enter it manually. In all cases, the user may also import this individual information into the user's individual database or a specialized database or app database and then cause the information to be copied to the centralized inte- grated database. Any method of importing the user's indi- vidual information into the centralized integrated database that is part of the prior art is explicitly part of the present invention. The centralized integrated database (10), in some embodiments, will also include records of the users" expressed information, with a minimum expressed informa- tion duration for each entry, from the times the users were expressing information but not registering responses. Sta- tistical analysis can be performed on the registered responses and/or expressed information from multiple users, to find ways of possibly reducing the pain that users expe- rience in the future.

The centralized integrated database (10) can also be constructed in any way known in the prior art, Some ways of constructing it are discussed below.

For example, in some embodiments of the centralized integrated database (10), one or more columns in the cen- tralized integrated database will include users' individual information. Individual information about the user's health conditions, and the date and time that the user started having each health condition (Or alternatively, the date and time the user was first recorded themselves as having the health condition in the centralized integrated database) will also be in one or more columns. Other information related to the user's health conditions, such as surgical techniques used for operations, operations and treatments that the user under- went, and drugs used, would also be recorded with the health conditions themselves. The health conditions might be des- ignated by name, with the names of each of the user's known health conditions and the other information above entered into the columns, pertaining to "health conditions". The user's expressed information, including registered responses, could be in entries in other columns relating to pain in body parts, along with the time to which each entry pertained. Environmental information, including informa- tion about the weather for each time period, in the user's location, will be entries in one or more other columns.

In some embodiments, the information about each health condition and the time the health condition was first entered in the centralized integrated database (11) will appear in the columns as part of every entry pertaining to a user after the first entry where it appears. In some embodiments, the health condition and the time the health condition was first entered into the centralized integrated database will appear only in the entry where they are first entered into the centralized integrated database. In some embodiments, the user can, through the remote program, directly or indirectly command the centralized integrated database to have the health con- dition and time not entered into entries in the centralized integrated database after the user considers the health con- dition to be ended. The health condition will still appear in entries where it appeared before the user made the com- mand. Other configurations of when the health condition appears in entries in the centralized integrated database are possible.

In some versions of the centralized integrated database (10), each user's activating a pain indicator unit (Such as by pressing the pain indicator unit if it is a button), or activating a pain indicator skin, or virtual pain indicator unit will generate a new entry in the centralized integrated database (10). The entry can have the minimum response duration allowed in that embodiment, or, if the user activates the pain indicator unit for longer, more entries, each with minimum response duration and including the pain level the user registered, can be recorded. In some other versions of the centralized integrated database (10), an entry will also be generated each time a user who expresses information, for each minimum duration period for expressing information. The entries that include an indication(s) of pain will include the location(s), degree(s) and kind(s) of any pain that the user registered as part of a registered response. If the user did not register a response, the entry will say that the user registered no pain in that minimum duration period.

In some versions of the centralized integrated database, a user's responses can be entered into the centralized inte- grated database without individual identifiers (Such as user IDs) for those users. This limits the amount of analysis that can be done using users' expressed information. However, a lot of analysis can still be done. For example, relations between environmental information and pain levels can still be explored. Relationships between the users' pain patterns after a medical or dental procedure and events that happened during the medical or dental procedure could also potentially be explored if information about the procedure itself, the events that happened during the procedure, and the time and date the procedure happened, are recorded in the centralized integrated database (10) as individual information.

In some embodiments, the registered responses broadcast or transmitted from input devices will not include any individual information beyond the user ID of the user using the input device. Other individual information will be in the user's individual database and the central integrated data- base.

In some embodiments, searching for certain types of individual information, such as the names of health condi- tions, can be done by text searching in the databases.

In some embodiments of the centralized integrated data- base, and specialized databases a user's user ID and (if saved in the centralized integrated database) name will not be accessible without the user's explicit permission to other parties who are attempting to use the centralized integrated database or specialized database. Likewise, in some other embodiments of the centralized integrated database, or spe- cialized database, some or all of users' other individual information is unavailable without the user's explicit per- mission to these other parties. And in other versions of the centralized integrated database and specialized databases, users will have the right to "opt out" of any of their information, including their expressed information, being accessed by these other parties. In some embodiments, a user could "opt out" by using that user's remote program (20) to communicate that the user has "opted out" to the centralized integrated database.

In some embodiments, the centralized integrated database will "update" regularly with new information in each user's individual database (Unless that user has decided to "opt out" of such updates, in some embodiments), and each user's individual database will update regularly with new information pertaining to that user in the centralized integrated database.

In some of the centralized integrated database's versions, available environmental information for the geographic area where the user was located when they made each response will also be entered into the centralized integrated database with that response.

The individual database (11) is a database in some embodiments of the invention where an individual user's responses can be logged, along with the degree(s), location(s), and type(s) of the user's pain, if registered. In one embodiment, the individual user's responses can be logged with the time and date of each response in one column, and the intensity, etc. of the response in other columns. In some embodiments the same information, pertaining to each individual user, is recorded in that user's individual database, as is recorded, pertaining to that user, in the centralized integrated database. The same information, pertaining to the individual user, can be recorded in each column in the individual database as is recorded pertaining to that individual user in the centralized integrated database (10).

The suction cup (13) is a suction cup that can be attached to one of the invention's other components, such as a mouth model or human body model, to hold the other component firmly in a place desired by the user.

An alarm (14) is an alarm that sounds when a user activates a pain indicator unit.

The transmitter (15) is a machine that can send signals wirelessly.

A coordination module (16) is a computer program that coordinates the sounds made by the alarms triggered by the different pain indicator units in a group, and the visual displays the alarm lights triggered by the different pain indicator units in that group make. For example, the coordination module might be in communication with a group of four pain indicator units, in different hospital rooms, where each pain indicator unit is capable of making five different sounds and flash in five different colors. For example, the coordination module might be programmed to have the alarm triggered by one pain indicator unit make a buzzing sound, the alarm triggered by a second pain indicator unit make a ringing sound, the alarm triggered by a third make a ringing sound and also the alarm light the third triggers makes a green flash, and the alarm light triggered by a fourth make a red flash. The coordination module can also give indications on users' cell phones in some embodiments. The coordination module can be a program or a part of another program. A coordination module that is part of the remote program (20) is an app coordination module. In some embodiments, a coordination module (16) can be programmed on a specialized electronic instrument. The coordination module (16) may ensure that the different pain indicator units that it is instructing make different auditory or visual signals when activated, using any method known in the prior art. In some embodiments, a coordination module (16) can use the wireless broadcast and reception capabilities of the device running the coordination module (16) to communicate with a group of input devices, and select which sound the alarm on each input device the coordination module is instructing should make, and/or the visual signals that the alarm light on each input device the coordination module is instructing should make, when communicating that a user is using that input device to indicate that the user is feeling pain above a certain level. The coordination module (16) may use the following method: Some kinds of input devices, when manufactured, will include a processor, a receiver, a transmitter, one or more alarms, and/or one or more alarm lights. The processor will be programmed with a list of sounds that the alarm (If the input device includes an alarm) is capable of making, and a list of visual signals the alarm light (If the input device includes an alarm light) can make, and the input device's device ID. The processor (29) in each input device will also be able to pick which of these sounds any alarm in that input device will make, when activated, and which of these visual signals any alarm light in that input device will make, when activated. When a coordination module is used with these input devices, the device running the coordination module will establish communications with the processors in the input devices which the coordination module is instructing. Some ways (Not the only possible ways) to do this are A. The transmitter in the input device will broadcast a signal, which the device on which the coordination module (16) is running receives, and then the coordination module (16) will directly or indirectly wirelessly transmit instructions to the receiver in the input device, which will then transmit the instructions to the processor (29) in the input device, or B. The coordination module (16) will cause the device on which the coordination module (16) is running to broadcast a signal, and the receiver in the input device receives this signal, and then communicates the signal to the input device's processor. The processor will then cause the input device's transmitter to broadcast a signal, which the device running the coordination module (16) receives.

The input device's processor will transmit the input device's device ID, list of sounds that the alarm (If the input device includes an alarm) is capable of making, and a list of visual signals the alarm light (If the input device includes an alarm light) can make, to the input device's transmitter, which will broadcast this information, so that the coordination module (16) receives it. The coordination module will then examine the device IDs of the input devices that it is instructing, and the sounds and visual signal(s) that the components of each of these input devices is capable of making, and the coordination module will select a different sound for the alarm in each input device to make, out of those which the alarm is capable of making, and a different visual signal for the alarm light in each input device to make, out of those which the alarm light is capable of making. The coordination module (16) will cause the device on which it is running to broadcast signals specifying the device ID of each input device the coordination module (16) is instructing, the sound any alarm in each input device that the coordination module (16) is instructing should make if one of the pain indicator units in that input device is activated, and the visual signal any alarm light in each input device that the coordination module (16) is instructing should make if one of the pain indicator units in that input device is activated.

The input devices do not all need to be of the same type. Input devices of multiple types, that are capable of transmitting the relevant information, can be used with the coordination module in the way discussed above.

A part model (17) is a model of another part of a person's body that is not the person's mouth, and which has pain indicator units (11) attached. For example, a part model (17) can be a model of a person's hand or foot. A part model can also be a model of one of the user's organs, such as the user's heart, or gall-bladder, or a model of a nondiscrete part of a person's body, such as the upper area of the person's chest. Like the mouth model or human body model, a part model (17) can be crafted to resemble a part of a specific person, or can be crafted to represent a generalized version of that part. For example, a part model of a hand can be crafted to resemble a specific person's hand, or to resemble a generalized version of a human hand.

One example of a part model can be a model of a head, with pain indicator units on different points on the head that a user can activate to show to show which areas of the user's head are hurting when he/she is experiencing a headache. The user would activate pain indicator units that are in the areas of the model of the head that correspond to the areas of the user's head where the user is feeling pain.

A part model can also theoretically have several pieces, where each piece has one or more pain indicator units on it, and where the pieces can be disconnected from each other. For example, a part model of a head can have several parts, each of which has pain indicator units on parts which correspond to the inside of the head and the surface of the head. The user can then take the head part model's pieces apart and activate the pain indicator units to indicate where he/she is feeling pain, on the user's head's inside or surface.

The components of a part model may be designed so that responses registered on each part of a part model may have markers to indicate the parts of the body to which those responses apply, or be otherwise programmed so that responses registered on each part of a pail model indicate the parts of the body to which those responses apply.

A memory (18) is a computer memory, including, but not limited to, all types of computer memory known in the prior art, including, but not limited to, hard drives and zip drives.

A position sensor (19) is an instrument that (wirelessly or otherwise) transmits signals that allow other position sensors (19) to detect how far away they are from that position sensor (the "first position sensor"). Both the first position sensor and the other position sensor will broadcast additional (wireless or otherwise) signals indicating this distance. As the distance between the first position sensor and the other position sensor changes, both position sensors will detect the new distance between them. Therefore it will be possible to form an approximate picture of the locations of a group of position sensors relative to each other by noting the distance from each first position sensor in the group to each other position sensor in the group.

In some embodiments of the invention, the position sensors can each communicate with a nearby processor, with wireless signals, so that the processor is able to tell how close each of the position sensors is to that processor. The position sensors' locations relative to each other can be determined from this.

The remote program (20) is a program that can be run on a healthcare provider's cellular phone or another instrument such as a desktop computer. Hereafter, cellular phones, personal computers, "I-pads", and other devices or combinations of devices capable of running the remote program and using the app display module (25) to display the information the app display module is designed to display shall be collectively called, simply, "PCs". Some versions of the remote program can also be run on an individual user's PC.

The Battery (21) is a battery that can provide electrical power to the parts of the invention to which it is directly or indirectly connected. The battery can be a lithium battery or another kind of battery.

The app calculation module (22) is a module of the remote program (20) that performs statistical calculations on the information that the app receiving module (24) has received from users, and the app calculation module (22) passes some or all of the results on to the app display module. In some embodiments, the app calculation module will only perform statistical calculations for the specific user who is using the app calculation module. The App calculation module runninor on each PC, in other embodiments, will only perform statistical calculations for the patients/users whose information that particular copy of the remote program, of which that particular app calculation module was a part, was authorized to receive. In other embodiments, the app calculation module (22) will also be able to access the individual database (11) of the user who is using the app calculaticrn module, and in other embodiments the app calculation module will be able to access the individual databases of those users who, using their remote programs, gave permission for this access to the user. In other embodiments, the app calculation module (22) will also be able to access the centralized integrated database (10), and specialized databases (33), perform statistical calculations on the information in those databases, and pass some or all of the results on to the app display module for the user to view. In some embodiments, the app calculation module can do this automatically, and pass the results to the app display module for the user to view. In some embodiments, the app calculation module can do this at the user's request, and pass the results to the app display module for the user to view.

The app calculation module in some embodiments of the invention can, for example, view the information received from each user as a series of chronological entries in a table, with each entry including information for the date, time, gender, age, and health conditions the patient experienced, potentially along with other individual information such as the patient's race and other individual information discussed herein. Entries in the table can include the user's expressed information, such as responses showing the existence, and, if available, intensity, duration, kind, and location of pain experienced by each user at a particular time. The location(s) of pain, in each response is based on which pain indicator unit(s), and/or virtual pain indicator units on an input device, the user has activated.

The app calculation module may in some embodiments of the invention be able to create graphs concerning the responses the app calculation module examined. These graphs can include bar graphs showing how responses fell into different categories (such as responses that fell into certain time periods or pain levels). These graphs in some embodiments can also include histograms of when users experienced pain, the number of users in a user population that experienced pain of each of multiple groups of levels, and other kinds of histograms. These graphs in some embodiments can also include line graphs showing the pain level a user is reporting in a body part, on the Y axis, and time, on the X axis. The line made by the user's reported pain level at each point in time in a body part can be a "pain line" for that body part, for that user. The "area under" the pain line can be computed, in the same way the area under a line can be computed in 2-dimensional line graphs of other types.

These graphs in some embodiments can also include graphs in 3 dimensions, with the pain level reported in one body part on the Y axis, pain level reported in another body part on the Z axis, and time on the X axis. The app calculation module, in some embodiments, can also plot the coordinates indicating the user's pain level in more than two body parts, as follows: By calculating a hypothetical "graph" where time is the X axis and other axes represent the user's reported pain level in multiple other body parts. The app calculation module can also, in some embodiments, calculate the kurtosis of a group of responses. This can be useful in analyzing the significance of responses. For example, it can be useful in deciding whether the mean of a subgroup of the responses in the group is far enough away from the mean of the responses in the group to warrant further examination. It can also be useful in deciding whether a single response is far enough away from the group's mean to warrant warnings and other further measures.

Some of the statistical calculations that the app calculation module is able to apply to the dataset that it is analyzing, or the nominated pain levels based on that dataset, in some of the invention's embodiments, are: Finding the median, mode and mean of the responses in the dataset or the nominated pain levels based on responses in the dataset, and finding percentiles of the responses in the dataset or the nominated pain levels based on responses in the dataset (Such as the uppermost 5% of the registered responses in the dataset). The app calculation module, in some embodiments, can also calculate the skewness of a distribution of registered responses, so that the user can understand the distribution better, and how the distribution might relate to the user's individual information and the environmental variable values the user experienced.

The app calculation module (22), in some embodiments, can also apply a nominating rule, that the app calculation module's user picked using the app calculation module, to the data in some or all of the app database(s), the specialized database(s), and the centralized integrated database, and individual database(s). The app calculation module can then perform statistical analyses and create graphs using the nominated pain levels that the app calculation module picked through using the nominating rule. Every type of graphing, or statistical technique, that the app calculation module can perform upon expressed information, or registered responses, the app calculation module can also perform upon a dataset comprised of nominated pain levels, using a nominating period and nominating rule the user selected using the app calculation module (22).

Depending on the amount of computing power and memory available to the app calculation module (22), the app calculation module can, in some embodiments, perform some (or all, if sufficient computing power and memory is available) of the statistical and graphing functions listed below that the centralized calculation module (28) is able to perform.

The app calculation module can also, in some embodiments, apply a refining function to source data drawn from a group(s) of users, and also apply parameters A-G to get a better understanding of a group of user's pain patterns, or an individual user's pain patterns. The complexity of a refining function that can be applied by an individual copy of the app calculation module depends on the amount of computing power and memory available to that app calculation module.

A healthcare provider can also use the app calculation module (22) to provide more "personalized" service to users as follows: If a user gives a healthcare provider access to the user's individual database, the healthcare provider is able to use its app calculation module (22) to examine whether the pain the user is feeling is "out of the ordinary" for that user, or dangerous. The healthcare provider can use its app calculation module (22) to chart the user's current pain pattern versus the user's pain patterns for other time periods that were recorded in the user's individual database, by a. accessing the user's individual database (10) and b. doing charting and statistical analysis of the user's pain pattern and categories of the user's expressed information in a recent time period vs. the user's pain patterns and the user's expressed information categories in previous time periods. The app calculation module (22) can also take a category of the user's expressed information, such as the user's registered responses relating to one body part, and do statistical analysis on the category. The results of the statistical analysis, including any graphs created by the app calculation module, can be sent to the app display module for the user to view.

For example, the healthcare provider can use its app calculation module to calculate distributions of the amount of pain the user feels in different body parts, during defined lengths of time after events in the user's calendar that the user has imported into the user's individual database. Then the app calculation module can calculate whether the user's pain, in different body parts, is particularly high after one such event, for example, whether the user's pain level in some body parts is in a particularly high percentile of the user's pain distribution after similar events. The app calculation module can do this by retrieving the user's registered responses after similar events from the user's individual database, and calculating whether the user's pain levels in the body parts in question are in an exceptionally high percentile of the user's pain levels the same length of time after similar events. Then the healthcare provider might inform the user of this, and, if justified, warn the user of any concerns that the healthcare provider has about the user's health. This warning may take an automated form, such as a text message that the user's pain levels are particularly high after a single such event.

As an illustrative but nonexclusive example, the healthcare provider can use its app calculation module to calculate distributions of the user's pain 1 hour after a physical therapy session, 2 hours after a physical therapy session, etc. The app calculation module will retrieve the user's registered responses 1 hour after previous physical therapy sessions, 2 hours after, etc. from the user's individual database, and compare them with the user's registered pain levels 1 hour after the user's most recent physical therapy session, 2 hours after, etc. In this example, if the user's pain level in the user's chest 1 hour after the physical therapy session is in what the app calculation module estimates is the distribution of pain 1 hour after the physical therapy session's $97^{th}$ percentile, and the app calculation module estimates that the user's pain level in the user's chest 2 hours after the physical therapy session is in what the app calculation module estimates is the distribution of pain 2 hours after the physical therapy session's $95^{th}$ percentile, the healthcare provider can send the warning to the user, if the healthcare provider's policy is to send a warning to a user if the user's pain level in the user's chest 1 hour, and 2 hours after a physical therapy session is in or above the $95^{th}$ percent of the user's pain levels in the user's chest 1 hour, and 2 hours, respectively, after physical therapy sessions in general.

A healthcare provider might also program its remote program (20) to send the healthcare provider alerts when any of a series of indicators in any of multiple users' pain patterns goes above a certain level. Then, the healthcare provider can inform the user that something could be wrong and the user should work with the healthcare provider to do something about it. An example is a primary care doctor, who has access to a patient/user's individual database, programming the primary care doctor's remote program to send the primary care doctor an alert whenever a certain patient/user's average nominated pain level in the patient/user's chest goes above a certain level, that the doctor has picked. This might be an indication of something seriously wrong with the patient/user's heart or lungs.

A concerned user with a relative who is sick, or in a hospital, can also use the invention as follows. First, the sick relative would give the concerned user access to their individual database. Then, the concerned user would use their app calculation module to calculate the sick relative's pain distributions in different body parts. The concerned user could also program their app calculation module to a. Access the sick relative's individual database (10) and b. Do charting and statistical analysis of the sick relative's pain patterns. Then the concerned user can program their remote program to send the concerned user an alert when the sick relative's average nominated pain level in a certain body part(s) during a certain time period goes above a certain level, or goes above a certain percentile of the distribution of the sick relative's pain in that body part(s). Then the concerned user could visit the sick relative on occasions when either or both of these types of events happens. Such events will be occasions when the user's pain levels in that body part(s) will be higher.

This will help individual understand their pain patterns better, and also better understand warning signs of serious conditions, and how to reduce the amount of pain they feel.

Users can also gradually "optimize" their lives to experience less pain, as follows: First, a user can find which activities, for that user, correlate to a decrease in the amount of pain the user feels, even if the decrease is not much. One way would be to find which activities, for that user, reduce the areas under the user's pain lines in later time periods. Then, the user can start performing these activities more, and, while continuing to perform those activities more, the user can find what other activities correlate to further reduced pain levels, such as further reduced areas under the user's pain lines. Then the user can start performing these other activities more, and continue to improve. Eventually the user might be able to achieve a very significant reduction in the areas under the user's pain lines, and the user's pain shape, which would substantially improve the user's quality of life.

The app calculation module, in some embodiments, will be able to use Bayesian analysis to find the probability of a user experiencing events in the future by a) Taking records of these events from the user's individual database. b) Noting the pain patterns the user registered before these events happened. c) Calculating the posterior probability of these events happening after the user experienced these pain patterns. d) Monitoring the user's current pain patterns to find whether any of them are similar to the user's pain patterns which happened before the event in question. e. Alerting the user if the posterior probability of one of these events happening is higher than a certain threshold.

In some embodiments, the app calculation module can access the centralized integrated database and perform a Bayesian analysis, by taking records of events and registered responses from the centralized integrated database, instead of an individual database.

Other techniques, related to Bayesian analysis, that users can also use the app calculation module to execute in some embodiments are maximum likelihood estimators, Bayes estimators, method of moments estimators, Cramer-Rao bound, minimum mean squared error (also known as Bayes least squared error), maximum a posteriori, minimum variance unbiased estimator, best linear unbiased estimator, unbiased estimators, particle filter, Markov chain Monte Carlo, Kalman filter, Ensemble Kalman filter, and Wiener filter.

In some embodiments, the app calculation module can also calculate the user's pain lines, and pain shape, based on the registered responses in the user's individual database.

A healthcare provider who is also an individual healthcare practitioner can also use the app calculation module to give more customized help to the healthcare provider's patients in the following way: First, a group of the healthcare provider's patients will give the healthcare provider access to their individual databases. The group might, but does have to be, small. Then, the healthcare provider can give itself an alert, to contact one of the users in the group, when that user's pain levels increase by a certain amount or reach a certain level (chosen by the healthcare provider).

The healthcare provider can also create a group, to perform statistical analysis on, out of the healthcare provider's patients, who gave the healthcare provider access to their individual databases. The group's members need not have anything in common; The healthcare provider can manually add the group members' user IDs to the group. The healthcare provider can use the app calculation module to perform statistical analysis and create graphs on the registered responses of the small group of the healthcare provider's patients, as a group, to see if there is anything about their pain patterns that the healthcare provider can use to gain insights into their conditions, and to get "early warnings" in the form of alerts when the pain levels of an exceptionally high percentage of the group's members are increased more than a certain amount. Once the healthcare provider knows this increase is happening, the healthcare provider may contact the group's members, send preemptive recommendations to them, or take other measures.

Individual healthcare providers may also use this method to find and discover highly localized healthcare issues, such as issues affecting a single neighborhood.

A healthcare provider could also theoretically work with the healthcare provider's patients (who will be users) to find measures and activities to reduce the average area under the group of users' pain lines, and the volume in the group of users' pain shapes.

The app calculation module can also calculate standard deviation of a group of registered responses, and can calculate the weighted mean of a group of registered responses, in some embodiments, and send the results to the app display module for display to the user.

The app calculation module (22) can also fit distributions to registered response data, including log normal and exponential distributions, and other distributions, in some embodiments, and send the results to the app display module for display to the user.

The app coordination module (23) is a module of the remote program (20) that coordinates the sounds the alarms triggered by the different pain indicator units in a group (Or pain indicator units on different input devices in a group) make, and the visual displays the alarm lights triggered by the different pain indicator units in that group (Or pain indicator units on different input devices in a group) make. For example, the app coordination module might be in communication with a group of four pain indicator units, in different hospital rooms, where each pain indicator unit is capable of making five different sounds and flash in five different colors. The app coordination module can select for the alarm triggered by one pain indicator unit to make a buzzing sound, the alarm triggered by a second pain indicator unit make a ringing sound, the alarm triggered by a third makes a ringing sound and also the alarm light the third triggers makes a green flash, and the alarm light triggered by a fourth make a red flash.

The app coordination module (23) may ensure that the pain indicator units and virtual pain indicator units that the app coordination module (23) is instructing make different auditory or visual signals when activated, using any method known in the prior art. The app coordination module (23) may also use the following method: Some kinds of input devices, when manufactured, will include a processor, a receiver, a transmitter, and one or more alarms, and/or one or more alarm lights. The processor is programmed with a list of sounds that the alarm (If the input device includes an alarm) is capable of making, and a list of visual signals the alarm light (If the input device includes an alarm light) can make, and a device ID for the input device. The processor (29) in each of these input devices will also be able to pick which of these sounds any alarm in that input device will make, when activated, and which of these visual signals any alarm light in that input device will make, when activated. When an app coordination module is used with these input devices, the PC on which the app coordination module is running will establish communications with the processors in the input devices which the app coordination module is instructing. Some ways (Not the only possible ways) in which this can be done are that A. The transmitter in the input device will broadcast a signal, which the PC on which the app coordination module (23) is running receives, and then the app coordination module (23) will use the PC's wireless transmission capability to send instructions to the receiver in the input device, which will transmit the instructions to the processor (29) in the input device, or B. The app coordination module (23) will cause the PC where the app coordination module (23) is running to broadcast a signal, and the input device's receiver receives this signal, and then communicates the signal to the input device's processor. The processor will then cause the input device's transmitter to broadcast a signal, which the PC running the app coordination module (23) receives.

Either during or immediately after communications between the input device's processor and the app coordination module are established, the input device's processor will transmit the device ID, and the list of sounds that the alarm (If the input device includes an alarm) is capable of making, and a list of visual signals the alarm light (If the input device includes an alarm light) can make, to the input device's transmitter, which will broadcast this information, so that the app coordination module (23) receives it. The app coordination module will then examine the device IDs of the input devices' that it is instructing, and the sounds and visual signal that the components of each input of the device are capable of making, and the app coordination module will select a different sound for the alarm in each input device to make, out of those which the alarm is capable of making, and a different visual signal for the alarm light in each input device to make, out of those which the alarm light is capable of making. The app coordination module will then cause the PC (42) on which the app coordination module (23) is running to broadcast instructions specifying the device ID of each input device that the app coordination module is instructing, and specifying which sound (of the sounds that the alarm in that input device can make) any alarm in that input device will make if one of the pain indicator units in that input device is activated sufficiently, and/or specifying which visual signal any alarm light in that input device will make if one of the pain indicator units in that input device is activated sufficiently. The app coordination module (23) will cause the PC (42) on which it is running to broadcast signals specifying the device ID of each of the input devices the app coordination module (23) is instructing, the sound any alarm in each of the input devices that the app coordination module (23) is instructing should make, and the visual signal any alarm light in each input device that the app coordination module (23) is instructing should make.

The input devices do not all need to be of the same type. Input devices of multiple types, that are capable of transmitting the relevant information, can be used with the app coordination module in the way discussed above.

This capability of the app coordination module (23) or the coordination module (16)'s similar capability can be useful in numerous situations, such as when a large number of users, with input devices, come together, and healthcare providers need to quickly discern which of the users are experiencing pain, and how much pain they are experiencing. An emergency situation like a natural disaster is one example of a situation where a large number of users are brought come together to be observed by medical personnel after the users have been injured.

In some embodiments, the app coordination module (23) will send information about the alarm(s) and alarm light(s) in each input device and which sounds and/or visual signals the alarms and/or alarm light(s) in each input device, respectively, are supposed to make, because of the app coordination module (23)'s commands.

The app coordination module (23) can also be designed to operate with input devices in the following manner: Some types of input devices can be designed in "series" with device IDs issued in a pattern, so that each series contains input devices with device IDs that have certain predictable parts, which repeat for each series. An example is the last four digits in the device ID of the first input device in the series' being "0001", the last four digits of the device ID of second input device in the series being "0002", etc. The app coordination module (23) or coordination module (16) will be programmed with the alarm signals and visual signals each of the input devices with a device ID in a certain range is capable of making. A user, such as a healthcare provider, can cause their app coordination module to use the PC's broadcasting capabilities to broadcast a command for the input device with the first device ID within the range to make one alarm signal or visual signal when one of the indicating parts in that input device is activated when that input device is within a certain physical distance of the PC running the app coordination module, for the input device with the second device ID within the range to make a different alarm signal or visual signal when one of the indicating parts in that input device is activated when that input device is within a certain physical distance of the PC running the app coordination module, etc.

The app coordination module, in some embodiments, can also connect with a group of PCs with remote programs and cause each one of them to broadcast different alarm signals, using the PCs' broadcast capabilities, and different alarms, using the PCs' display and lighting capabilities. For example, if a large number of users with cellular phones, running remote programs, are admitted to a hospital, these users can give their remote programs permission to connect to that hospital's app coordination module, running on one of the hospital's PCs. The remote programs can then broadcast a signal which the app coordination module will receive, the hospital's app coordination module will respond and assign a different sound for the remote program running on each of the cellular phones to make, using that cellular phone's sound creation capabilities, and/or a different visual signal for each of the cellular phones to make, using the cellular phones capabilities to create such signals. Alternatively, in some embodiments, the app coordination module will send out the initial signal, and the remote programs running on the cellular phones will respond to that signal and connect to the app coordination module and then the hospital's app coordination module will respond and assign a different sound for the remote program running on each of the cellular phones to make, using that cellular phone's sound creation capabilities, and/or a different visual signal for each of the cellular phones to make, using the cellular phones capabilities to create such signals. In some embodiments, the connection of the app coordination module to the remote programs could be executed through the remote programs' receiving modules.

The app receiving module (24) is a module of the remote program (20) that uses the PC's reception capability (Generally wireless reception capability) to receive responses. In some embodiments, the app receiving module can use the PC's reception capability to receive other information. The app receiving module (24) can be configured to receive responses from specific input devices, or concerning specific users (based on their user IDs). For example, an app receiving module (24) running on a specific user's PC can be configured to receive and/or record responses encrypted to indicate that they pertain to a specific user, or encrypted with a specific device's device ID. The app receiving module (24) can then store these responses in an app database (44) in some but not all embodiments. Whether or not these responses are stored in the app database (44), the app receiving module (24) can also be configured to use the PC's wireless capability to re-transmit the responses that it receives, thus hopefully increasing the chances that these responses are recorded in the centralized integrated database (10) later.

In some embodiments where the remote program (20) includes both an app receiving module (24) and an app coordination module (23), the app receiving module will, in addition to its other functions, receive broadcasts that the transmitters in input devices send, which include information about which sounds the alarm(s) in each of those input devices are capable of making, and which visual alarm signals the alarm light(s) in each of those input devices are capable of making. The app receiving module will send the contents of these broadcasts to the app coordination module.

The app display module (25) is a module of the remote program (20) that displays information on a user's or healthcare provider's PC. The information being displayed can include, in some embodiments, information about which users in a specified user group is experiencing pain at the moment, and the results of statistical calculations about the pain the users in a defined population reported. The information being displayed can also include, in some embodiments, graphs about the relationships between the pain experienced by individuals or groups and other variables, and graphs of other kinds.

The results of calculations and graphs created by the app calculation module are also sent to the app display module for display to the user and/or to researchers.

In some embodiments, the app display module (25) can include the ability for the user to input information about the pain that he/she is feeling's degree, type, and location. The app display module (25) can then send this information to the app calculation module, and the app calculation module will then compare this pain to a set of the user's registered responses, and give the user information about how this pain measures against the set of the user's registered responses, in terms of the percentile of the set of registered responses the user's pain on this particular occasion falls into, etc.

The proxy model (26) is a device that does not need to resemble any body part, and which contains one or more pain indicator units (1) that the patient is supposed to activate if he/she experiences pain in designated areas of his/her body. For example, the proxy model may include a pain indicator unit which, if activated, indicates that the patient is experiencing pain in his left hand, and a second pain indicator unit which, if activated, indicates that the patient is experiencing pain in his right hand. Then, the proxy model has a third and fourth pain indicator unit to indicate when the patient is experiencing pain in his left and right feet, respectively. However, the proxy model can have virtually any shape. For example, the proxy model can look like a rod, or something else.

A proxy model that resembles a body part, for example a foot, and that contains a single pain indicator unit that, when activated, indicates that the user is experiencing pain in his or her foot, is simply a part model.

The Integrated Statistical Display (27) is a module of the centralized program (45) that displays the results of statistical calculations the Centralized Calculation Module (28) performed. The integrated statistical display, in some embodiments, can also display the graphs of either the statistical calculations' results or graphs of the registered responses themselves. For example, the integrated statistical display, in some embodiments, can display a bar graph with the percentage of a population of patients who report experiencing pain at different times of day as the y-variable and the time of day as the x-variable. The integrated statistical display should be able to show any kind of graph that the centralized calculation module can calculate, or the results of any kind of statistical calculation, that the centralized calculation nodule can execute.

The centralized calculation module (28) is a module of the centralized program (45) that performs statistical calculations on all, or a subset, of expressed information, including the data concerning the intensity, locations and types of pain experienced by users, wherein this data is transmitted to the centralized receiving module (30). The centralized calculation module (28) can also, at a minimum, perform, all of the calculations, and display all of the results that the app calculation module can perform, and can do so on all, or a subset, of the data concerning the intensity, locations and types of pain experienced by users, that is transmitted to the centralized receiving module (30), and the expressed information in the centralized integrated database (10). This includes, but is not limited to, finding users with common characteristics in the centralized integrated database (10) and creating summary statistics about those users' responses. The centralized calculation module (28) can also create graphs of these responses, and summary pain lines and pain shapes, for a user population, such as average pain lines and pain shapes.

The centralized calculation module should also be able to apply a refining function to a set of users' registered responses, drawn from the centralized integrated database. A researcher applying the refining function can also modify parameters A-G, and view the results of a statistical analysis that the centralized calculation module has performed, with one or more of parameters A-G modified. The centralized calculation module will send the results to the integrated statistical display (27).

The centralized calculation module may have advantages over the app calculation module, in that it may be able to do some calculations faster, because it may have access to more computing power, and may, in some cases, have access to more data or be able to use more data.

In some embodiments, a researcher using the centralized calculation module can calculate statistical information about user subgroups by using the expresseil information in the centralized integrated datahase (10) and specialized databases (33). The centralized calculation module can, for example, calculate the pain patterns of users who have experienced a certain event in the last 30 days, at a research- er's command, by A. Searching the centralized integrated database (10) to find the users who have that event recorded in their individual information, during the last 30 days. B. Examine the registered responses of those users during the time since the event happened. C. Create any desired graphs, execute any refining function and/or perform any statistical calculations the researcher has commanded the centralized calculaticrn module to perform.

One example of a "registered event" where this can be useful is a medical or dental operation. The centralized calculation module can examine the pain patterns of users who experienced the same general type of operation, but done through different techniques, or different post-recovery procedures. The centralized calculation module can find, in the centralized integrated database, users who experienced the same general operation but with the different techniques, different post-recovery procedures, or other differences the researcher wishes to investigate. Then, the centralized cal- culation module can compare the distributions of pain of the two groups using statistical techniques. For example, the centralized calculation module can calculate the average means of the nominated pain levels of users in the two groups, at different points after the operation, and compare them. The centralized calculation module can also calculate the areas under pain curves for different locations, for the two user groups, and can also calculate the volumes of pain shapes, for the two user groups, and compare them. The centralized calculation module can thus help detect opera- tive and recovery techniques, and other medical and dental techniques, that are better from the point of view of reducing the pain users experience, Such techniques might be opti- mized further: After a "less pain-causing" technique is discovered, researchers can try to modify the technique further, or add additional techniques, to further reduce the pain users feel, then do this again, etc.

In general, this will be more effective if more information about registered events is included in the records of those registered events in the centralized integrated database and the other Databases.

Related to this, the centralized calculation module may be able to detect when a single user's registered responses in a location, a certain length of time after an operation, are in a very high percentile of the pain degree that users registered, the same length of time after the same kind of operation. The centralized calculation module may be designed to send an automatic alert to a specific person when this happens, such as an alert to the user's primary care physician. The primary care physician can then contact the user to make sure the user is okay.

The centralized calculation module should also be able to create graphs of the results of refining functions, when commanded by the researcher.

The centralized calculation module can also perform analyses on individual databases, like the app calculation module.

The centralized calculation module should also be able to fit distributions to groups of registered responses, so that researchers can understand how the distributions work bet- ter. A distribution could be normal, or different, like lognor- mal, exponential, or something else. Figure out correct distributions.

In some embodiments, the centralized calculation module will be able to perform chi-square analysis and analysis of variance (ANOVA) on groups of registered responses.

Researchers can use the centralized calculation module as a tool to find ways to improve patient outcomes, public health, and users' quality of life in at least the following ways:

First, researchers can use the centralized calculation mod- ule (28) or an app calculation module (22) to examine users' pain patterns, created from users' registered responses in the centralized integrated database (10), a specialized database (33), or an app database (44). Researchers can use the centralized calculation module (28) or app calculation mod- ule (22) to calculate whether there are statistical relation- ships between either A. Users' registered pain levels in different body parts, and/or B. How and when users' regis- tered pain levels in different body parts rose and/or fell, and C. Environmental information, such as levels of an envi- ronmental variable, gained from environmental monitors and recorded in the centralized integrated database (10).

The researcher can use the integrated statistical display (27), to view results of statistical analysis that the researcher performed using the centralized calculation module (28), and graphs that the researcher commanded the centralized calculation module (28) to create, and the researcher can use the app display module (25) to view results of statistical analysis that the researcher performed using the app calcu- lation module (22), and graphs that the researcher com- manded the app calculation module (22) to create.

One way for a researcher to do this is for the researcher to command the centralized calculation module (28) to perform a specific statistical analysis upon registered responses in the centralized integrated database (10), such as finding out whether there is a correlation between tempera- ture (An environmental variable) and the pain levels users expressed in registered responses. The researcher might also command the centralized calculation module (28) to make specific graphs, such as a graph with the pain levels users expressed in registered responses as the Y axis and tem- perature as the X axis.

The centralized calculation module will then perform the analysis and create the graphs, and send the analysis's results and the graphs to the integrated statistical display (27), which will display the analysis's results and the graphs to the researcher.

The researcher can also make the analysis more targeted in various ways, which may yield results that a more general analysis may fail to detect. The researcher may use the centralized calculation module to apply a nominating rule and nominating periods to the data on which the analysis is being performed. Using the users' nominated pain levels might lead to more useful results.

The researcher can also command the centralized calcu- lation module (28) to create a specialized database (33) from the centralized integrated database (10) and command the centralized calculation module (28) to perform the desired analysis on the specialized database, and/or create graphs based on the registered responses in the specialized database. The centralized calculation module (28) can create the specialized database by finding the registered responses in the centralized integrated database (10) that have certain characteristics or have certain common characteristics, and placing those registered responses in the specialized database. Examples are A. Registered responses that were created by users who were in certain specified geographic locations at the times the responses were created, or B. Registered responses that were created by users whose ages at the times the responses were created were recorded in the centralized integrated database and were within a certain age range, or C. Registered responses that came from users who had a certain disease, where that disease was mentioned in the users' individual information saved in the centralized integrated database (10).

Examples of the centralized integrated database finding specific input devices are A. A group of input devices being used by users who have a certain medical condition, or B. A group of input devices being used by specific users, or C. A group of input devices defined in some other way. The command can be given to the display section or human body display in any of the ways known in the prior art, including, but not limited to, the command being typed into the display section (2) or human body display (12).

In some embodiments, commands based on SQL or another programming language can be used in picking the set of registered responses, on which to perform statistical analysis.

In some embodiments, the researcher can also command the centralized calculation module to perform the desired analysis on the centralized integrated database directly, by finding the needed responses in the centralized integrated database and performing the statistical analysis then.

The researcher can limit an analysis to registered responses that came from certain locations, in some embodiments, by commanding the centralized calculation module that one of the criteria to use in selecting the set of responses to use to perform the statistical analysis is to pick responses from certain GPS coordinate ranges.

Some other ways that the centralized calculation module and the centralized integrated database can be used include: Comparing users' registered responses with environmental information to see if there are patterns, or patterns regarding specific people's injuries, in the registered responses that are influenced by environmental variables. Also quantifying environmental damage from pollution better by correlating poor environmental variables to pain. When examining environment's influence on pain patterns, users don't need info about health conditions, but it would help.

Examining pain patterns of users after different operations and treatment regimens, to see what techniques and treatment regimens are better, or better for different user populations. Also separating user populations by age and weight, if this information is available.

One idea behind the centralized integrated database is to create very large dataset including people in all sorts of conditions. Use dataset to predict how to reduce pain by comparing situations, and apply it by finding the situations where pain is reduced the most.

Trying to predict possible severe impacts of an individual's health conditions by looking at the individual's pain patterns and comparing them to pain patterns of people who have experienced the same health condition, and finding whether the user's present pain patterns fall in a "dangerous" zone, which is correlated to more severe health problems. In some embodiments, a warning can be sent to the user if the user's pain pattern falls into a "dangerous" zone, where the combined probability of severe health outcomes of defined types exceeds a certain threshold. The threshold can be decided by healthcare providers or others.

When an individual user reports a certain pain pattern, the centralized calculation module detecting that this pain pattern is different from normal and could indicate a threat. For example, that the pain pattern indicates appendicitis or presages aneurysm or a stroke. This would work by the centralized calculation module taking the user's pain pattern from one or more areas of the user's body, and comparing it to pain patterns, from the same of users' bodies, for the time before, or during, a user experiencing a health condition.

Comparing information with individual information deleted.

Finding out whether there are correlations between registered responses and environmental information to see if there are patterns in the registered responses that appear to correlate with environmental variables, or patterns regarding specific people's injuries. Also quantifying environmental damage from pollution better by correlating poor environmental variables to pain levels. If researchers are looking at environment, they don't need info about health conditions, but it would help.

Reduction of medical error-Particularly non-malpractice "errors in judgment", by figuring out when a particular operation is going wrong. For example, when labor is going wrong, by figuring out that the pain pattern the person in labor is exhibiting is abnormal. The present invention when can also detect when injuries are not healing right, by figuring out when a user's pain pattern in an injured body part is abnormal, by comparing that pain pattern to pain patterns of others after similar injuries.

Finding differences between how groups experience pain, such as differences in pain patterns between groups of users in different age brackets.

Educating healthcare practitioners by showing them pain patterns and pain volumes of users in different scenarios.

Observing patterns in the data in general, by using graphs. Also maybe find clusters, and find reasons those clusters are there.

Can be used for other studies, such as whether contact with different kinds of things cause more pain.

Analyzing how physical therapy and exercise are working.

If you're looking at individual pain data during or after an operation, you don't need info about health conditions at all. You can just look at pain patterns during and after the operation. Health condition data would help, though.

Examining a pain a user feels over longer periods may allow the user to detect other health issues, such as heart murmurs.

Some of the centralized calculation module (28)'s embodiments will have the capability to fit a statistical distribution to a group of data points where each data point represents a user's expressed pain level, either in general or in a body part, and the centralized calculation module (28) is able to fit a statistical distribution to a group of data points where each data point represents the result of a function applied to a group of users' expressed information a certain length of time after the users experience an event. An example is where one data point represents the result of a function applied to a group of users' expressed information 24 hours after the users underwent an operation, a second data point represents the same user group's expressed information 48 hours after the same operation, etc. In this example, the users can experience the operation at different times, because the date and time they each experience the operation will be recorded in their individual databases and the centralized integrated database, and the centralized calculation module can search for the time they each experienced the operation and find what is 24 hours after that point, 48 hours after, etc. The centralized calculation module (28) can fit a bell curve-like distribution, or a lognormal distribution, exponential distribution, or binomial distribution, Bernoulli distribution, Poisson distribution, normal distribution, or t-test distribution to the data points if appropriate.

The Processor (29) is a computer processor, as known in the prior art.

The centralized receiving module (30) is a module of the centralized program (45) that receives all registered responses that users have sent via the internet, and integrates these responses into the centralized integrated database.

The cover (31) is a cover for part or all of a mouth model, part model, or body model or proxy model that prevents one or more of the pain indicator units (1) thereon from being pressed or otherwise activated accidentally.

The pain indicator piece (32) is an item that is not an "original" part of the invention, to which the pain indicator unit(s) (1) is attached in some embodiments of the invention. For example, a user can place two pain indicator units (1) with suction cups attached on a piece of furniture. The piece of furniture is a pain indicator piece.

The specialized database (33) is a database that contains a subset of all responses the centralized receiving module received, where the subset is organized according to some characteristic or combination of characteristics. The characteristic may be, for example, all patients having a certain disease, or all patients in a specific geographic location.

The app transmission module (34) is a part of the app calculation module (22). The app transmission module sends the results of the calculations and graphing that the app calculation module (22) does to the app display module (25) so that they can be displayed to the researcher.

The pain indicator virtual unit (35) is a part of the app calculation module (22). The pain indicator virtual unit is a "virtual" button that appears on a user's PC, so that the user can press or otherwise activate the pain indicator virtual unit to indicate the user's pain level. The indication of the user's pain level is a registered response.

In some embodiments, the app calculation module (22) will display multiple pain indicator virtual units representing different parts of a user's body. The user will indicate that the user is feeling pain in a certain part of the user's body by activating the pain indicator virtual unit that corresponds to that part of the user's body.

In some embodiments, the pain indicator virtual units are part of an image of a human body. In some of these embodiments, the pain indicator virtual unit that "corresponds" to each part of the user's body is a virtual button on that part of the human body image on the screen.

In some embodiments, the user may activate a pain indicator virtual unit by touching it on the PC's screen. The user may show that the user is feeling a higher pain degree, by touching the pain indicator virtual unit, uninterrupted, for a longer time, in some embodiments, or by pressing it harder, in some embodiments, or by moving the user's finger or other body part along it for a longer distance, in some embodiments. Other ways of indicating the degree of a user's feeling by interacting with the screen, that are part of the prior art, are also ways that the user may activate a pain indicator virtual unit. In some embodiments, more than one method of activating the pain indicator virtual units may be used. In some embodiments, a user may also choose which method(s) of activating the pain indicator virtual units may be used.

In some embodiments, each pain indicator virtual unit, when activated, will show how much pain the user is expressing that the user feels in the body part represented by that pain indicator virtual unit. For example, a pain indicator virtual unit can display a number, which is the pain level the user is expressing by activating the pain indicator virtual unit. A pain indicator virtual unit can also fully or partially change color when it is activated, and continue fully or partially changing color as the pain level the user expressed changes. The pain indicator virtual unit can also show the pain level the user expressed in other ways, or through changing in multiple ways at the same time.

For example, in an embodiment where the length of time a user touches a pain indicator virtual unit shows the amount of pain the user is feeling in the body part corresponding to that pain indicator virtual unit, the pain indicator virtual unit may display a number that represents the pain level the user is expressing, and as the user continues to touch the pain indicator virtual unit, the number continues to go up, until it reaches the maximum.

The app input module (36) is a part of the app calculation module (20). The app input module (36) allows a user to input the calculations that the user wants to do and/or instructions for the graphs that the user wants to create, and possibly other operations that the user wants to do, concerning responses in one of the Databases. Then, the app calculation module performs the calculations and/or creates the desired graphs, and displays the calculations' results, and graphs, to the user. For example, the app input module (36) can be configured to allow the user to tell the app calculation module (20) to calculate A. The average pain level the user has experienced in the past 72 hours with a nominating period of 1 hour, and a nominated pain level of the highest pain level experienced during each hour, or to B. Graph the pain level that the user has registered in a certain body part, over the past 120 hours, with a nominating period of 1 hour and a nominated pain level of the highest pain level registered during each hour, and C. Calculate the graph's slope, if any. The app calculation module can also be configured to graph the user's registered responses while the user is experiencing other health conditions, such as the user's registered responses during a time period when the user is experiencing COVID-19. The other health conditions, and the times that the user is experiencing them, is recorded in the user's individual database (11).

For example, in some embodiments of the individual database, information about the user's health conditions might be in one column, and the health conditions might be designated by name, with the names of each of the user's known health conditions during a time period entered into a single entry, pertaining to that time period, in the "health conditions" column. Information about environmental variables such as weather, for each time period, in the user's location, will be entries in another column. The user can then input into the app input module that the user wants to graph the user's responses at the times when the user was experiencing a certain, named, health condition, with a nominating period of 1 hour and a nominated pain level of the highest pain level registered during each hour, and the app calculation module will graph the highest pain level registered during each hour that the health condition's name appears in the "health conditions" entry in the individual database for that user.

The display device (38) is a specially designed physical device that performs some of the same functions as the display section (2). The inventors suggest that the display device will be more useful in some embodiments using a pain scale than in embodiments not using a pain scale. The display device can be useful for personnel responsible for caring for a large number of users, such as personnel in a hospital ward, field hospital, or convalescent home, or even child protective services personnel trying to assess whether children in foster homes are being treated well. The display device quickly shows whether user subgroups are experiencing notably high pain levels, so that personnel can focus their efforts on those user subgroups. A subgroup can have multiple users or be a "subgroup of one".

The display device will have multiple sections, each section with at least one light. The display device will usually include a receiver, and will receive input through the receiver from a group of input devices with transmitters. The input should comprise the expressed information of users using the input devices in the group, including the pain levels these users experience. Most embodiments of the display device will also include a processor operatively connected to the receiver and the lights. The group of input devices can be divided into subgroups. The processor can, using the input devices' device IDs, or using a method known in the prior art, divide the input from the input devices into subgroups, matching the subgroups into which the input devices themselves are divided, and the processor will perform at least one statistical function (a refining function) on the input from the subgroups. In most embodiments, the processor will at least be able to calculate the mean pain level (calculating the mean is an example of a refining function) the users in each subgroup expressed so far during the current time period (The current time period is defined on the display device (38), and preferably shown on the display device) by calculating the mean pain level the users in each subgroup are expressing, based on the input the receiver is receiving from the input devices in each subgroup so far during the current time period (For example, the current minute). Each light is pre-designated to show the refining function's result for one of the subgroups. The processor controls the lights and will cause each light to glow in the resulting color representing the level, on the pain scale being used, of the statistical function's result, that the processor calculated, using the input from one of the input device subgroups. For example, if "red" represents a level of 5-6 on the pain scale being used, and the statistical function the processor is using is to calculate the mean expressed pain level for each subgroup, one of the lights on the display device glows red, this shows that the user subgroup that light represents are experiencing an average pain level of 5-6.

Several other versions of the display device are described below. In each of them, the processor will control the lights to show the results of the refining function the processor has been commanded to use. For example, if the processor is commanded to use the median expressed pain level for each subgroup, and the median differs from the mean, the lights will glow in the colors that, on the pain scale being used, reflect the subgroups' median expressed pain levels. For example, if a light being colored red indicates a pain level of between 5 and 6, and the median pain level of a subgroup is between 5 and 6, the processor will cause the light to glow red.

In some embodiments, the input devices will be designed to allow each user to register the pain level the user is experiencing in multiple body parts (Most likely the same body parts for each input device), using one of the methods discussed herein. Then, the transmitters on the input devices will transmit the users' expressed information for multiple body parts. The display device (38)'s receiver will receive these transmissions and send the expressed information to the processor. The processor then calculates the refining function's result for the users in each subgroup's expressed information for each body part. For example, if the input devices are able to separately register the pain that users may be separately feeling in their heads, chests, and other body parts, the processor calculates the refining function's result for the expressed information for the users in each subgroup's heads, the users in each subgroup's chests, etc.

In some of these embodiments, instead of a light for each user subgroup, there will be multiple lights for each user subgroup. The lights will each indicate the refining function's results for the users in a subgroup, concerning one of the body parts for which the users could express information using the input devices. In the example above, there is a light for the refining function's result concerning each user subgroup's expressed information for their heads, another light for the statistical calculation's result concerning each user subgroup's expressed information for their chests, etc. All the lights are connected to the processor. The processor will cause each light to glow in the color which, on the pain scale being used, represents the level of the refining function's results, the processor calculated, for one of the body parts of the users in a subgroup.

In some embodiments, the display device (38) will include a memory, operatively connected to the processor and potentially the receiver, and the memory will store the expressed information received from the input devices over one or more time periods. The memory will send this information to the processor, to do statistical analysis, and the processor will control the lights to make them glow in the appropriate way to convey the information the person using the display device (38) wants them to convey.

In some embodiments, the person using the display device (38) is able to switch the length of the time period for which the processor calculates the refining function of the responses coming from the input devices between multiple potential time periods. For example, the person using the display device (38) may switch the time period for which the processor calculates the result of the refining function of the responses coming from the input devices from 1 minute to 1 hour. Then, if the processor is calculating the mean pain level expressed by each user subgroup, the processor will calculate the mean pain level the users in the subgroups expressed so far during the present hour, instead of the present minute.

In some embodiments, the person using the display device (38) is able to select the refining function the processor performs, between multiple options, either by manipulating a manual switch or selecting the function to be performed on an electronic display on the display device. Some potential statistical functions the person using the display device (38) could switch between are the mean, median, mode, standard deviation, rate of increase over the last time period, highest pain level in the time period, and lowest pain level in the time period, for the pain the subgroups experienced (Or experienced in specific body parts, in embodiments where the display device has the capacity to show the results of functions of the pain experienced by users in specific body parts). The ability to use the display device to select any of the other functions that the processor is able to perform is explicitly part of the present invention. The manual switch or electronic display will be operatively connected to the processor and will send the processor the command that a new function should be performed.

In some embodiments, the person using the display device (38) is able to use a manual switch or electronic display to switch the time period that is the source of the data on which the processor performs statistical calculations from the current time period to the last complete time period of the same type, or vice versa. The manual switch or electronic display is operatively connected to the processor and will send the processor the command switching the function to be performed.

In some embodiments, the person using the display device (38) is able to use manual switches or an electronic display on the display device (38) to select whether to use a nominating rule and nominated period, and if so, what nominating rule and nominated period to use. This might give the information display device (38) received additional clarity. If a nominating rule is used, the processor will calculate the results of the refining function for the nominated pain levels for the users in each subgroup. Then, the processor will command each light to glow in the color that represents the result of the refining function being applied to the nominated pain levels for the users in the subgroup represented by that light. For example, if the result of the refining function being applied to the nominated pain levels from a user subgroup is between 5 and 6 on the pain scale being used, and the light representing that user subgroup glows red when the refining function's result for that subgroup is between 5 and 6, the light will glow red. The manual switches and electronic display will connect to the processor in the display device (38).

In some embodiments, the lights will show the results of the refining function of the pain felt by users in the subgroups in another way, instead of showing the results through glowing in different colors based on the results and the pain scale being used.

A time division indicator (39) is a unit (In most cases a button) on an input device that a user can use (by pressing the time division indicator if it is a button) to indicate the period of time (the time division) to which responses given on the input device are assumed to apply. The "time division" is the period of time. Examples of time divisions are 1 second, 1 minute, 1 hour, and 1 24-hour day. As many other examples of time divisions are possible as discrete periods of time exist.

For example, a user can use the time division indicator (39) to indicate that each response should be considered a response that applies to all of the hour in which the response happens, or all of the minute when it happens, or all of the day, when it happens, etc. If the user selects a time division of 1 hour, for example, this can save the user the trouble, of having to keep activating a pain indicator unit more than once during the entire hour. The user in some versions can switch the time division. For example, the user can switch it from one minute to one day, etc. In some versions of the invention, if a user makes multiple responses applying to the same body part, and these responses each apply to the same time division, the system will just average them, and in other versions the system will pick the highest. The time divisions are different from the "nominating period" selected by a researcher because the user who is reporting their own pain selects the time division.

In some versions of the invention involving an app on the user's phone or other computing device, the app will include a time division indicator function, so that the user can choose, or switch, the time division to which responses apply. Each response will apply to the timestretch in which that response is registered.

An ID input port (40) is a component on an input device capable of receiving input where a user can input his/her unique ID, so that the user's identity is recorded with reference to the responses the user later gives, using that input device. For example, an ID input port can be a port where a user's thumbprint is read, or where a user's voice is inputted, or where a user inputs a code or password to identify themselves (All ways that the user can identify themselves). Then, when the user makes responses, using the input device, the responses are listed in any centralized integrated database, specialized database, or individual database with the correct identity of the user who made the responses.

A data export port (41) is a port on some input devices which the user can use to export, from that input device, data that has been registered on that input device. A USB port might be an example of a data export port. The user can run a USB cable from the data export port to a PC and export the data to the PC.

As those skilled in the art will appreciate, any PC used with the invention may include an operating system (e.g., Windows, OSX, iOS, UNIX, Linux, MacOS, Android, etc.) as well as various conventional support software and drivers typically.

A PC (42) is a desktop or laptop computer, smartphone, similar instrument, or the following: a computing system including at least the following five components: A processor for processing digital data, a memory for storing digital data coupled to the processor, an input digitizer for inputting digital data coupled to the processor, a device that displays video, coupled to the processor, and a memory for displaying information derived from digital data the processor processed. As those skilled in the art will appreciate, the PC may include an operating system (e.g., Windows, OSX, iOS, UNIX, Linux, MacOS, Android, etc.) as well as various conventional support software and drivers typically associated with computers or smartphones.

The pain indicator skin (43) is a membrane, with small pain indicator units, embedded in it, that surrounds a human body model, mouth model, part model, proxy model, or pain indicator piece. The user can indicate that the user is feeling pain by pressing on, or otherwise activating, the pain indicator skin. In most embodiments, if the user presses harder, on the pain indicator skin, then a higher pain level is registered. In most embodiments, the location(s) of the pain indicator units the user is activating will indicate the location(s) where the user is feeling pain. For example, if the user is activating the pain indicator units on the arms of a human body model, it will be registered that the user is experiencing pain in the user's arms.

Most embodiments involving a pain indicator skin (43) will also involve that pain indicator skin (43) being directly or indirectly connected to a transmitter, that can broadcast the responses that users make, using that pain indicator skin.

Use of a pain indicator skin on an input device, or some of its subcomponents, will probably be more expensive than use of pain indicator units on the input device or subcomponents, but can have other benefits. For example, a user can press or otherwise activate any part of the pain indicator skin to register a response.

An app database (44) is present in some embodiments and is a database stored on a PC, where copies of the responses registered on a specific input device and received by that specific PC, or registered by a specific user and received by that specific PC, are stored. The app calculation module can perform calculations and other operations like graphing on the entries in that app database. However, in general, the individual database, centralized integrated database, or a specialized database should be used instead, when possible, because the records in those databases are more complete.

A centralized program (45) is a program that controls the centralized integrated database (10), the individual databases, and any specialized databases. The integrated statistical display (centralized calculation module (28), and centralized receiving module (30), in most embodiments, are part of the centralized program (45).

Part models (17), mouth models (8) and human body models (9) should preferably resemble the body parts that they are supposed to imitate; For example, a part model (17) of a hand should resemble a hand, to increase accuracy when a user activates one of the pain indicator units (1) on that part model (17). If a part model (17) looks more like the body part it is supposed to imitate, then the user is more able to select the pain indicator unit (1) located in, or closest to, the area of the part model that corresponds to the part of the body part where the user is experiencing pain. The same reasoning applies to mouth models (8) and body models (9).

Some of the ways that the user could identify himself or herself to show which user responses pertain to, are A. To input a user ID which is a code, such as a voice recognition code, into the component the user is using to register responses, or B. To use facial recognition, or another biometric system, C. Input another kind of user ID such as a fingerprint or footprint, or face recognition, into the part model (17), mouth model (8) body model (12), app, or other component the user is using to register responses. In some embodiments, the facial recognition, and other forms of inputting an identifier listed above can be done by importing the identifier into an ID input port (40). Healthcare providers could also input a user's user ID into a specific input device. The system will then proceed to identify the user with the responses the user registers, and register these responses in (if available in that embodiment) the user's individual database (11), the centralized integrated database (10) and any appropriate specialized databases (33) and app databases in connection with that user.

In some embodiments, a user can have multiple user IDs, which each identify the user, as long as these user IDs are each unique, and as long as, if the user enters any one of these user IDs into the component the user is using to register responses, the system will enter those responses in the appropriate databases, in connection with that user.

Many embodiments use a pain scale with multiple levels to describe the degree of the user's pain.

The First Group of Embodiments

The first embodiment group are instruments with one or more pain indicator units (1) that the user can activate. For example, the user can be a patient, in the dentist's chair, and the instrument can have one or more pain indicator buttons. The instrument can be placed on a table next to the user where the user can grasp it, or the instrument can be placed in another location. When the user presses a pain indicator button, an alarm light (3) flashes, and informs the dental or medical personnel or other caregivers nearby that the user is experiencing pain. An alarm (14) can also sound and inform the dental or medical personnel or other caregivers, or both an alarm light can flash and an alarm can sound. The dental or medical personnel, or other caregivers, will then stop performing work on the patient and take a "break", also giving the patient a "break".

The alarm (14) and/or alarm light (3) can be attached to the same instrument as the pain indicator unit(s), or the instrument with the pain indicator unit(s) can also include a transmitter, and the alarm (14) and/or alarm light (3) can be attached to another instrument with a receiver. The alarm (14) and/or alarm light (3) would be operatively connected to the receiver(s) and would be turned on when the receiver(s) receives a transmission from the transmitter.

Embodiments in the first embodiment group can also involve one or more display sections (2) which are also connected to one or more receivers (16) and which display an indication that the user is experiencing pain when one of the pain indicator units is pressed.

The Second Embodiment Group

Embodiments in the second embodiment group include a mouth model (7), including the upper and lower jaw, and teeth, preferably 32 teeth to represent the 32 teeth in the human mouth. The mouth model does not need to represent a specific person's mouth, but, in some versions, can be designed to represent a specific person's mouth. Pain indicator units are placed on many places on the mouth model, such as on the mouth model's teeth. If the user feels pain in any area of his or her mouth, the user can activate one of the pain indicator units, such as by pressing one of the pain indicator units if the pain indicator units are buttons.

Embodiments in the second embodiment group may also involve one or more alarms and/or alarm lights that are activated when a user activates a pain indicator unit. These alarms and/or alarm lights can be attached to the mouth model, or the mouth model can include a transmitter, which is operatively connected to the pain indicator units, and when a user activates a pain indicator unit, the pain indicator unit will cause the transmitter to broadcast a signal that the pain indicator unit is being activated. In some embodiments in the second embodiment group, the alarms and/or alarm lights can indicate which of the pain indicator units the user is activating, thus showing where, in the user's mouth, the user is feeling pain.

The Third Embodiment Group

Embodiments in the third embodiment group use a human body display (12). Input devices with pain indicator units and/or pain indicator skins send input, comprising users' registered responses, to the human body display. The human body display displays the results of calculations performed on this input, giving healthcare providers who view the human body display a quick, precise view of patterns in the pain experienced by a population of users. They can then use the results to improve patient care.

The human body display might also include an app database (44), saved on a memory that is part of the human body display, so that the human body display can keep the data it is being sent, about users' registered responses. The human body display might also include a processor, to make calculations concerning the pain felt by users. In some embodiments, the human body display will include a version of an app calculator module (22), which is able to perform the calculations needed to have the human body display show the correct images.

The human body display will display visual representations of the pain felt by a user group, which would allow healthcare providers viewing the human body display to learn more, hopefully, about relieving the users' pain and other symptoms. The human body display can mark boundaries between parts of the image of the human body that the human body display is showing, and can also display a number on each of the image's body parts to show a statistic related to the pain the users feel in that body part. Some examples of such a statistic are: Showing the population of users' average pain level in each of their body parts during the last timestretch, or to show the population of users' average nominated pain level averaged over the users' nominating periods for a set amount of time in the past (Such as the past 24 hours). Some ways that the amount of pain, or average amount of pain, or a statistic representing some other function of the amounts of pain that the users in the population of users have felt (such as the nominated pain levels' median or mode over a certain time period), can be shown, are through a number representing the statistic being displayed on the relevant body part to which the statistic applies (Such as the median nominated pain level in users' right knees being displayed on the right knee in the image of a human on the human body display), or through the relevant body part glowing in a certain color, where the color changes as the chosen statistic concerning the amount of pain the population of users' registered responses of the amount of pain the individual users are experiencing in that body part varies. Multiple ways that the color could change as the users' registered responses changes are discussed elsewhere in this application.

In some embodiments, the healthcare personnel or other users viewing the human body display can select what information they want the human body display to show, on, or close to, each part of the image of the human being displayed, by selecting the nominating periods and nominated pain levels, in different body parts, of the users whose registered responses are used as the basis of images the human body display displays. In some of these embodiments, the users viewing the human body display can choose that the users' nominating periods are the same as the time divisions the users selected. The users viewing the human body display can, in some embodiments, also choose the population of users whose registered responses are the basis of the images in the human body display. In some embodiments they can also select defined subpopulations within that population, and use the registered responses of one of those subpopulations as the basis of images the human body display displays.

In some embodiments, the viewers viewing the human body display can choose parameters A-G regarding the information that the human body display shows on or next to each body part of the displayed image of all or part of the human body. The viewers can manipulate each parameter in some embodiments, and can manipulate more than one parameter at once, in some embodiments, to understand patterns in the pain users feel, and understand the causes of users' pain and other information about the users' physiology, such as how users' pain can be expected to change as users recover from health conditions.

The refining function can be any statistical formula known in the prior art, including, but not limited to, the mean, median, mode, or standard deviation of the source users' pain level in each body part. The refining function can also be, the mean, median, mode, or standard deviation of the source users' nominated pain level in each body part, or the source users' registered responses. The refining function in some embodiments can also be the slope of a user's pain line.

The refining function, in some embodiments, can be a relationship between results of other statistical formulas. The use of commands based on SQL in some embodiments to denote relationships allows an increased number of potential refining functions that can be used.

In some embodiments, the human body display (12) is able to search the centralized integrated database (10) or specialized databases (33) for users with characteristics the viewer defined. The use of commands based on SQL to denote the categories of users, that are of interest to the viewer, allows the viewer a large amount of flexibility in defining the categories in which the viewer is interested.

The viewer, in some embodiments, will also be able to manipulate Parameters A, B, C, E, F, and G above, regarding the chosen user group' expressed information downloaded from the centralized integrated database (10) or specialized databases (33), to get different views of the source users' pain, how their pain changes, and potentially what is causing their pain, and what can reduce their pain and help their health conditions.

In some embodiments, the human body display (12) can also show display data based on information received from the centralized integrated database (10) and, in quick succession, show display data based on input devices in operative communication with the human body display (12), so that the viewer can compare them.

In some embodiments the human body display (12) can include an app calculation module (22) to do calculations on data imported from the centralized integrated database (11).

In some embodiments, a single input device will send input to the human body display and the human body display will display representations of the pain the single user of that input device felt. The viewer can manipulate parameters A-G above, to gain better understanding of how, why, and where the user is feeling pain, and about any health conditions the user may have, and the user's recovery from some health conditions. For example, the human body display can mark boundaries between parts of the human body image that it is showing, and display a number on each of the image's body parts that shows the amount of pain the user feels in that body part, or display a number that shows the user's average nominated pain level averaged over the user's nominating periods for a set amount of time in the past (Such as the past 24 hours). Some ways that the amount of pain, or average amount of pain, or another function of the amounts of pain that the user has felt (such as the median or mode of the nominated pain levels over a certain time period), can be shown, are a) through a number being displayed on the relevant body part, or b) through the relevant body part glowing in a certain color, where the color depends on the amount of the result of the function of the amount of pain the user is experiencing in that body part varies. The viewer will have ready access to a source that specifies which color symbolizes each part of the range of possible results of the refining function, and so will be able to quickly see what part of the range the actual results are in.

In some embodiments in the third group, the person (usually a healthcare provider) viewing the human body display is able to "switch" between the human body display representing different users. For example, the human body display may be displaying the amount of pain User A is registering in each body part, but the healthcare provider may tell the human body display to switch to displaying the amount of pain user B is feeling in each body part.

The Fourth Embodiment Group

The fourth embodiment group uses one or more batteries (21) to power any electrically powered pain indicator unit(s)

in the input devices and possibly power other electrically powered components of the input devices. The pain indicator units are connected to input devices. The batteries (21) will help the electrically powered components to which they are connected, to operate longer. Each battery would generally be part of the input device that includes the electrically powered components that battery is supposed to power, and would be generally operatively connected to those electrically powered components in a way that allows the battery to send them power.

The Fifth Embodiment Group

The fifth embodiment group uses one or more battery chargers (6) to recharge the batteries (21) when needed. This makes recharging the batteries easier and also helps the input devices the batteries (21) power to operate longer, so that, for a longer period of time, users can use these input devices to indicate when they are feeling pain. The batteries (21) would power any electrically powered pain indicator unit(s) in the input devices and/or power other electrically powered components of the input devices.

The Sixth Group of Embodiments

The sixth embodiment group uses one or more solar panels (7), each of which is operatively connected to a battery charger (6), which is, in turn, operatively connected to a battery (21). The solar panel, when exposed to sunlight, sends power to the battery charger, which sends power to the battery, recharging it. Each battery powers electrically powered pain indicator units in an input device and/or powers other electrically powered components of that input device. This should allow input devices to be operable for longer time periods. Some input devices will include one or more solar panels, one or more battery chargers, and one or more batteries.

The Seventh Group of Embodiments

The seventh embodiment group uses one or more suction cups (13) to hold the input devices containing the pain indicator units (1) in place. The input devices can be placed on other items, such as hospital beds, bedposts, or cots, desks, or other furniture, and will stay in the same locations where they are placed, which can make the input devices easier to use. The use of suction cups will allow the input devices to be moved to other locations easily for user convenience if a user wants to deliberately move an input device, but reduces the likelihood that an input device will be moved accidentally. This capability means that users are more able to find and use the input devices when they are needed. This capability will also allow an input device to be placed in a desired location for one user, where the user can access it conveniently, and then, if a different user with different needs starts to use the input device, the input device can be placed in a different desired location for that second user, where the second user can access it conveniently.

This capability can also be highly useful for mobility-impaired users and users outside of hospital settings. For example, a user in a wheelchair can use the suction cup attached to an input device to place the input device in a desired place on the wheelchair.

This capability is also highly useful in situations like field hospitals, or disaster relief, where a large number of beds or cots must be laid out quickly, and other useful infrastructure is not easily available. An input device with a suction cup can be placed on each bed or cot, using the suction cup, and users using the beds or cots can use the input devices to communicate when they are feeling pain, and how much pain they are feeling. In some embodiments, each user may also be able to move the suction cup with the input device attached to a place close to the bed/cot and convenient for that user.

The items to which the suction cups and input devices are attached will become pain indicator pieces (32) by virtue of the suction cups and input devices being attached to them.

Other methods of attachment of the input devices to pain indicator pieces, especially methods of attaching and detaching them quickly without damaging the input devices, are explicitly part of the present invention.

The Eighth Group of Embodiments

The eighth embodiment group uses one or more human body models (9), each of which is connected to at least one pain indicator unit (1) (In most versions this is a pain indicator button) and each of which also includes at least one transmitter (15). The user can activate the pain indicator unit(s) when he/she feels pain. For example, the user can press the pain indicator units if they are buttons, and the user feels pain. The user should activate the pain indicator unit(s) that correspond to the body parts where the user feels pain. This embodiment group should preferably also involve at least one alarm, alarm light, or both, which can be activated when the user activates one of the pain indicator units.

The Ninth Group of Embodiments

The ninth embodiment group uses multiple input devices, and multiple alarm lights and/or alarms, and also uses a coordination module (16) to coordinate the alarm signals the alarm lights and/or alarms make.

Each of the input devices is operatively connected to at least one alarm light, and/or at least one alarm. The input devices each have a receiver.

The coordination module operates on an electronic instrument, which can be a PC (42) or another type of electronic instrument with a transmitter.

The coordination module communicates with the receivers in the input devices and commands each input device, if activated, to make a different alarm signal from the other input devices. The coordination module selects these "different alarm signals" from among the sounds that any alarm operatively connected to any of the input devices is capable of making, and/or the visual alarm signals (Such as flashing in a certain color) that any alarm light operatively connected to any of the input devices can make. This system will help healthcare providers and caregivers to quickly learn which user(s) are experiencing pain, and to help those user(s).

In some embodiments in the $9^{th}$ embodiment group, the alarm(s) and/or alarm light(s) operatively connected to each input device only make alarm signals if the user using that input device uses it to register pain above a certain level, on the pain scale being used.

In some embodiments, the alarm made by each alarm and/or the visual signal created by each alarm light can be customized, either ahead of time by the user or through commands from the coordination module. The users, in some embodiments, can record the sound they want the alarms they are using to make, when they experience pain, or experience a high pain degree.

The Tenth Group of Embodiments

The 10th embodiment group involves use of position sensors to monitor the position of parts of an input device relative to each other. Some embodiments in the $10^{th}$ embodiment group use position sensors on a mouth model to monitor the position of parts of the mouth model relative to each other.

The Eleventh Group of Embodiments

The eleventh embodiment group includes an individual database (11) where the user's responses are stored. The user, or healthcare providers, researchers, or viewers, can then perform statistical analysis on these responses.

In most embodiments in the $11^{th}$ group, individual information and environmental information will also be saved in the individual database.

In most embodiments in the $11^{th}$ group, the time at which each response is received is recorded, along with the response.

The App

Some embodiments in the eleventh embodiment group will involve remote programs (20) that can be run on PCs (42), and that individual users can use to better understand when and how they feel pain. The remote programs should have, as components, app input modules (36) that users can use to command the remote programs' app calculation modules. The app calculation modules (22) perform statistical calculations, and execute other functions discussed herein, concerning users' registered responses and the user's individual database (11). The app transmission module, which is part of the calculation module can send the results of the calculations the app calculation module performs to the app display module (25) for the user to view. In many embodiments, the remote program (20) will also include an app receiving module (24) that receives responses, and/or environmental information, and/or individual information, and places them in app database(s) for further analysis.

In some embodiments, the remote program (20) will also include an app coordination module (23).

A permanent centralized integrated database is not needed for individuals to use their individual databases to understand their own pain patterns better.

A user can also use the app calculation module to calculate their own pain lines, based on their expressed information, and apply a nominating rule.

The user can calculate their pain patterns after a specific event in some embodiments. The user can also, in some embodiments, place events in their individual database by merging the events from the user's calendar, or by recording the events another way in their individual database, in their individual information.

In some embodiments in the eleventh group, a user can give another user access to the first user's individual database. For example, a child can then give their parent access to the child's individual database, and then the parent can program their remote program to send them the parent an alert if the child's expressed pain level goes beyond a certain level, which is a threshold. A similar arrangement can also be helpful if a child is recovering from a medical or dental procedure, or is sick in school.

A user who is in the hospital can also give their relatives access to the user's individual database, and then those relatives can set alerts on their remote programs to give the relatives alerts if the user's expressed pain level goes above a certain threshold. Then, the user's relatives would know that they should call or visit the user.

In some embodiments in the $11^{th}$ group, a user can (if enough of their own data has been recorded in their individual database) use Bayesian analysis to understand their own pain patterns, and whether certain pain patterns can presage or indicate certain health conditions for the user. The user's app calculation module would examine the user's present pain pattern, and examine whether, when the user experienced similar pain patterns in the past, negative health events followed shortly thereafter. The dates and times of the negative health events will be recorded in the user's individual database. The app calculation module will find the probabilities of these negative health events happening given the present knowledge of the user's present pain pattern. If these probabilities exceed a pre-defined threshold, the app calculation module will send an alert to the user.

Then the user can use the app calculation module to apply a nominating period, if desired, and graph their pain patterns that happened after a registered event. In some embodiments, the user can also calculate their pain shapes' volumes after the registered event. Then, the user can compare the areas under their pain lines and volumes of their pain shapes, respectively, after similar registered events to the areas under their pain lines and volumes of their pain shapes, respectively, after the recent registered event. The user can then try to find the reasons for differences between the user's pain lines for the same body part on different occasions, and between the user's pain shapes on different occasions, respectively. Among other things, the user can try to find which actions by the user, and what environmental information, correlated to lower area under pain curves and/or lower volumes of pain shapes, and then can information to arrange their life in a way that causes them less pain, and also try to optimize further.

The user may also calculate the slopes of their pain lines, to better understand how the user, as an individual, feels and processes pain.

The app calculation module, in some embodiments, is able to find a distribution for the user's registered pain levels in specific body parts, either registered pain levels in general or registered pain levels after specific registered events, and also to find a distribution for the user's registered pain levels on the whole, including all body parts, either registered pain levels in general or registered pain levels after specific registered events. The user can save the distribution in their remote program and set their remote program to send them an alert after their nominated pain level in a body part specified by the user, during a specific time period, exceeds a certain percentile, decided by the user, of the user's previous nominated pain levels in that body part, during time periods of the same length.

In some of the embodiments in the $11^{th}$ group, the remote programs will include pain indicator virtual buttons, which a user can manipulate, to show that the user is feeling pain. If the user uses a pain indicator virtual button(s) to create a response, the PC on which the remote program is running will broadcast the response using its wireless broadcast capabilities.

Bayesian probability can be used as follows: It is sometimes not clear what the probability is of a user having a dangerous health condition. For example, it might not be clear what the probability is of a user being in danger of a heart attack within the next 24 hours. This is the "prior probability" of the user being in danger of a heart attack within the next 24 hours, and is usually low. This probability can be updated with the user's pain pattern. If other users with similar pain patterns had a higher-than-normal chances of experiencing heart attacks within 24 hours, then the user's probability of experiencing a heart attack within the next 24 hours would be updated, with the new information (the user's pain pattern) to create a new, "posterior probability"

of the user experiencing a heart attack within the next 24 hours. The posterior probability of the user experiencing a heart attack within the next 24 hours may still be low, but if it is high enough (For example 10%), the user may still wish to implement corrective measures and be prepared to go to the hospital.

Similar reasoning can be used regarding other health conditions. The prior probability of a user experiencing a health condition can be updated to a posterior probability of the user having that health condition based on the new information that is the user's pain pattern (Which the user would have been inputting). Note that the posterior probability of a user experiencing a health condition may be below 50% but still be high enough to warrant concern and preventative measures. The posterior probability can then be communicated to the user, using, for example, the app.

Therefore, for example, if the prior probability of the user having a heart attack within the next 24 hours is $\frac{1}{500,000}$, or 0.002%, but the posterior probability, given the user's pain pattern, of the user having a heart attack within the next 24 hours is $\frac{1}{100}$, or 1%, the user may wish to take preventative measures.

For this application's purposes, we can designate $p_{pr(co)}t$ as the prior probability of the user having a certain, specified, health condition co within time period t, and $p_{po(co)}t$ as the posterior probability of the user having the same health condition, given the new information of the user's pain pattern. The system can be programmed to send the user an alert where $p_{po(co)}t$ is higher than a certain threshold, which we will call thr(co).

In principle, the posterior probabilities of the user experiencing multiple health conditions can be added to each other, so that, for example, the posterior probability of the user, given the user's pain pattern, experiencing a heart attack can be added to the posterior probability of the user having a lung problem. The posterior probabilities of the user having other health conditions, given the user's pain pattern, can also be added. So, for example, for health condition 1 and health condition 2, the posterior probabilities $p_{po(co1)}t$ and $p_{po(co2)}t$ of the two health conditions can be added, and the system will send the user an alert if the combined posterior probability is higher than a certain threshold.

This approach is also obviously cheaper and can be used for a larger population of users than having medical personnel monitor the users continually and diagnose the probability of each of thousands or millions of possible health conditions.

The app calculation modules in some embodiments in the $11^{th}$ group can calculate the differences between a user's pain distributions of registered responses created during two different time intervals, using maximum mean discrepancy criteria. In some embodiments in the $11^{th}$ group, the app calculation module can also use a two-sample Kolmogorov-Smirnov test, to analyze the differences between the user's pain distributions created during two different time intervals. Expanded versions of the Kolmogorov-Smirnov test, in some embodiments, can be used to analyze the user's pain distributions created during more than two time intervals.

Some of the embodiments in the $11^{th}$ group, using individual databases, are also capable of performing the other tasks listed herein, which embodiments that use individual databases are discussed as capable of performing.

The Twelfth Group of Embodiments

The twelfth embodiment group uses a centralized integrated database (10), in which the registered responses, and preferably registered events, for multiple users are stored. Most embodiments in the twelfth embodiment group also use the centralized program (45), which will receive users' registered responses and store them in the centralized integrated database and in the users' individual databases. The part of the centralized program (45) that, in most embodiments, is responsible for receiving the registered responses from multiple users, and placing them in the centralized integrated database (10) and the users' individual databases is the centralized receiving module (30). The centralized calculation module (28) performs statistical analysis on the registered responses and other information in the central integrated database, and sends the results of the statistical analysis to the integrated statistical display (27). In most embodiments, researchers can also input commands into the centralized calculation module (28) about the kinds of statistical analysis the researchers want to be performed, and about a) Which registered response data, from the central integrated database, the researchers want to perform the analysis on, and/or b) Which users will be the sources of the registered response data which the researcher wants to analyze. Researchers can also input commands about graphs that they want to create, based on the registered response data, in the central integrated database into the centralized calculation module (28), and the centralized calculation module (28) will create the graph(s) and send them to the integrated statistical display (27) to display to the researcher(s).

The centralized calculation module (28), in some embodiments, will be able to fit a distribution to a set of registered responses from one of the Databases. The distribution could be normal, or have another form. Some examples of possible other forms are lognormal, and exponential, distributions.

The centralized calculation module (28), would also be able to calculate skewness and kurtosis of a group of registered responses.

The centralized calculation module (28) should ideally be able to create every kind of graph, concerning registered responses, that is known in the prior art. Some of the graphs it should be able to create are bar graphs of a group of users' nominated pain levels in the same situation, and line graphs showing how a user group's average nominated pain level changed during and after a registered event, where the user group's members were selected based on characteristics in their individual information, and the characteristics were found through a text search of the individual information.

Some of the calculations the centralized calculation module (28) should be able to make include finding differences between two different groups of registered responses (Of two different groups of users in the same time interval or different time intervals, or the same user in different time intervals) using maximum mean discrepancy criteria. In some embodiments in the $12^{th}$ group, the centralized calculation module can also use a two-sample Kolmogorov-Smirnov test, to analyze the differences between two different groups of users' registered responses in the same time interval or different time intervals, or the same user's registered responses in different time intervals. Expanded versions of the Kolmogorov-Smirnov test, in some embodiments, can be used to analyze more than two different groups of users' registered responses in the same time interval or different time intervals, or the same user's registered responses in two different time intervals.

The centralized calculation module should also be able to calculate the mean, mode, median, and standard deviation of a group of nominated registered responses, and to calculate pain lines, and areas thereunder, and pain shapes, and volumes therein, for individual users, and pain lines and pain shapes where coordinates for the pain line and/or borders of the pain shape are based on time for one dimension and a descriptive statistic based on a group of user's registered responses in another dimension. An example of such a descriptive statistic is a user group's average nominated pain level.

In most embodiments, researchers should be able to use the centralized calculation module to apply a refining function to a set of registered responses, and to alter parameters A-G regarding the analysis, and the centralized calculation module will be capable of applying the refining function.

The integrated statistical display will display, to researchers, the results of the calculations and graphs that the centralized calculation module sends to the integrated statistical display.

The invention also can be used to reduce average pain patients suffer resulting from medical or dental techniques.

One embodiment of the invention, in the $12^{th}$ embodiment group, includes a large number of input devices, potentially including PCs with remote programs that include pain indicator virtual units, and other input devices with ID input ports, wherein a user can enter their user ID into one of the PCs or other input devices. Then each user can enter their responses into the input device(s) where that user has entered their user ID. When each user is finished using an input device, they can enter their user ID into another input device, and enter responses into that new input device.

All responses will be received by the centralized receiving module (24) and placed by the centralized receiving module in the centralized database (10). If a response is identifiable by the user who made the response, that response will be placed in that user's individual database by the centralized receiving module.

The centralized receiving module will save individual information for the users in the centralized receiving database, and save individual information for each user in that user's individual database.

In some embodiments, users can also import individual information into the centralized integrated database by copying the individual information from another program such as a calendar app, or by entering it directly into the centralized integrated database, or through other methods.

Researchers can use the centralized calculation module (28) to perform statistical analysis on, and create graphs related to, the registered responses in the centralized integrated database. A researcher can select a subcategory of the registered responses in the centralized integrated database on which to perform the analysis, or from which to create the graphs. Some of the analyses will attempt to find relationships between users' registered responses and users' individual information.

The centralized calculation module (28) will send the results of the analyses, and the graphs, to the integrated statistical display, where they will be shown to the researchers.

A user can also use their remote program to statistically analyze, and create graphs concerning, the registered responses and individual information in the user's own individual database, and in individual databases of those other users to which the first user has been granted access.

If the first user has been granted permission, the first user can also use the first user's remote program to statistically analyze, and create graphs concerning, the registered responses in the centralized integrated database, to hopefully discover useful statistical relationships.

The remote programs should have, as components, app input modules (36) that users can use to command the remote programs' app calculation modules. The app calculation modules (22) perform statistical calculations, and execute other functions discussed herein. The app transmission module, which is part of the calculation module can send the results of the calculations the app calculation module performs to the app display module (25) for the user using the app to view. The remote program (20) will also include an app receiving module (24) that receives responses, and/or environmental information, and/or individual information, and places them in app database(s) for further analysis.

Some of, the remote programs (20) in this embodiment will also include app coordination modules (23).

In some embodiments, a user can use their app calculation module, or the centralized calculation module, to find a distribution for their pain levels, either in general or after registered events. Then the user can save the numbers in their remote program. and set their remote program to send them an alert after their pain exceeds a certain percentile of their previous pain levels. In some embodiments, the user may need to look at the raw numbers and copy the raw numbers into their remote program.

In some embodiments, the app calculation module and/or the centralized calculation module can look at the average and standard deviation and skewness of an individual's registered responses vs. registered responses for a part of, or all of, the user population.

Use of Bayesian analysis is also more effective, once a centralized integrated database is being used, because the centralized calculation module (and in some embodiments, app calculation modules) can find what pain patterns correlated to health conditions using a dataset of many other users' registered responses, and use this information to find which pain patterns have a probability above a threshold of indicating a current or future health condition for an individual user.

The use of individual profiles and individual databases for each user might highlight physiological differences between users, and allow greater understanding of the causes of those differences.

Method of seeing if a person has more pain sensitivity than normal by comparing his rate of pain for different kinds of things to normal.

Variance of pain vs. regular amounts of pain for most people for the same thing.

If can tell the difference between regular and individual pain reporting, maybe can sound alarms based on individual pain reporting.

If can tell the difference between regular and individual pain reporting, maybe can sound alarms based on individual pain reporting. Maybe can also note that a person is pain-sensitive.

Use of app calculation module (23) and patients' alarms to tell relatives about what is going on with their pain.

Maybe use individual standard deviation to detect individuals who are not very pain-sensitive?

Kurtosis of the distribution of a user's responses or users' responses can also be calculated to help find when a registered response or group of registered responses is cause for a user's alarm, by adjusting to see if a response is far "out there" compared to rest of the distribution.

Maybe learn something from kurtosis of the distribution of users' responses.

Correlate pain in different body areas, correlate it with age, gender, etc. and see if there is a difference. Also correlate pain at different points in time, other different conditions, etc.

Average amount of pain reported each hour or day after an operation, with standard deviation. If user reports pain in a high percentile, make alert.

Averages of intensity of pain reported, when it is reported, in different times for an operation and after the operation.

Can also do it by location, avg. intensity of pain for each location for the operation and after.

One Way the Individual Databases May be Configured

In some embodiments, each user inputs that user's individual information when the user creates an account with the invention and establishes an individual database. Alternatively, when the user creates an account with the invention, the user's individual information can be transferred from another source, or can be imported into the user's individual database and the centralized integrated database with a variation of the Iforms invention.

The user's individual information, no matter how it is inputted into the centralized integrated database and the user's individual database, will then be saved in the centralized integrated database and the user's individual database.

The user's individual information can include, among other information, the user's name, age, height, weight, ethnicity, gender, and the names of any health conditions the user has and/or had in the past, and the names of types of operations that the user experienced in the past. Information that is easily recognizable as belonging to a certain category, such as the user's birthdate, is placed in that category.

In some embodiments, every entry into the user's individual database, and the centralized integrated database, will include copies of the user's individual information.

Differences Between Individual Pain Patterns and Group Pain Patterns

In some embodiments, differences between an individual's pain patterns and pain patterns of users as a group may potentially be used to find whether an individual is more sensitive than usual to pain, as discussed elsewhere herein. In some embodiments, the centralized calculation module can find what percentile of users' responses, reflecting a specific body part, at a specific time, correlate with a chance, greater than a threshold, of the user having an urgent health condition. Then, once the percentile is known, the centralized calculation module can find what pain degree, etc. would correlate to the same percentile of a specific individual user's responses. This might help users to learn when their pain patterns indicate potential urgent health conditions, while the invention's components adjust their recommendations for the individual pain sensitivity of individual users.

A healthcare provider might also create altered treatment plans for an individual patient/user suffering from a health condition, that is less likely to result in high-volume pain shapes for that user, and/or more likely to result in low-volume pain shapes for that user, if A. The healthcare provider examines the patterns of which treatment plans for the same disease condition have tended to correlate with higher pain shape volumes for users, and which treatment plans tended to correlate with lower pain shape volumes for users, and B. The healthcare provider then modifies the user's planned treatment plan to include some of the characteristics as the low pain shape-volume treatment plans.

In some embodiments, the healthcare provider can further personalize the treatment plan, if enough data pertaining to the individual user is available, by finding what actions/conditions correlated to higher and lower pain levels for the individual user, respectively, in the past, and modifying the treatment plan to avoid characteristics that correlated with higher pain volume for the user, and emphasize characteristics that correlate with lower pain volume for the user.

Using the Central Calculation Module to Automatically Discover Pain Patterns' Significance In some embodiments in the 13th group, the centralized calculation module (22), acting independently, without direction from a researcher, will examine and test relationships between items in a user's individual information, listed in the centralized integrated database (10), and the user's pain patterns. Health conditions are one kind of such items. The centralized calculation module will not inform researchers of its findings unless it finds a statistical relationship with strength that exceeds a defined threshold. If the centralized calculation module finds such a relationship, the centralized calculation module can then inform human researchers of the relationship, and the researchers can then examine the relationship more and see if the relationship is worth reporting to the public or healthcare professionals. The threshold (s) can be defined ahead of time by researchers.

In some embodiments, the centralized calculation module (22) will search through the centralized integrated database (10) for terms, such as words or phrases, in users' individual information, and will pick a term (The "selected term"). Once the centralized calculation module (22) picks a selected term, the centralized calculation module will keep searching through the centralized integrated database to identify as many individual users (The "auto-detection users") who have the selected term in their individual information as possible. Then, the centralized calculation module (22) will perform a series of statistical analyses on the auto-detection users' expressed information, or components thereof, from before and after and during the times the selected term appears in the auto-detection users' individual information. The statistical analyses will include, but not be limited to, fitting statistical distributions to the pain the auto-detection users experienced, in different body parts. This can include finding statistical distributions of the pain the auto-detection users experienced, in different body parts at various points in time, before and after the selected term appears in the users' individual information. For example, the centralized calculation module can find a distribution of the pain the auto-detection users experience in their legs 1 hour before the selected term appears in their individual information, in their legs 0.5 hours before, etc. The centralized calculation module can also find distributions of the pain the auto-detection users experienced in their body parts at different amounts of time before and/or after the selected term appeared in the auto-detection users' individual information. The statistical analysis will also include comparing the distribution of auto-detection users' pain patterns, during defined time periods before, after, and during the time the selected term appears in the auto-detection users' individual information, to the distribution during the same time periods of pain patterns in the general population of users, and to the distribution of pain patterns of users who are not auto-detection users but who have selected individual information in common with the auto-detection users, such as users of the same age as the auto-detection users. This will include comparing the distribution of registered responses, at certain points, of the auto-detection users to the registered response distributions of the two aforementioned populations over a series of time frames, such as comparing the distribution of registered responses for the auto-detection users 30 days before the selected term appears in the auto-detection users' individual information, to the distribution of registered responses of the two aforementioned populations at that date and time. The centralized calculation module (22) may also comparing the registered reading distributions of the auto-detection users to the two aforementioned populations at other points in time, such as 20 days before, 10 days before, 1 day before, 30, 20, 10, and 1 hours before, 30, 20, 10, and 1 minutes before, 30, 20, 10, and 1 seconds before, and 30, 20, 10, and 1 seconds after, and other times. The statistical analysis will also include analysis of variance, and chi-squared analysis comparing the pain patterns of auto-detection users, to users in the two aforementioned populations, to see if there are differences that have predictive value or value for improving care by healthcare providers or care-givers. The centralized calculation module (22) can use any of the statistical methods discussed herein, including, but not limited to, two-sample Kolmogorov-Smirnov tests and Bayesian analysis, to detect such differences.

If the centralized calculation module (22) finds that one of these differences exceeds a pre-defined threshold, the centralized calculation module can inform researchers using any of the methods known in the prior art, including, but not limited to, sending the researchers an email or giving the researchers an alert.

Human researchers can then examine the matter further and see if the correlation is worth examining or reporting.

The centralized calculation module (22) can also select combinations of environmental variables, find users who experienced those environmental variable combinations, in the centralized integrated database, and find whether there are differences between the pain patterns of these auto-detection users, and the general population, in the same manner. The centralized calculation module (22) can then inform researchers when the centralized calculation module has found a relationship that exceeds a certain threshold, in the manner described above. This may help find conditions where environmental variables are injurious to human health.

Because the centralized calculation module is a computer program and not human, it can essentially keep testing statistical relationships endlessly until it finds a potentially useful relationship. Then it can keep testing statistical relationships endlessly again until it finds another potentially useful relationship, etc. It is assumed that some of the relationships the centralized calculation module finds will not be useful when examined closely by human researchers, but some of the relationships the centralized calculation module discovers will be useful.

The Thirteenth Embodiment Group

The thirteenth group of embodiments involves users using the remote program (20) as essentially an "app" on their PCs (42) to make others aware of their pain. First, the remote program running on a PC can contain one or more pain indicator virtual units (35). A user can use the pain indicator virtual units (35) to indicate that the user is feeling pain, and the location and degree (and sometimes type) of the pain, in any of the ways discussed in this application.

The PC's wireless broadcast capability will broadcast the user's registered responses. In some embodiments, these registered responses are sent over the internet to the centralized program and recorded in the centralized integrated database and an individual database (11) for that user.

In some embodiments, the remote program (20) will have security features to ensure that a certain individual user is the one using that particular centralized program to register responses, and use the remote program (20)'s other features.

In some embodiments, the registered responses that a user makes, using a specific remote program (20), will also be saved in an app database (44) for that user, on the PC where the remote program is running.

The user, in some embodiments, can also use the app calculation module (22) to make calculations concerning the user's own registered responses, and create graphs using their own registered responses, to learn more about the pain that they feel, and what causes that pain. The particular app calculation module (22) can perform as many of the types of calculations on the user's responses that are discussed in this application and that the user's particular app calculation module and PC are capable of performing. The app calculation module can perform these calculations on the responses in an app database (44), or in some embodiments, in an individual database (11) or the user's responses in the centralized integrated database (10). The app calculation module (22) will send the results of the calculations and the graphs to the app display module (25), which will send the results and graphs to the user.

In some embodiments, a user can set their remote program to send the user an alarm signal when a quantity related to the user's registered responses exceeds a threshold. The "quantity", here, can be expressed as a relationship between other quantities, if necessary, in some embodiments. The user inputs the quantity into the remote program (20). The app calculation module (22) will calculate the relevant quantity's magnitude, and will detect whether the quantity exceeds the threshold. Examples of the quantity can be the user's nominated registered pain level, in a body part, or the user's average pain level in that body part expressed over the course of an hour.

The numerical results of statistical calculations concerning the user's responses are examples (not the only possible examples) of quantities wherein the remote program can send an alarm signal to the user when the quantity exceeds the threshold. Some illustrative examples of numerical results of such calculations where, when the numerical result exceeds the threshold, an alarm signal can be sent to the user are A. The user's average pain level in a selected body part, in the last complete hour before the present. The threshold, here, can be a certain number for the average pain level in that body part. B. The user's moving average pain level over 10 nominating periods in a selected body part. The threshold, here, can be a certain number for the moving average pain level. C. The slopes of the user's pain lines for 2 different body parts. The threshold, here, can be specific numbers for the slopes of both pain lines, where if both of the numbers are exceeded, the alarm signal is sent. D. The chance, based on Bayesian analysis of the user's pain pattern during the past 12 hours being associated with a broken bone. Here, when the chance based on Bayesian analysis exceeds a certain number (the threshold) the alert signal is sent to the user.

In some embodiments, a first user can give remote programs (20) owned by specific second users (such as health-care providers) direct access to the first user's individual database (11) and/or the first user's registered responses, as the registered responses are made.

A second user can then perform all the types of statistical analysis on the first user's registered responses that the first user could perform. This may benefit the first user in numerous ways, some of which are discussed below. First, if the second user is a healthcare provider, such as a dentist or physician, the second user may, because of training, experience, and other factors, be more capable of analyzing statistical information concerning the first user's registered responses than the first user. Second, and related, if the second user is receiving registered responses from multiple first users, the second user may be better able to notice trends and other patterns that the first users have in common, which may help the second user to detect potential problems that multiple first users are experiencing, that the first users' registered responses show. A second user who detects one of these problems among multiple first users can then inform all the first users about the problem. A second user who is focusing care on a relatively limited group of first users may be able to provide them with more "personally customized service". Third, and related, a second user who perceives that multiple first users seem to be experiencing a similar change in their registered responses, such as a similar increase in the pain degree in their registered responses, may be more able and willing to contact these first users, find more about the pain these first users are feeling, detect whether the first users have potential health-threatening issues, and advise the first users about how to fix the issues that are causing them pain. Fourth, related, a second user might be more knowledgeable about the well-being of a comparatively small user group, and able to detect problems shown their registered responses, than the second user might be about the well-being of users in general. Likewise, the second user may be able to give the first users more "personalized" feedback related to their registered responses. For example, if the second user has access to the registered responses and individual databases of 10 users who are the second user's clients, the second user can probably give more personalized feedback than a researcher who is examining data patterns involving hundreds of thousands of users. Fifth, related, the second user may be likely to be more able to detect problems that may affect a "localized" group of first users than researchers who may have to examine a very large user group' data. Sixth, related, a second user who is a very specialized caregiver (Such as a specialized physician) may have contact with multiple first users who have a rare condition, be aware of the rare condition's known effects, and may be able to study their registered responses to gain more insights into the rare condition's effects and how to alleviate its negative effects. Researchers examining large numbers of users' responses may not be aware of the need to examine the responses of users who have some rare conditions, to gain insights.

The second user, in some embodiments, is also able to "combine" data from multiple users to make calculations and create graphs. For example, in some embodiments the second user may be able to pick nominating periods, and average the nominated registered pain levels of multiple first users, and/or to map the distribution of the first users' nominated pain levels by percentiles. The second user may also be able to graph the nominated pain levels of multiple first users on the same graph, and detect whether one first user's nominated pain levels are significantly higher than those of others, by being in a higher percentile, by having a higher average, or by being clearly higher for other reasons. The second user may then wish to contact this first user, to try to find out why this first user has higher pain levels and/or to try to alleviate this first user's higher pain levels.

In some embodiments the second user is able to place the registered responses from multiple first users, who have given the second user access to their registered responses, together in an app database (44) for the second user to examine further, and create graphs and make calculations based on the combined data.

In some embodiments, the first user can, using the methods herein, enter permission into the first user's remote program for the first user's remote program to communicate with a nearby coordination module or app coordination module, so that the nearby coordination module or app coordination module can command the first user's remote program to make a specific alarm signal if the first user registers a pain degree higher than a certain level, through one of the pain indicator virtual units (35) in the remote program (20) running on the first user's PC. The alarm signal can be of a type pre-loaded into the first user's remote program (20) or, in some embodiments, of a type the first user can record or upload into the first user's remote program (20), as long as the nearby app coordination module or coordination module has commanded the other remote programs and input devices that have given similar permission to make different alarm signals.

In some of these embodiments, the user will enter permission for the remote program (20) to automatically communicate with any app coordination module or coordination module in certain situations, such as when the device running the app coordination module or coordination module reaches within a certain range of the device running the remote program. In some embodiments, the remote program may be designed so that the user will have to enter permission for the remote program to communicate with each specific coordination module and/or app coordination module within range.

Other embodiments within the thirteenth embodiment group are possible.

Other Embodiments

Embodiments involving characteristics of one or more of the above embodiment groups are possible. For example, embodiments involving multiple solar cells connecting to battery chargers in human body models that have transmitters and send information indirectly to the centralized integrated database (10) and also involving some users using remote programs (20) with virtual pain indicator units (35) running on PCs (42) to transmit their registered responses directly or indirectly to the centralized integrated database (10) and also to app databases located on healthcare providers' PCs (42) is possible.

Any functional combination of the invention's components, used to record and analyze the pain users experience, is part of the present invention.

A user can theoretically have one or more human body models, one or more part models, one or more mouth models, one or more proxy models, or some combination of these, that are portable, and that the user carries around. The human body model(s), part model(s), and mouth model(s) can be attached to clothes or jewelry, or something else. One or more of these can also include a cover(s) for the pain indicator units therein, so that the pain indicator units are not pressed accidentally.

Correcting for Variations in Individual Users' Perceptions

It might be possible to correct for variations in individual users' perceptions by looking at the user's pain patterns within the centralized integrated database, and seeing how they compare to registered responses of the user population on the whole, or user subpopulations to which the user belongs.

Some Uses of K-Means Modeling with the Present Invention

K-Means modeling is a system where data points are placed on a graph and divided into "clusters" by minimizing the distance between the data points in each cluster and the cluster's "centroid". There are multiple measurements of "distance", but the most common is Euclidean distance. The Euclidean distance between two points on a graph is the square root of the sum of the squared distances in each dimension the graph covers. In K-means clustering, potential "centroids" of clusters of data points are assigned at the beginning, and the distance between each data point and the nearest centroid is calculated. Then the correct centroids of the clusters are calculated based on finding a point for each cluster where the combined Euclidean distances from that point to each of the points in the cluster is minimized, and the Euclidean distance of each data point from the centroid of its cluster is recalculated. Then a new centroid of each cluster is assigned if needed, and the Euclidean distance of each data point from the new centroid of its cluster is recalculated to minimize the combined Euclidean distances from the new centroid to each of the points in the cluster. This repeats until there is no change in the centroid locations. The "K" in K-Means is the number of clusters.

K-means modeling could potentially be used together with the responses registered on signaling models by either the entire population of users, or a subpopulation of users, to draw conclusions about what parts of the body experience pain in certain situations, and possibly to prescribe or alter treatment plans, diagnose disease, or draw conclusions about disease's effects on populations or individuals.

A subpopulation of users could share common characteristics, such as having a medical condition in common, or having experienced the same kind of recent medical operation. The subpopulation, or a sample of that subpopulation, could use a group of input devices to create responses, on which a K-means analysis can be performed, to show the degrees, types, and locations of the pain experienced by users with the common characteristics, and how those degrees, types, and locations change over time.

One way a system based on K-means modeling can be used is that data points representing responses given by a subpopulation of users who have some common characteristic, or a sample of the subpopulation, can be placed on a 2-dimensional or 3-dimensional display of all or part of a human body. Each response is a data point, and is placed on the graph on the body part where the user who gave that response indicated that he/she felt pain.

The responses being plotted can be responses that the subpopulation of users gave during a certain defined time period, such as the nominated pain level that each user in the subpopulation expressed during the first hour after that user experienced a specified event that the users in the subpopulation have in common (Such as a surgery experienced by all users in the subpopulation). Then centroids can be plotted for the responses, and the centroids can be displayed on the screen being used.

Afterwards, centroids can be plotted for the nominated pain levels of the users in the subpopulation during the next defined time period (such as the next hour), then repeated for the nominated pain levels of the users in the subpopulation during the defined time period after that (Such as the hour after that, where the hour is the defined time period, or the nominating period after that, or the timestretch after that), etc.

The centroids for the subpopulation's responses during the first defined time period are shown on the display, and then the centroids for the subpopulation's responses during the second defined time period, etc. can be quickly shown on the display. The centroids will be seen to "move" on the display as the responses given during each defined time period change, and the caregivers who view the centroids, how they move, and the locations in the body to which they move at different times.

For example, a population of users who are experiencing a certain medical condition can give responses, where each response includes a location where a user is feeling pain, and the pain degree that user is feeling, during a specific time period, such as each hour, each minute, etc. If needed, a nominating rule can be put in place to pick each user's nominated pain level in each body part where the user expresses multiple pain levels for that period. In our example, the nominated pain level is the highest pain level registered for each body part during each 24-hour period, starting with, "Day 1" (Beginning at midnight the day after diagnosis and ending at midnight the next day), the first full 24-hour period after each user is diagnosed with the medical condition. The responses' locations and degrees can then, in an electronic display, be superimposed on a picture of a human body, a human body display. Each response would be a data point. Then, a KNN analysis can be run, to find the data points' "centroids" during "Day 1", and to group the data points into "clusters" (Here the kinds of input devices the users used to register responses are likely to heavily influence the "cluster" identifications, which limits the cluster identifications' usefulness). The centroids' locations will still be useful and the clusters' identities may also be used to generate insights). The centroids would then be displayed on the human body display. Afterwards, the process can be repeated on "Day 2", Day 3", etc. Each user's response for each Day, that included the nominated pain level for each body part, which is the highest pain level that user registered for each body part on that "Day" ("Day 2", Day 3", etc.), and including the location and degree of that response, will become a data point for that "Day". Then, the data points for each Day, is superimposed on a human body display, and centroids for that Day is calculated. The centroids may move from Day to Day, because the locations and degrees of the responses used to calculate the centroids' locations for each day may change. Researchers will be able to observe how the centroids move from Day 1 to Day 2, etc., and possibly over the course of longer periods, such as how the centroids move from Day 1, Day 2, etc. up to Day 300, if the researchers desire. Researchers may then be able to draw conclusions from the centroids' location and movement about how people generally experience pain, and how their pain changes, after they were diagnosed with that specific medical condition. If a certain user is experiencing pain with a location and/or degree that is significantly different from the types of pain people generally experience after they were diagnosed with that specific medical condition, that user, or his/her healthcare providers, might wish to examine the user's physical state more to find the reasons for the difference.

A similar analysis can be done if the nominating rule or nominating period changes, or if the users in the population have a different type of event(s) in common. For example, if the users all worked on a construction site, or were all in automobile accidents, or were all hit on the head, these are all events in common that users might have, for which researchers might wish to examine how users' pain develops over time after the event happened.

A similar analysis can also potentially be done if the users don't have any event(s) in common, or if the time since an event have in common varies between the users, though researchers will have to plan carefully to eliminate potential problems with such an analysis.

The invention can be used, together with Knn analyses, to help users in other ways, for example:

Knn with time as independent variable and each dimension for where pain can be reported.

For example, each reading of pain at a certain point on each of the human body models can be a data point. Then, a KNN model can be made using those data points, and a picture of a human body can be superimposed on the data points to see how the clusters and their centroids move.

KNN with generally calculating how pain falls into categories and categorizing a new case of a patient's reported pain by which category it falls into.

In one type of KNN analysis, if there are a number of data points for a shoulder, and then the KNN model shows that one of the centroids is in the shoulder, then the centroid can be shown on a graph of the human body that is shown on a computer.

In one type of KNN model, the different locations of pain indicator units are each given coordinates along the Y-Axis and X-Axis. Then, when the user activates each of the pain indicator units, another data point is created with the X-coordinates and Y-coordinates designated for the pain indicator units being activated. This creates a pattern of data points that can be plotted on the graph. Then the data points are grouped into clusters and centroids are found for the clusters.

This process repeats. Eventually the centroids' locations are found. These locations might be the pain's sources. The patient might also go through physical therapy to see if, afterwards, he or she activates the pain indicator unit in a different pattern, creating a different pattern on the graph with different centroids.

Some other ways of using KNN analysis, related to the above, are:

Centroids move with time. Find centroids for each period, then the next period, then see how they move.

Individual user-Just figure out where the centroids are. See what that means about disease pathology and diagnosis.

Individual-multiple periods. See how the centroids move. See what that means about disease pathology and diagnosis.

Group-Figure out where centroids are and how they move and see what that means about disease pathology and diagnosis.

One method of KNN modeling using responses and the responses' degrees to track the most common locations of pain in certain locations.

The invention can be used, together with KNN analyses, to help users in other ways. KNN analysis is often used to decide which cluster a new "observation", or data point, falls into, based on the new data point's distance from the clusters' centroids on a graph. In these models, a new data point is classified to be in a cluster based on the centroid to which the new data point falls nearest. Computers are also capable of running KNN analyses in more than three dimensions.

The below can be achieved by the app calculation module (22) running on a PC of sufficient capacity can achieve the below, or by the centralized calculation module (28) running on a computing system of sufficient capacity, or by another method. In one version of the invention, a user seeking a diagnosis's nominated pain levels in different locations based on the user's registered responses, during each nominating period will be combined to make a data point for that nominating period and user. Each location for which the user registered a response during the nominating period is one of that data point's "dimensions". The user's nominated pain level based on the responses the user registered for each location is the data point's "coordinate" in that dimension. For example, if the user's nominated pain levels in one 1-hour nominating period were pain with degree 3 in his left arm, pain with degree 2 in his right arm, pain with degree 3 in his chest, and pain with degree 5 in his neck, the coordinates of the data point representing the user's responses in that nominating period are 2 in the dimension representing the left arm, 2 in the dimension representing the left arm, 3 in the dimension representing the chest, and 5 in the dimension representing the neck, or 2, 2, 3, 5.

A large number of previously collected data points, each representing the nominated pain levels that a user experienced in the same body parts, will then be used for comparison, essentially as a "training set". The users who generated these data points will have experienced, and been diagnosed with, known health conditions. These data points could possibly be uploaded from the centralized integrated database (10) or a specialized database (33). The training set data points could potentially be "filtered" to find those that have other characteristics in common, for example, the users who made the data points in the training set could be of the same gender, or the same race, or the same age range, or the same height range. The training set data points could be filtered via the component doing the KNN analysis (The app calculation module or centralized calculation module) searching the training set data points and selecting only those that include the desired characteristics. These characteristics should probably also be characteristics the users who contributed the training set data points have in common with the user seeking a diagnosis. The training set data points should also probably be calculated using the same nominating rule and nominating period as the data point for the user seeking the diagnosis.

The training set data points are divided into clusters depending on what health condition each user who contributed a data point in the training set experienced. For example, users with latent heart attacks may be placed in one cluster, while users with other kinds of chest-related problems may be placed in other clusters. The centroid of each cluster will be calculated. Then the app calculation module or centralized calculation module being used on a PC or other type of computer running the KNN analysis will place the "new" data point, the nominated pain levels created, in a specified time period (Such as a certain day), of the individual user who is seeking a diagnosis, in the cluster with the centroid to which the data point is closest, and will preferably also give an indication of how close the "new" data point is to that centroid. The PC or other computer will give this information to the healthcare provider(s) who wish to diagnose the user seeking a diagnosis.

The PC or other computer may also perform the same type of KNN analysis for more "new" data points the nominated pain levels of the user seeking diagnosis in other periods represent (For example the nominated pain levels on Day 2, Day 3, etc.) and determine and report the cluster(s) for the "new" data points, and how close these "new" data points are to the centroids of the training data set.

In some versions of the invention, the healthcare provider(s) can also try to compare the "new" data points, which will represent the user seeking diagnosis's pain levels during specific time intervals, to the pain levels experienced by the users who registered the pain levels incorporated into the data points in the training dataset at different times, for example, the healthcare providers might filter the training dataset to include some users who experienced a heart attack, and some users who experienced other chest conditions, and compare the data points incorporating the pain levels of the user seeking a diagnosis during the last 24-hour period to the data points incorporating the pain levels of users in the 24 hours before some users experienced a heart attack or one of the other chest conditions. If the data point incorporating the pain levels of the user seeking a diagnosis clusters with data points incorporating the pain levels of users who experienced a heart attack within 24 hours, the user seeking a diagnosis may wish to take precautions to avoid experiencing a heart attack.

The healthcare providers can also keep examining training datasets including data points incorporating pain levels of users who experienced other health conditions (Besides the health conditions the users in the initial training dataset experienced), to see if the pain levels of the user seeking diagnosis cluster better with the pain levels experienced by users who had one of these other health conditions.

In some versions of the invention, the app calculation module or centralized calculation module can simply inform the user seeking diagnosis about which cluster the user falls into, and the distance between the data point representing that user's pain levels and the cluster centroid, without involving human healthcare providers at all. This might motivate the user to go to the hospital, if needed, or make lifestyle changes, for example. This might also be very useful in situations when healthcare providers are overworked or unavailable. Note that having a computer program inform a user of what cluster the user falls into, and the distance between the data point representing that user's pain levels, is not, and is not intended to be, a substitute for a trained human interpreting the program's output.

In some versions of the invention, the app calculation module or centralized calculation module can also inform the healthcare providers about how the pain levels of the user seeking diagnosis change relative to the clusters in the training dataset by comparing the data points the pain levels of the user seeking diagnosis created with the data points created by the users in the training data set a specified time before or after a specific event. For example, if the app calculation module does the above KNN analysis for the data point representing the pain levels the user seeking diagnosis experienced 5 days ago vs. a training dataset including some users that experienced heart attacks 10 days later, and then does the above KNN analysis for the data point representing the pain levels the user seeking diagnosis experienced 4 days ago vs. a training dataset of the same users 9 days before some users experienced heart attacks, and then does the above KNN analysis for the data point representing the pain levels the user seeking diagnosis experienced 3 days ago vs. a training dataset of the same users 8 days before some users experienced heart attacks, and the distance between the data point for the user seeking diagnosis' pain levels, and the centroid for the cluster representing users who suffered heart attacks, keeps decreasing for each KNN analysis, then the user seeking diagnosis may want to alter his/her habits to try to avoid a heart attack.

Likewise, if the user seeking diagnosis registers his/her pain levels for several days after a specific event such as a surgery, and the training dataset includes some users who recovered without complications, and some users who had various forms of complications, a KNN analysis can be performed to see whether the user seeking diagnosis's pain levels for each day after the surgery cluster with users who had one of the complications. If they do cluster with users who had one of the complications, the user seeking diagnosis may wish to schedule a consultation with a healthcare provider quickly to avoid further problems.

In theory, this diagnostic clustering procedure can be performed while the user seeking diagnosis is at home, and the healthcare providers are at a hospital or other healthcare facility, as long as the user seeking diagnosis has the ability to register responses. The healthcare providers can download or otherwise access the responses and use the app calculation module (22) or centralized calculation module (28) to perform the above analysis. This can allow for immense savings on healthcare costs, and possibly many lives being saved, because users who have potentially dangerous conditions will sometimes receive early warning and get to the hospital in time for preemptive treatment, while users who likely do not have dangerous conditions may be able to find out about this quickly.

In principle, the app calculation module or centralized calculation module could send an automatic alert to the user seeking diagnosis if the app calculation module or centralized calculation module, respectively, detects that the pain levels the user seeking diagnosis felt are similar enough to pain levels experienced by users who experienced some major health condition. For example if the data point the pain levels of the user seeking diagnosis created is close to, or on, the centroid of a cluster representing users who experienced heart attacks, this would probably be called "similar enough" for the app calculation module or centralized calculation module to send the automatic alert.

The healthcare providers (Or the app calculation module or centralized calculation module) might also use different nominating periods and nominating rules to see what "cluster" the pain levels of the user seeking a diagnosis best fit into. A different nominating rule and/or a different nominating period may affect the locations of the data points for the user seeking a diagnosis and the locations of the data points in the training set. The healthcare providers (Or the app calculation module or centralized calculation module) trying to diagnose the user, who is seeking a diagnosis, can try multiple nominating periods and nominating rules until they find a nominating rule and nominating period that work best to find the cluster into which the user seeking diagnosis falls.

These methods can all, to some extent, be adjusted if the individual user seeking diagnosis experiences pain more or less than average. In one adjustment method, the previous registered responses of the individual seeking diagnosis can be compared to the registered responses of other users with the same health conditions, and if the user seeking diagnosis' previous registered responses show significantly more or less pain than the averages for registered responses of users with similar conditions to the user who is now seeking diagnosis (statistical significance at the 95% level could potentially be used to decide what is "significantly" more or less), the user seeking diagnosis' registered responses can be adjusted, either upward or downward, by the difference. For example, if this user seeking diagnosis previously registered a pain level of 4 when skinning his left arm, and the average pain level for users skinning their left arms is 5, with a standard deviation of 0.1 and a normal distribution, then the pain level the user registers in his left arm, in this example, can be adjusted upwards by 1 to reflect the fact that the user's left arm is particularly resilient. Therefore, instead of 2, 2, 3, 5, the coordinates of the data point representing the user seeking diagnosis would be 3, 2, 3, 5.

Some Uses of the Human Body Display to Detect Patterns Among Patients

KNN modeling could potentially be used together with a human body display (12) to make conclusions about what parts of the body experience pain in certain situations, such as the aftermath of certain operations, and how much they experience pain, etc.

Other models can be used. For example, a graph of the human body can be made that shows where people most experienced pain, in different colors. Areas where more pain data points were recorded can be shown in different colors. Knn with time as independent variable and each dimension for where pain can be reported A user may sometimes register a pain level in a body part, during a time period, and then be unable to keep registering the pain level for the remainder of the time period, while still feeling pain in that body part. For example, a user may use a pain indicator button to register a pain level of "4" at one point during a minute, but then stop pressing the pain indicator button because he/she has to do something else for the remainder of the minute. A researcher or other person who looks at a record of when the pain indicator unit was activated may erroneously conclude that the user experienced pain for part of the minute, but not all of it, and data analysis based on this conclusion may also be inaccurate.

This problem is much less important in situations when the goal is simply to communicate that the user is feeling pain, and the pain's location, and/or degree, and/or type. The researcher(s) or others performing data analysis using the user's responses may also choose to ignore this issue and specify they ignored it in any report.

Researchers may also choose to do their analysis based on a nominated pain level that each user expressed during each time period (The researchers would also pick the time period's length on which to base the nominated pain level), and use that nominated pain level in their analysis: For example, researchers may do their analysis using as their nominated pain level the highest pain level that each user in the targeted population expressed during each minute, or each hour, or each 24-hour day. Researchers may also use, as their nominated pain level, the average pain level each user in the targeted population expressed or registered during each time period, or the minimum pain level each user expressed or registered during each time period, or the median, or some other measure. The prior art allows retrieval of data from a database, based on the highest, lowest, mean, median, or other characteristics of the data from within one time period, such as one minute or one week.

The researchers should specify which measure and time period they are using, when making any report about their analysis.

Researchers may also address this issue by applying a "nominating rule".

For example, a nominating rule can be made that one of the pain levels the user expressed in his right leg during each minute (Here a minute is the "nominating period") shall be interpreted, during data analysis, as the pain level that user experienced in his right leg for the entire minute.

This scenario may require a use of "nominating rule" to define which of the multiple pain levels the user may have expressed in a body part during the nominating period is the nominated pain level.

In some embodiments of the invention, the users can use components of their remote programs (20) to each suggest a nominating period and/or nominating rule for their own responses. For example, in some embodiments, they could designate nominating rules using the app calculation module (22). This should not change the response data in any user's individual database, the centralized integrated database (10) or any specialized database (33) where the response data being examined is recorded, but the nominating periods and nominating rules should be additional information that is recorded in these databases.

If researchers use a nominating rule and/or nominating period in their analysis, the researchers should specify which nominating period(s) and nominating rule(s) are being used, the distribution of which nominating periods and rules are being used if more than one of either is used, and who (researchers, users, or someone else) decided on the nominating period(s) and nominating rule(s) being used, when making any report about the results of their analysis.

In theory, the entities maintaining the individual databases, centralized integrated database, and specialized databases could "impose" a nominating rule and nominating period on users, but the inventors herein do not believe this would be a good solution.

More Information about Using the Invention to Manage Chronic Pain Conditions and Nerve-Related Conditions The invention can help with management, and detection, of pain-related illnesses, and nerve-related illnesses, in the below ways, because the invention allows cheap, quick, accurate, precise compilation of data about the amounts of pain that users feel, and where they feel this pain, and helps users to track small changes in the amounts of pain they feel.

The invention can also be used to help individual neuropathy patient users most reduce their pain, first, by tracking individual patients' registered responses, so that a user can figure out the time periods when the user's distribution of pain in registered responses had the lowest distribution, or was measurably lower. Then the user can replicate or increase the user's activities during the time periods when the user's pain distribution is lowest, or lower. The user can also try to find the environmental variables that were correlated to lower pain distributions for the user, and arrange the user's life to experience these environmental variables more often. These measures will hopefully improve the user's quality of life.

Second, in some embodiments researchers using the invention, and using the centralized integrated database, can find what environmental variable values and/or individual information in other neuropathy patients correlated with their pain distributions being lower, or with their pain distributions being at the lowest level. The researchers can then make their findings known, so that the user or the user's health care provider can use their findings and the user can modify their life to perform more of the activities that correlated with lower pain levels, and experience more of the environmental variable values that correlated with lower pain levels.

The invention might also eventually help sufferers of nerve-related diseases, such as ALS (Amyotrophic Lateral Sclerosis) to detect their diseases, including ALS (Especially sporadic ALS, which has no known genetic component) early on, in the following way. The example of ALS is given: Through using the centralized integrated database, or the individual databases of users with ALS, and using the centralized calculation module, researchers might be able to find unusual pain patterns, that are correlated to a higher risk of ALS, or to the early stages of ALS. The researchers can then make their findings about these pain patterns known. Then researchers can use the centralized calculation module to analyze the response data and other information in users' individual databases, or even have the centralized calculation module automatically examine a large number of users' individual databases, to see if they have the pain patterns in question. Then, these users can be informed that they are exhibiting the pain patterns, that are correlated to a higher risk of ALS, or to the early stages of ALS, and these users can take appropriate measures, like seeing if they can reduce their susceptibility to ALS. Similar measures can be used regarding other nerve-related diseases.

The invention can also help sufferers of ALS, Ehlers-Danlos Syndrome, fibromyalgia, and chronic pain in general to manage their conditions, as follows.

First, a user who suffers from one of these diseases can use the app calculation module to examine their own individual database, and find, what individual information and environmental variable values, listed in their individual database, correlated with reduced pain levels. The user can then try to replicate this individual information and try to experience similar environmental variable values, to improve their quality of life.

Second, researchers can use the centralized calculation module to examine centralized integrated database, and find which individual information and/or environmental information correlated with reduced pain levels for users who had one of these diseases, such as ALS. This can be done even if the reduction in average pain per user was not large. Then, the researchers can make their findings known, and users with the same disease (ALS, in the example) can hopefully imitate the individual information or try to experience the environmental variable values that caused the environmental information. This will hopefully improve the users' quality of life and hopefully help them to live longer and reduce their diseases' impacts.

In theory, multiple "rounds" of improvement are possible, where a user tries to reduce their pain levels by modifying their lifestyle based on information from their individual database or the centralized integrated database, experiences reduced pain levels, and then tries to reduce their pain levels further by finding the individual information and/or environmental variable values in their individual database that are now correlated to their new lowest pain levels, and trying to replicate this individual information and/or experience these environmental variable values more often, after which the user's pain levels will hopefully be reduced further. Then the user can again find the individual information and/or environmental variable values in their individual database that are now correlated to their new lowest pain levels, etc.

The goal is for users to closely understand what correlates to their pain so they can reduce their pain.

Use of Artificial Intelligence (AI)

The artificial neural network that can be used with some embodiments of this invention, also referred to herein as the "neural network", shall be a network of programs (The artificial neurons) organized into multiple layers. Inputs based on users' observations of their pain will be run through the first layer, then the results of this are run through the second layer, etc., until the last layer is reached, and an output from the last layer is generated.

The artificial neurons that are part of this invention, each of which shall be referred to herein as an "artificial neuron", are the "nodes", connected programs that are part of the artificial neural network.

An individual's experience of pain, in response to stimuli, might be nonlinear, and it is important useful for us to understand the causes of an individual's pain even if these causes' effect is nonlinear.

The artificial neurons' weights in the neural network are some of the inputs in the neural network's calculations.

A set of users' registered responses, combined with their individual information, can be used as a "training dataset" for an artificial neural network. The responses can be taken from the users' individual databases or from the centralized integrated database. The artificial neural network will assign weights to its artificial neurons that minimize the "training loss function", which can be seen as a measure of the difference between A. The actual changes in users' expressed information, that happened when users in the training data set experienced combinations of specified changes in environmental variable values or the users' individual information, and B. The changes in users' expressed information the artificial neural network projected would occur when the users in the training data experienced the same combinations of specified changes in environmental variable values or a user's individual information.

Changes in the weights of artificial neurons in the neural network are used to estimate how much different factors, such as changes in environmental variables, influence the distribution of a user population's registered responses, or registered responses in different body parts, and the use of a neural network will try to trace how, and how much, the pain users experienced in different body parts changed as the users' individual information and the environmental variables to which the users were exposed changed.

In some cases the weights of the artificial neurons in the artificial neural network will represent components that are added together to create projected summary statistics of the registered responses of the users in the user population, or other information about these users' registered responses. The neural network will adjust the artificial neurons' weights to minimize the differences between what the neural network calculates should be the ways in which different changes in environmental variables and individual information influence a user population's registered responses, and the ways that the user population's registered responses change when environmental variables and the user population members' individual information change.

The neural network will then try to calculate proposed increments by which changes in environmental variable values and/or individual information result in changes in a user population's pain distribution. The proposed increments will be based on the weights and activation functions of the artificial neurons, that minimize the loss function. The artificial neurons' weights in the neural network are some of the inputs in the neural network's calculations.

These proposed increments can then be tested with response data, environmental information, and individual information from a second group of users. In some embodiments, both the first user group and the second user group can be selected from users who have a certain characteristic(s) in common, so that researchers can understand how the pain patterns of users with that characteristic are affected by changes in individual information and environmental information.

In a second use of an artificial neural network, a single user's registered responses can be used as the training dataset. The neural network can be used to investigate a "training loss function", which is the difference between A. The actual changes in the single user's expressed information, that happened when the user experienced combinations of specified changes in environmental variable values or the user's individual information, and B. The changes in the user's expressed information the artificial neural network projected would occur when the user who provided the training data experienced the same combinations of specified changes in environmental variable values or individual information. This may be particularly useful with chronic pain sufferers.

Changes in the weights of artificial neurons in the neural network are used to estimate how much different factors, such as environmental variables and individual information, influence the user's experience of pain in different body parts, and the use of a neural network will try to trace how, and how much, the pain the user experiences in different body parts change as the user's individual information and the environmental variables to which the user is exposed change.

In some cases the weights of the artificial neurons in the artificial neural network will represent components that are added together to create estimates of the user's registered responses. The neural network will adjust the artificial neurons' weights to minimize the differences between what the neural network calculates should be the ways in which different changes in environmental variables and individual information influence the user's registered responses, and the ways that the user's registered responses change when environmental variables and the user's individual information change.

These proposed increments can then be tested with response data, environmental information, and individual information from the same user at other times.

This might help an individual user to understand the variations in their own pain better, so that they can experience less pain.

In some embodiments, initial weights are assigned, either randomly, or by another method, to the artificial neurons in the neural network.

The Fourteenth Embodiment Group

The fourteenth embodiment group involves inventors using input devices with pain indicator skins (43). This may provide more precise information about users' pain. In some embodiments in the $14^{th}$ group, each small pain indicator unit in the pain indicator skin will indicate pain in certain body sections, and transmissions from that input device that show that a one of the small pain indicator unit(s) has been activated will include the markers for the sections for which that small pain indicator unit is supposed to indicate pain. The small pain indicator units themselves can be configured that the impulses they transmit will include the markers, or the markers can be added by another component of the input device such as a processor, before the input device transmits a response registered using the small pain indicator pieces. In some of the input devices, especially some human body models, the markers that the input device's transmitter broadcasts when one of the small pain indicator units is activated will be markers for the part of the human body that corresponds to the part of the human body model where the small pain indicator unit is located.

Other Embodiments

Other embodiments combining components discussed in different embodiment groups are possible, and may increase the invention's utility. For example, embodiments involving some input devices being placed on pain indicator pieces with suction cups, and also involving use of the centralized integrated database, individual user databases, and some individual users' expressed information being made available, with their permission, to other individuals users is certainly possible.

Furthermore, in some embodiments, some of the invention's computer program components may be combined, as long as their functionality is maintained in the combined computer program component.

The discussion included in this patent is intended to serve as a basic description. The reader should be aware that the specific discussion may not explicitly describe all embodiments possible, and alternatives are implicit, or obvious to those skilled in the art. Also, this discussion may not fully explain the invention's generic nature and may not explicitly show how each feature or element can actually represent equivalent elements. Again, these are implicitly included in this disclosure. Where the invention is described in device-oriented terminology, each element of the device implicitly performs a function. It should also be understood that a variety of changes may be made to the embodiments that have been described, without departing from the invention's essence. Such changes are implicitly included in the description. These changes still fall within the scope of this invention.

Furthermore, each of the various elements of the invention and claims may also be achieved in a variety of manners. This disclosure should be understood to encompass each such variation, whether it is a variation of an apparatus embodiment, a method embodiment, or a variation in any element of an embodiment. As the disclosure relates to the invention's elements, the words describing each element may be replaced by equivalent apparatus terms, even if only the function or result is the same. Such equivalent, broader, or even more generic terms should be considered to be encompassed in the description of each element or action. Such terms can be substituted, when desired, to make explicit the implicitly broad coverage to which this invention is entitled. It should be understood that all actions may be expressed as a means for taking the action in question, or may be expressed as an element for causing the action in question. It should also be understood that variations combining components of the invention that are listed separately here, and dividing components of the invention that are listed as one component here into two or more components are part of the present invention.

Similarly, each physical element disclosed should be understood to encompass a disclosure of the action which that physical element facilitates. Such changes and terms are to be understood to be explicitly included in the description.

The features, functions, and advantages that have been described herein may be achieved independently in various embodiments of the present invention including computer-implemented methods, computer program products, and computing systems or may be combined in yet other embodiments.

It is also important to note that some of the invention's utility stems from its ability to easily gather large amounts of data pertaining to individuals' pain, and pain felt by individual members of groups, and to help researchers, viewers, and other users to understand the causes of this pain, and the relationships between the pain and other conditions and events. Some of these relationships are presently unknown, but the invention will help to discover them so they can be used. The inventors also caution that correlation does not always indicate causation, and that it is sometimes possible to "fit" data to a statistical relationship that does not exist in reality, so some of the statistical relationships discovered using the invention may need to be investigated further, to be used effectively. The invention's helping to discover these relationships is one of the reasons for its utility.

The healthcare provider, in this embodiment, can also command the app calculation module (20) to give the healthcare provider an alert when a quantity discussed in the user's registered response data, or the results of the above analysis, reaches a certain level, such as when the pain level registered by one of the patients reaches a certain level.

Figure 11:
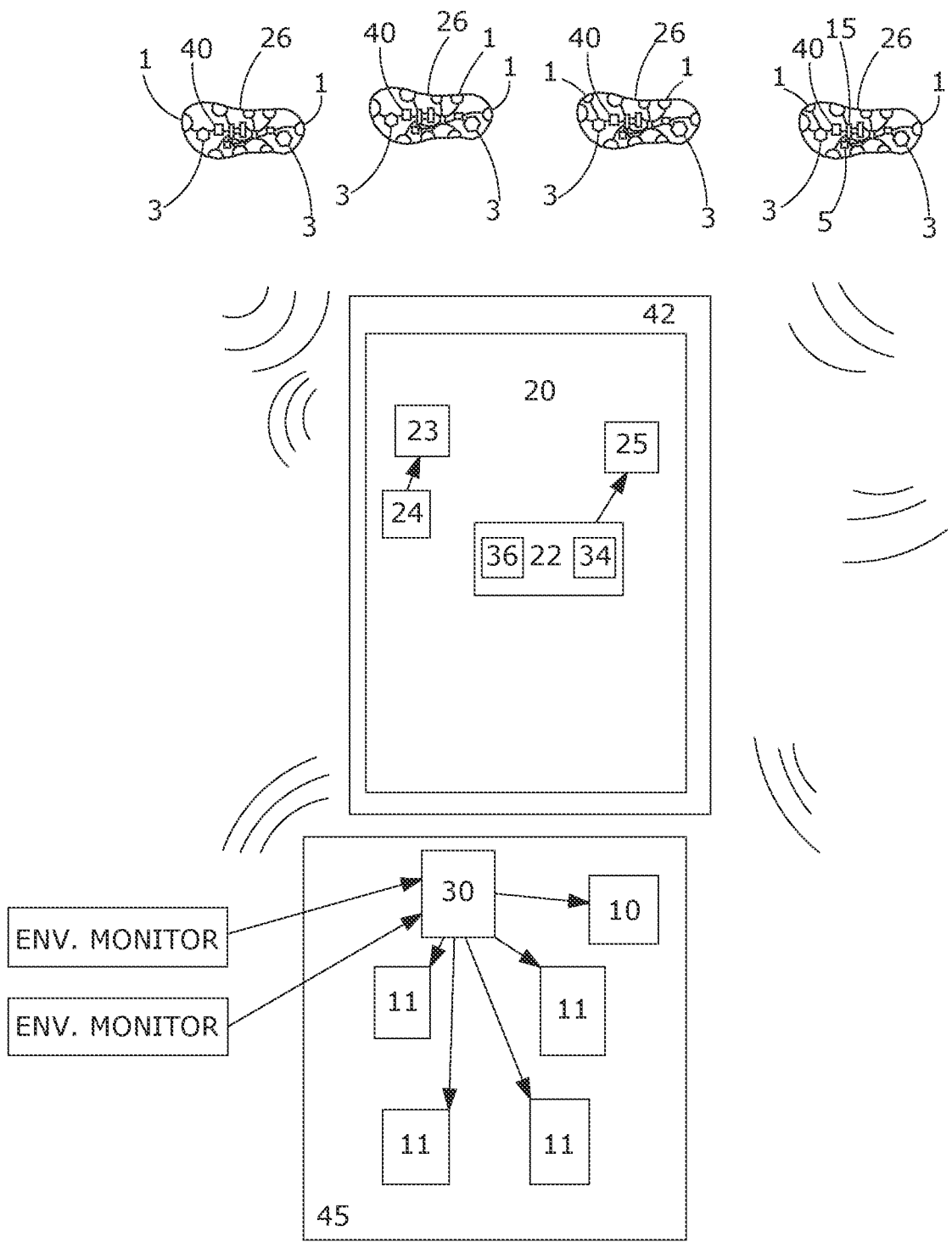

FIG. 11 shows another example of a healthcare provider using patients' registered response data to understand the patients' conditions better and alert the healthcare provider if one of the patients' condition starts to worsen. The patients are users in this example. The patients have previously given the healthcare provider's remote program (20) permission to access their registered response data. Each patient has an input device which is a proxy model (26), that includes multiple pain indicator units (1). The remote program also includes an app coordination module (23) that controls the sounds made by any alarms operatively connected to the input devices, and makes sure that any alarm lights connected to each input device make different sounds from any alarm lights connected to the other input devices.

The users use the pain indicator units (1) on the proxy models (26) to broadcast data, based on the intensity and location of the pain they feel. This data is transmitted over the internet to the centralized receiving module (30) which, in this embodiment, integrates each individual user's registered response data into an individual database (11) for that user, and into the centralized integrated database (10). The centralized receiving module (30) also integrates any environmental data that the centralized receiving module received, pertaining to the user's location, during the time that the user has expressed information, into the centralized integrated database (10). The healthcare provider's remote program (20), running on the healthcare provider's PC (42) accesses the individual database (11) for each of the users, and the healthcare provider can then use the app calculation module (22) of the healthcare provider's remote program (20) to perform calculations and graphing concerning the registered response data in the individual databases (11) for the users, and also calculations and graphing concerning the combined registered response data in those individual databases (11), For example, the app calculation module may be asked to graph all of the group's users' registered responses for the past 24 hours on one graph.

The healthcare provider, in this embodiment, can also command the calculation module to give the healthcare provider an alert when a quantity in one or more of the users' registered response data, or the results of the above analysis, reaches a certain level, such as when the pain level registered by one of the users reaches a certain degree.

Figure 12:
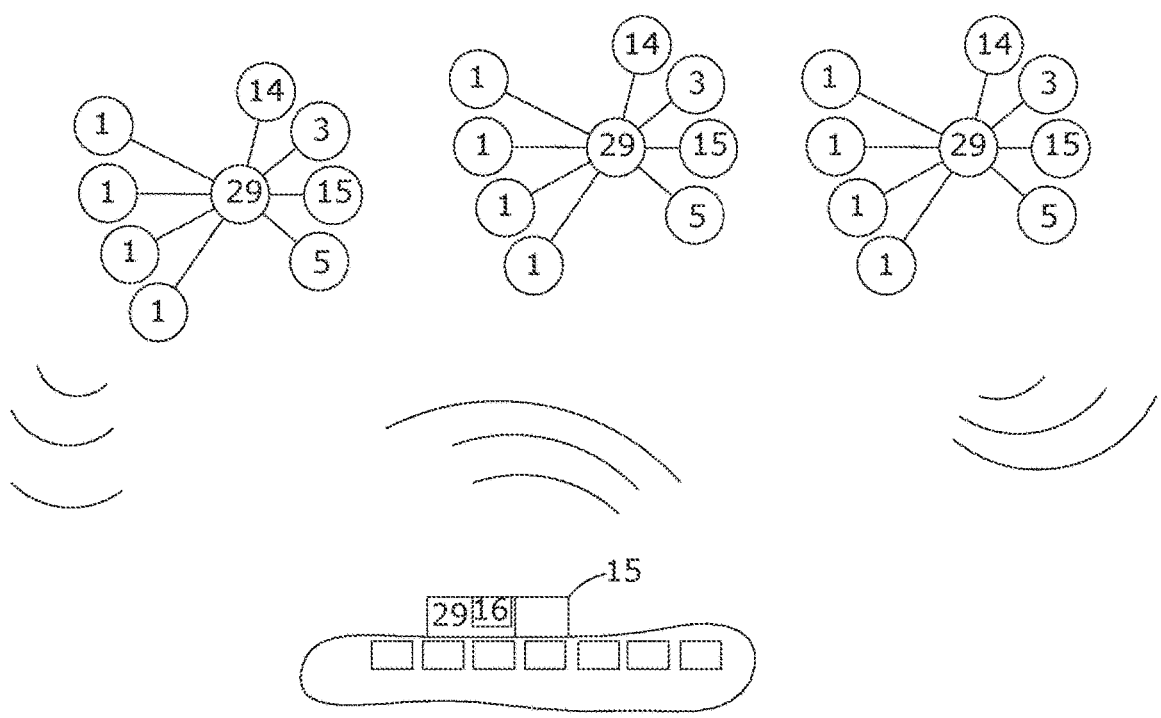
Figure 12:
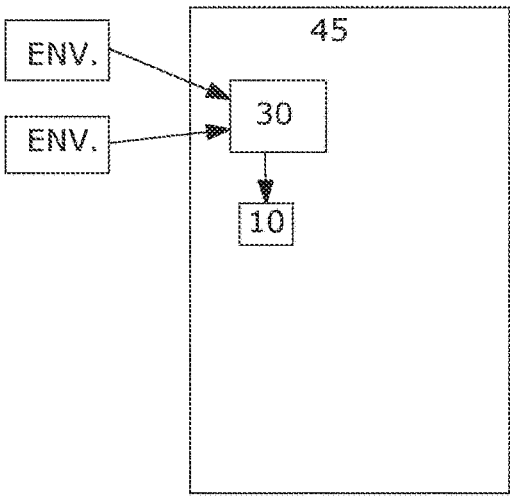

FIG. 12 shows a diagram of how a coordination module (16) can be used to quickly tell whether any users/patients, in a group of patients, are in distress, and how it is possible to prioritize the urgency of caring for the users/patients based on how much distress they are in. Each user in a group of users, has multiple pain indicator units (1) connected to a processor (29). There is one processor for each user. Each processor (29) is connected to a receiver (5), a transmitter (15), an alarm light (3), and an alarm (14). The users' healthcare provider has a coordination module (16) running on a computer, where the computer is operatively connected to a transmitter (15). The coordination module (16) uses the transmitter (15) to communicate with the receivers (5) that are connected to the processors (29), and tell them the sound that each of the alarms (3) should make when a patient uses the pain indicator unit connected to that alarm to register a response specifying pain of a certain location and intensity level. Likewise, the coordination module (16) uses the transmitter (15) to communicate with the receivers (5), and tell them which visual indication each of the alarms (3) should make when a patient uses the pain indicator unit connected to that alarm to register a response specifying pain of a certain location and intensity level.

The receivers (5) will transmit the information about which sound each alarm should make, and which visual indication each of the alarm lights should make, to the processors (29) connected to the pain indicator units. These processors (29) are also connected to the alarms (14) and alarm lights (3), and when one of the users activates a pain indicator unit (1), the processor (29) connected to that pain indicator unit will cause the alarm (14), alarm light (3), or both, connected to that processor (29), to make the visual indication or sound that the coordination module (16) has specified.

Those transmitters (15) that are connected to the processors (29) transmit the registered responses the users in the user group made. These registered responses are transmitted over the internet and reach the centralized receiving module (30) which saves each registered responses plus any available environmental, location, and individual data that pertains to the same time as that registered response into the centralized integrated database (10).

Figure 13:
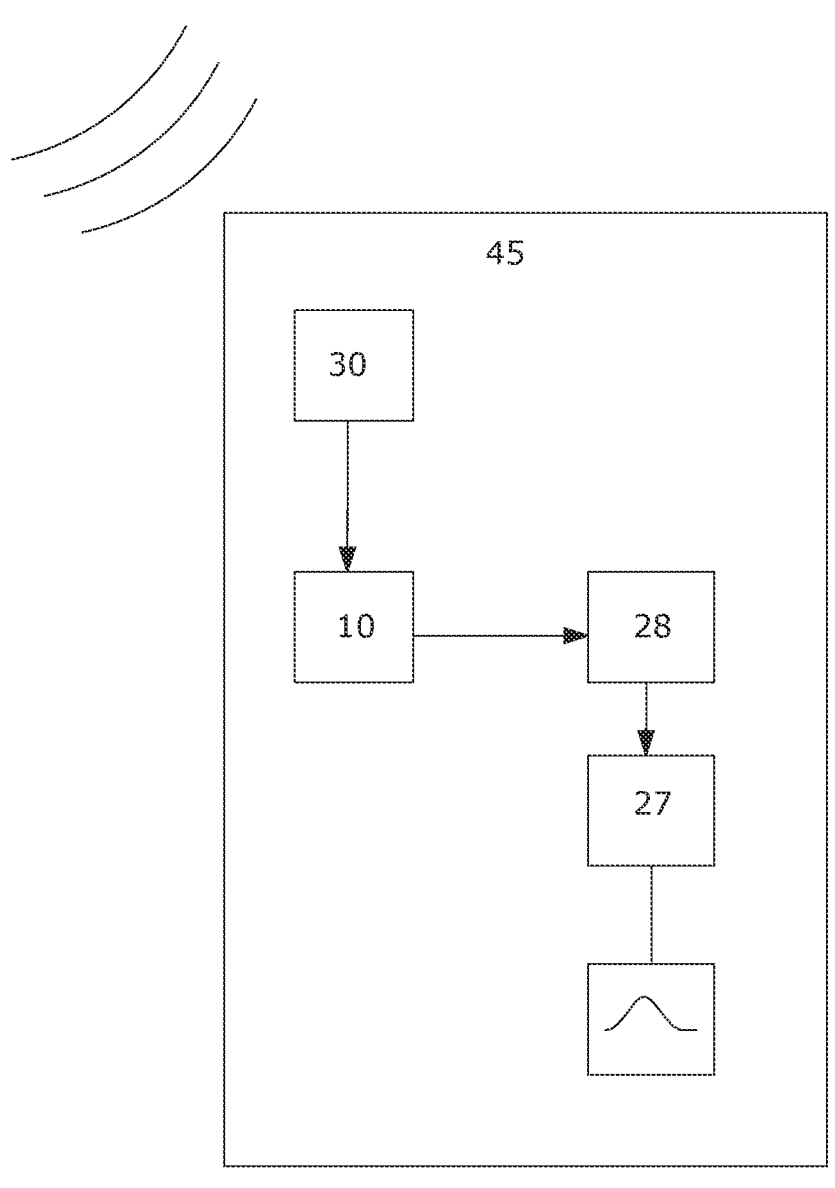

FIG. 13 shows a flow chart of one way that information about the pain patterns of a population of users can be assessed. The centralized receiving module (30) receives information about the users' responses, including, where available, the time, location, intensity, type, and duration of each response, and, where available, the user ID of the user who makes each response. In this case, each response also includes information about the medical conditions experienced by each user who sends that response, and personal information such as the age and ethnicity of the user who sends that response. The centralized receiving module (30) saves the responses in the centralized integrated database (10). The centralized calculation module (28) then performs statistical calculations on the responses. In this version of the invention, the centralized calculation module (10) then sends the statistical calculations' results to the integrated statistical display (27), which displays these results for researchers to use.

Figure 14A:
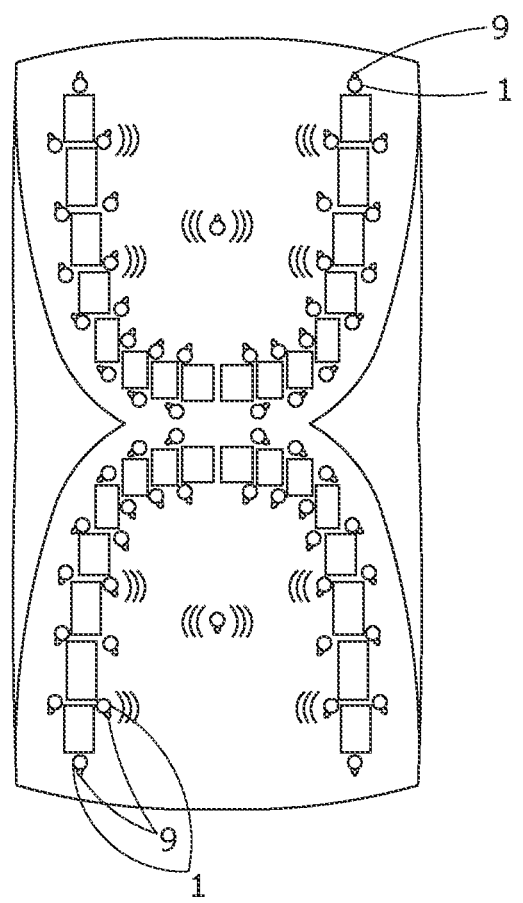

FIG. 14a shows a mouth model (8) with several position sensors (19) attached to pain indicator units (1). The position sensors that are broadcasting are indicated, showing that each position sensor can detect the other position sensors, and their locations relative to that position sensor (The "first position sensor").

Figure 14B:
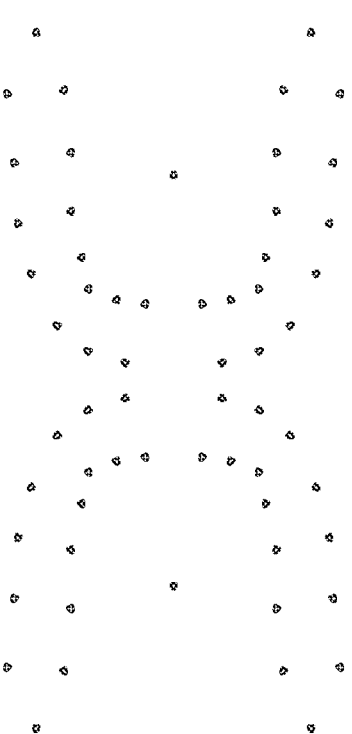

FIG. 14b shows one way in which a nearby processor might read the locations of the position sensors in the same mouth model relative to each other.

Figure 14C:
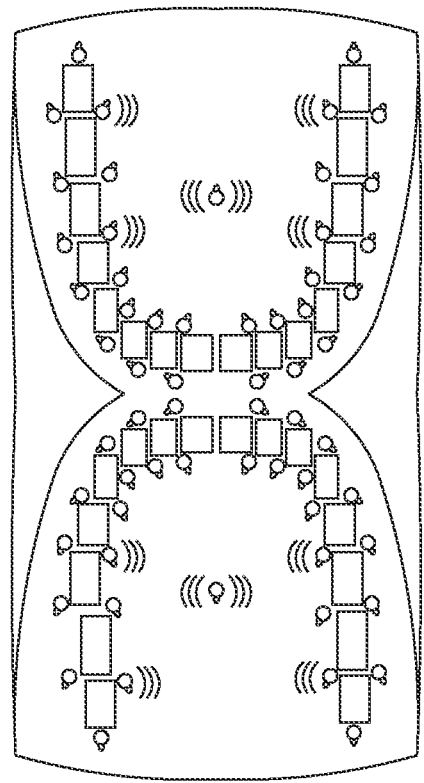

FIG. 14c shows the same mouth model (8) as FIG. 14a with two of the teeth moved. The pain indicator units and position sensors on those teeth are also moved. The position sensors continue to broadcast, to detect each other, and to broadcast their locations relative to each other, which means that each first position sensor will be able to detect the new location of every other position sensor relative to the first position sensor.

Figure 14D:
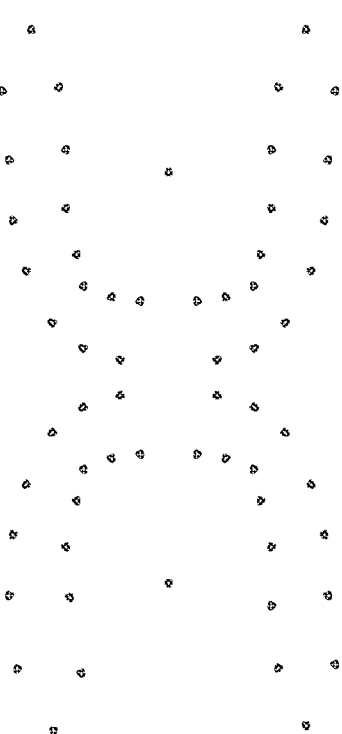

FIG. 14d shows how a nearby processor might read the position sensors' locations relative to each other in the mouth model, after the two teeth and the attached position sensors have been moved.

Figure 15:
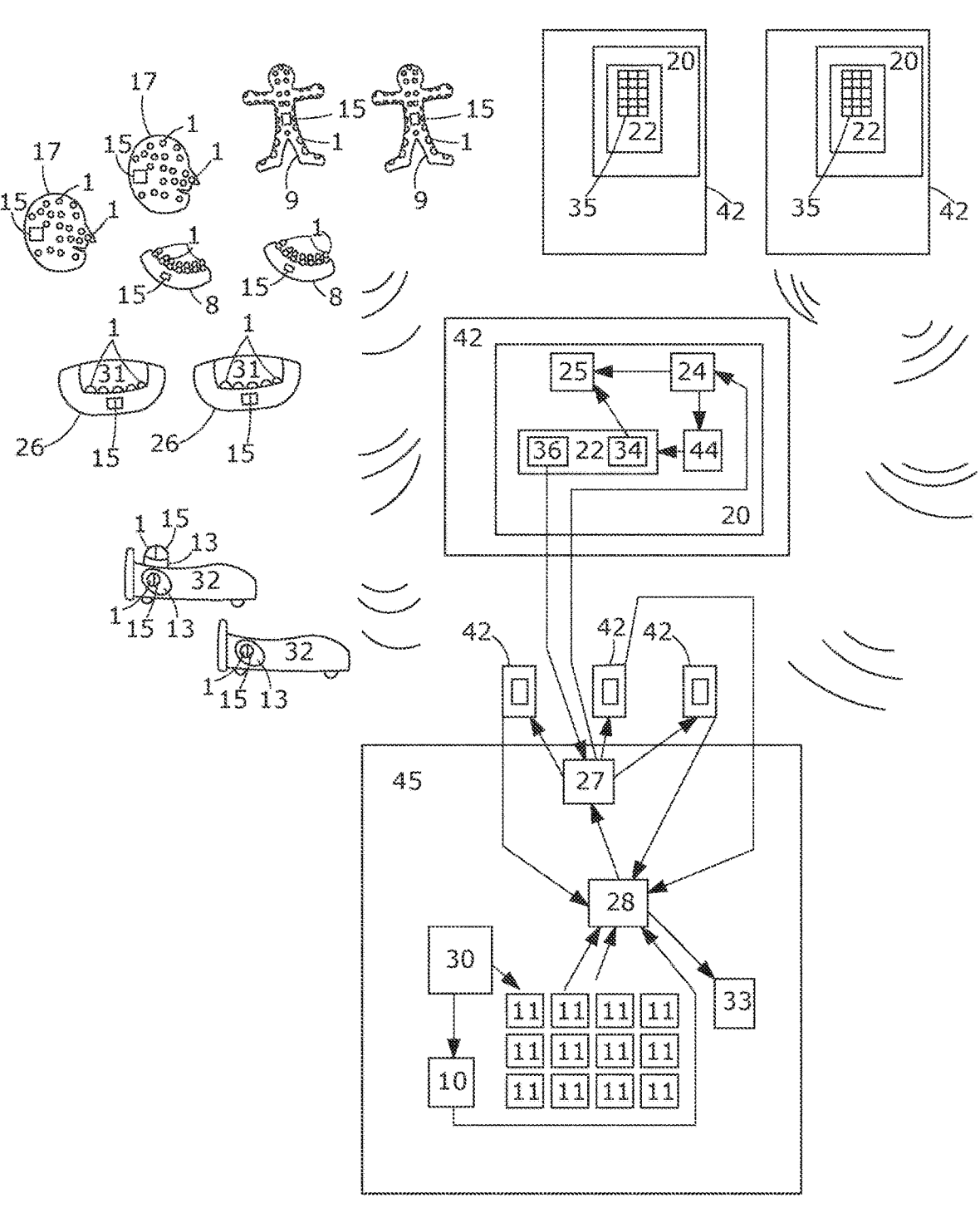

FIG. 15 shows a flow chart of how the pain patterns of a user group can be assessed. A first user group creates responses using pain indicator units (1) that are on proxy models (26), part models (17), mouth models, and human body models, and pain indicator units (1) attached to suction cups, that are attached to beds (pieces of furniture), that are pain indicator pieces (32). Some of the proxy models (26) have covers (31) on them. A second user group have remote programs (20) with pain indicator virtual units (35) running on their cellular phones (A type of PC (42)). All of the responses are sent using transmitters (15) to a centralized receiving module (30), which saves the responses in the centralized integrated database (10). Researchers can then use the centralized calculation module (28) to make calculations and create graphs using these responses as data, and hopefully gain insights. The second user group's responses also are received by the remote program (20) running on a PC (42) controlled by a healthcare practitioner, who is also a healthcare provider, whom the second user group has given permission to access their responses. The healthcare practitioner can additionally use the app calculation module (22) to make calculations and create graphs using the second user group's responses as data. The healthcare practitioner might be able to learn useful things about the pain the second user group suffered, and their health, from these calculations and graphs, and make useful recommendations to the second user group's members, based on these insights.

Figure 16:
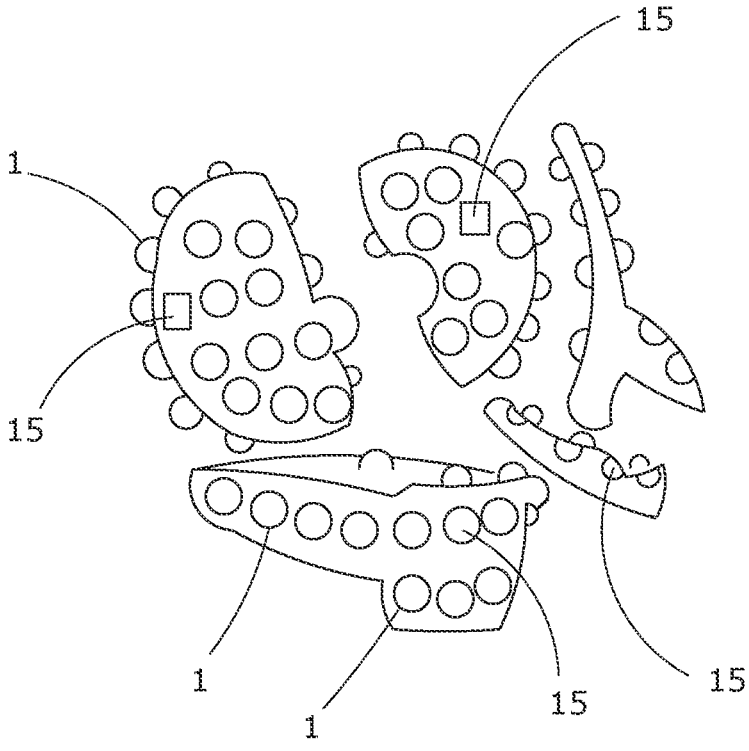

FIG. 16 shows an example of a part model (17) of a user's head, divided into several pieces that can interlock. Each of the pieces has at least one pain indicator button. A user can press one of the pain indicator buttons to show that he/she is experiencing pain in that part of his/her head.

Figure 17:
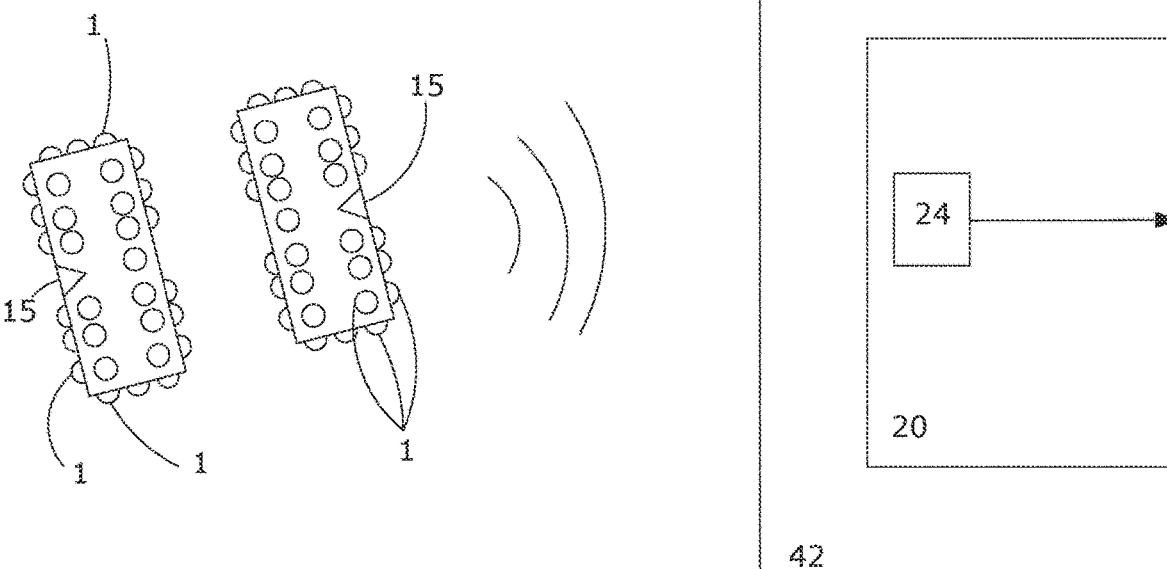

FIG. 17 shows two proxy models (26), each of which represents half of the user's head. The two proxy models

(26) each include multiple pain indicator units (1) and a transmitter, which is operatively connected to the pain indicator units. The transmitters wirelessly broadcast responses that users make, using the pain indicator units. The nearby app receiving module (24), which is part of a remote program (20), running on a PC (42), receives the wireless responses.

Figure 18:
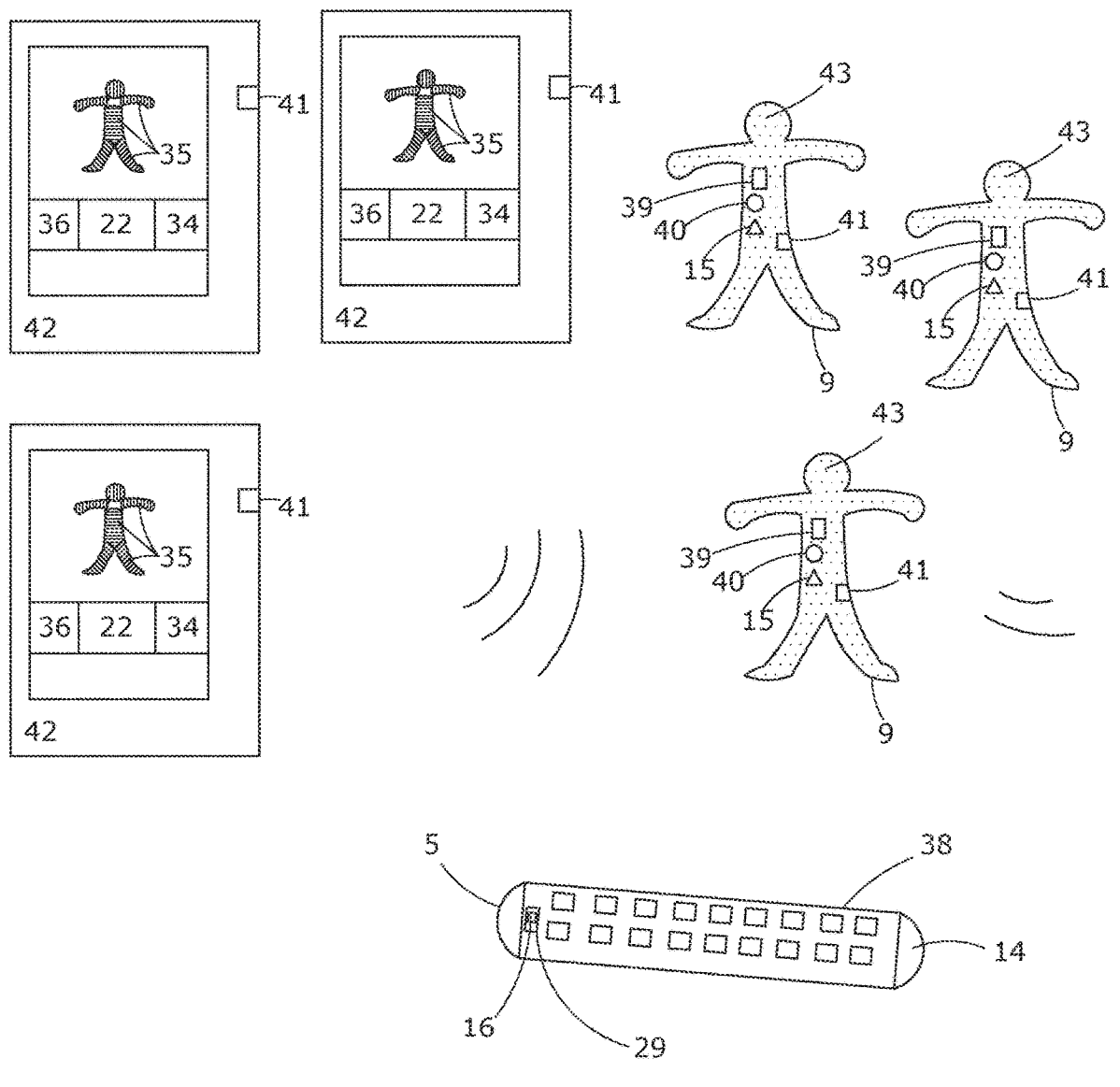

FIG. 18 shows an example of a healthcare provider using the invention to keep track of the locations and intensity of the pain being experienced by users in multiple subgroups in a user group. Some of the subgroups of users, comprising users who are outpatients, each have a remote program (20), on their cellular phones (A type of PC (42)). The remote programs each have an ID input function, so that the user using each remote program can identify themselves by their user ID before they start inputting responses into the pain indicator virtual units of the remote program, and then, if desired, "log off" and allow another user to use the same remote program to identify themselves by their user ID and input responses, if desired. The remote programs each include pain indicator virtual units (35) representing different areas of the user's body. The remote programs (20) also each include an app input module (36), which a user using one of the remote programs can use to tell the app calculation module (20) to make calculations and view graphs related to that user's pain, in different body parts, and variations in that user's pain over time. Each cellular phone also has a data export port (41) in the form of that cellular phone's USB port. Some of the user subgroups, comprising some users who are inpatients, and some users who are outpatients, have human body models (9), with pain indicator skins (43). Each human body model also has an ID input port (40), where a user can input the user's User ID, such as a fingerprint. The human body models (9) each also have a data export port (41), and a time division indicator (39), and a transmitter (15). The transmitter (15) in each of the human body models (9) broadcasts the degrees and locations of the pain the user of that human body model registers, using that human body model, along with the time division indication that the user of that human body model used the time division indicator to select. A healthcare provider has a display device (38) shaped like a rod, with a receiver (5), and with lights that light up in different colors depending on the average pain level reported by users in the subgroups. The display device (38) may be located in an area where the healthcare provider may easily take action if the average pain level reported by users in a subgroup gets too high, such as the reception desk of a hospital department where some of the users are patients. The display device (38) also has a processor programmed with a coordination module that causes the display device to make a different noise when each of the users using a human body model indicates that this user is feeling a high pain degree on the pain scale being used. The noise the display device makes changes depending on which user indicates that the user is feeling a high pain degree.

DETAILED DESCRIPTION OF THE DRAWINGS

Figure 1:
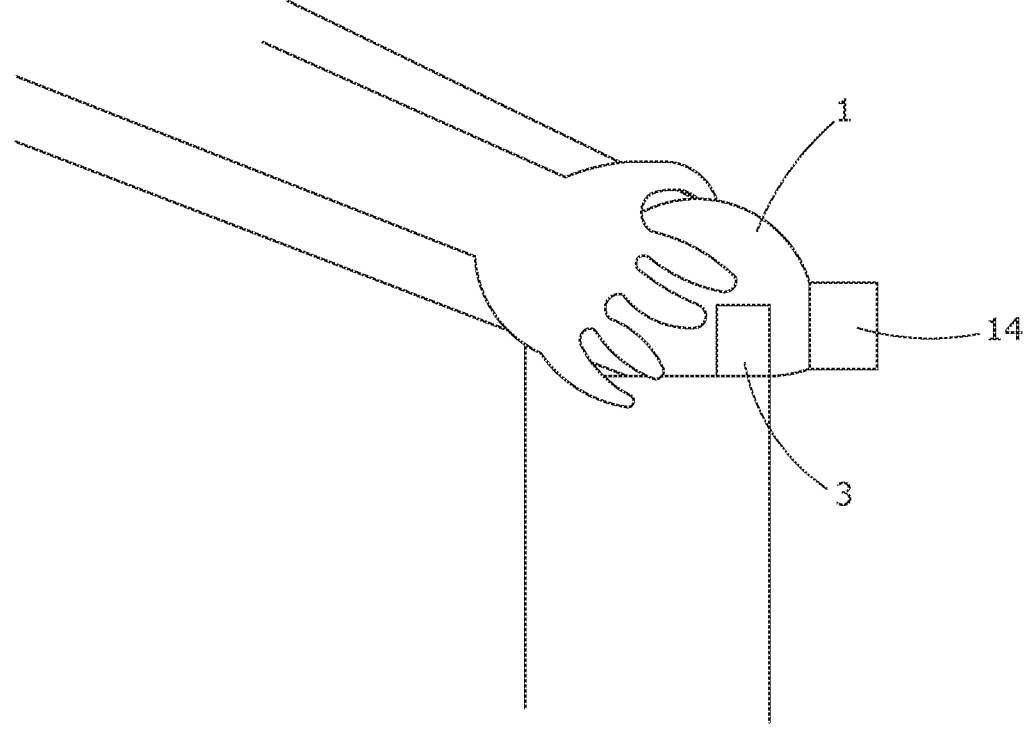
FIG. 1 shows a person's hand using one of the first versions of the invention.

FIG. 1 shows a user's hand using one of the invention's first embodiments. The user is sitting in a dental chair and grasping the instrument with the pain indicator unit (1). When the user feels pain, the user presses the pain indicator unit (1) which is a button, and an alarm (14) sounds and an alarm light (3) flashes.

Figure 2:
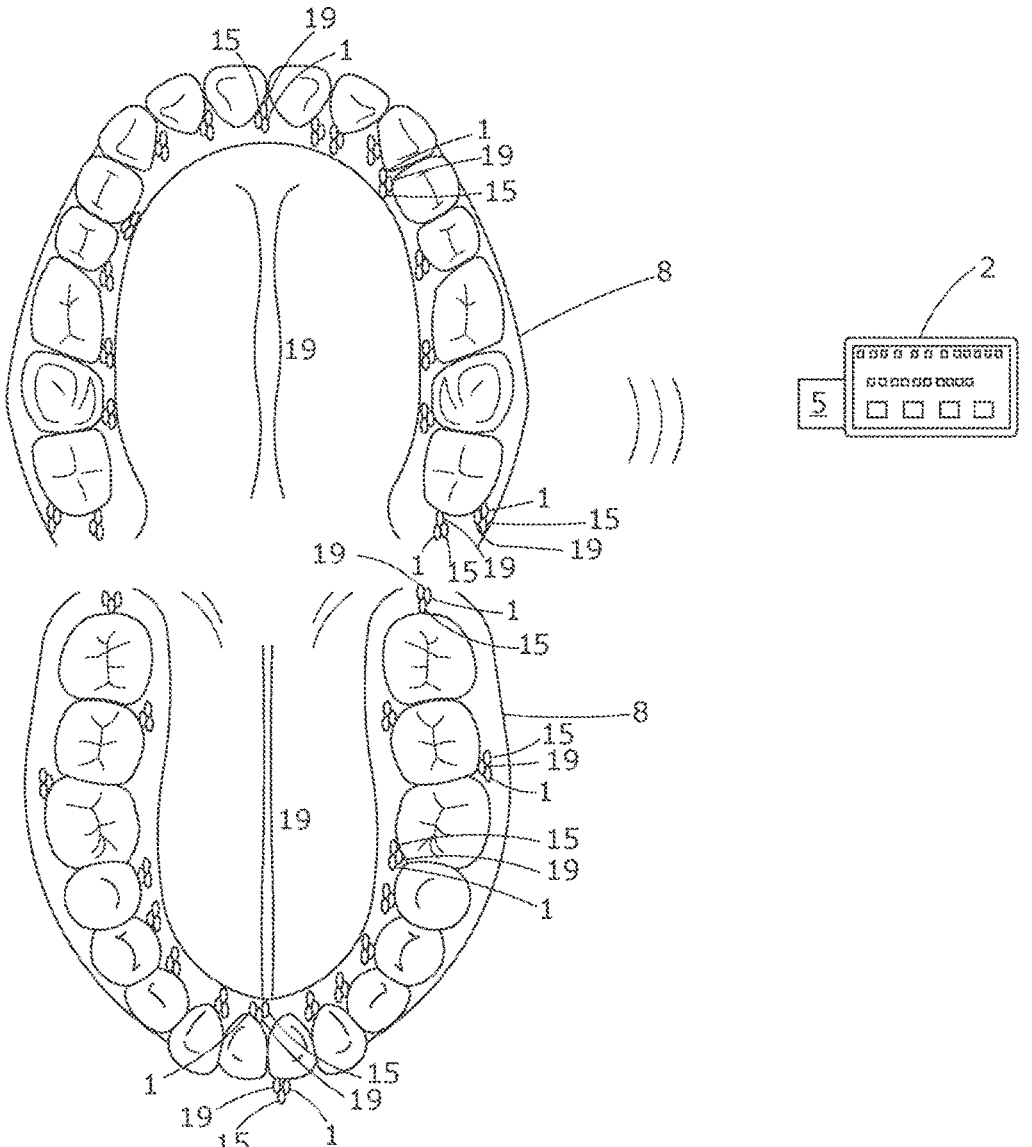
FIG. 2 shows a person's hand using a mouth model (8) customized to look like a model of that person's mouth.

FIG. 2 shows a person's hand using a mouth model (8), customized to look like that person's mouth. There are several position sensors (19) in the mouth model, and each position sensor is attached to a pain indicator unit (1). The position sensors (19) and pain indicator unit (1) are each in a group, and each group includes one position sensor, one pain indicator unit, and one transmitter (15). The transmitters transmit to a receiver (5) which is connected to a display section (2), which shows which of the pain indicator units (1) is being pressed, and shows other information below. When one of the pain indicator units (1) is pressed, one of the small squares towards the top of the display section lights up.

Figure 3:
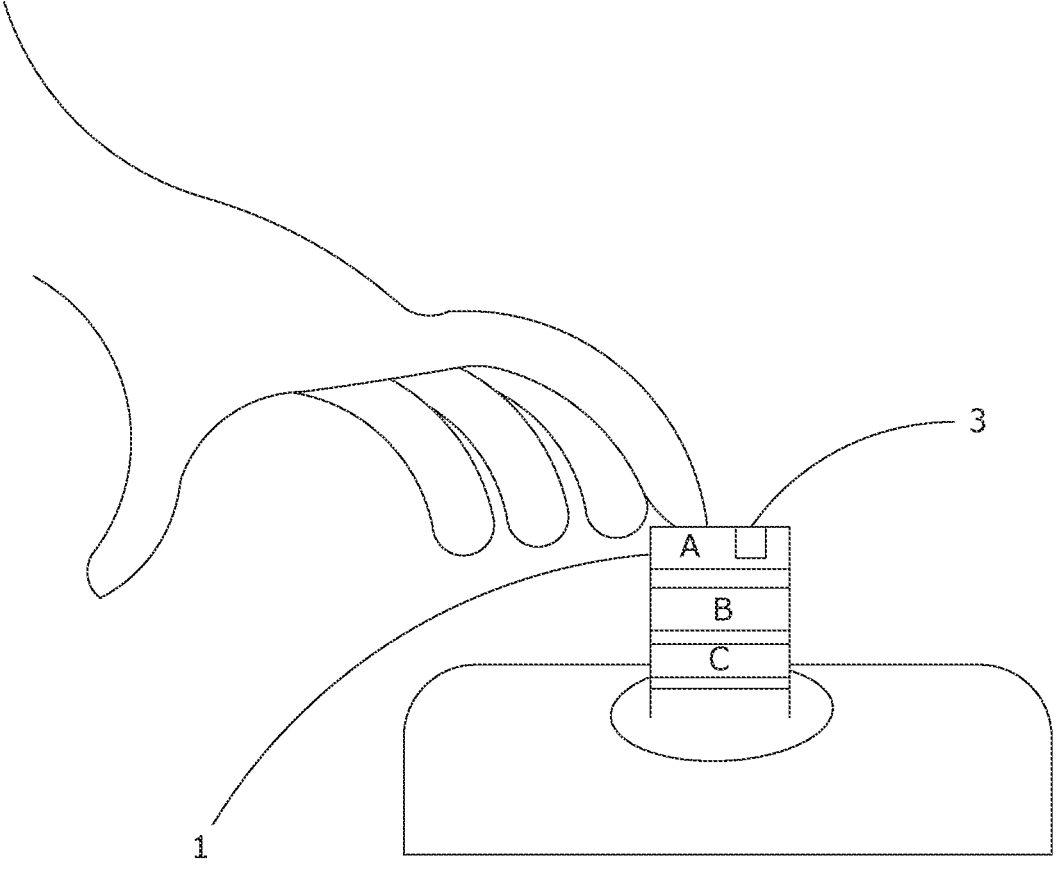
FIG. 3 shows a user's hand using a pain indicator unit (1) that is a button, with grooves along its side, and that is in a pad.

FIG. 3 shows a user's hand using a pain indicator unit (1) that is a button, in a pad, and with grooves along its side. The grooves, indicating A, B, and C, can be seen. This pain indicator unit (1) is designed to be used with a pain scale where pain level A is the highest, then pain level B, then pain level C. The user can indicate how much pain the user is feeling, by pressing down the pain indicator unit to the level which indicates the pain level the user is feeling. The pain indicator unit goes down further into the pad, depending on how hard it is being pressed, so if the user presses a little, the pain indicator unit (1) will be pressed down to the level where all of the pain indicator unit below the groove for C is inside the pad. This would show that the user is feeling pain level C. If the user presses harder, the pain indicator unit will be pressed down to the level where all of the pain indicator unit below the groove for B is inside the pad, which will indicate that the user is feeling a higher level of pain, etc. The pain indicator unit also contains an alarm light (3) which can flash when the pain indicator unit is pressed.

Figure 4:
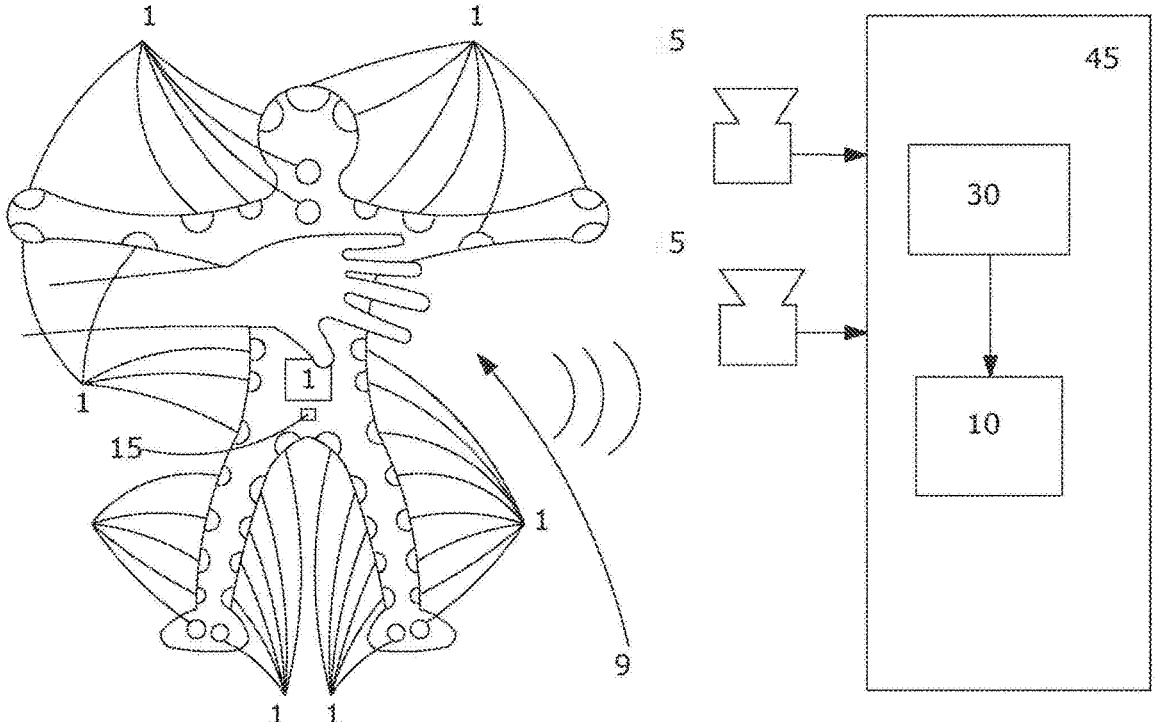
FIG. 4 shows a user's hand using a human body model (9) and pressing some of the pain indicator buttons (1) on that model to show the degree and length of the pain the user experiences. These pain indicator buttons connect to a transmitter (15) in the human body model. The transmitter in the human body model sends transmissions about the degree, and length of pain the user experienced out to receivers (5) elsewhere. The receivers (5) then transmit this information, using the internet, to the centralized receiving module (30) elsewhere, which integrates this information into the centralized integrated database (10). The centralized receiving module (30) is part of the centralized program (45).

FIG. 4 shows a user's hand using a human body model (9) and pressing some of the pain indicator units (1) which are buttons on that human body model to show the degree and length of the pain the user experiences. These pain indicator units that are buttons connect to a transmitter (15) in the human body model. The transmitter in the human body model sends transmissions about the degree, and length of pain the user experienced out to receivers (5) elsewhere. Here two receivers are shown, but it is understood that more or fewer receivers may receive and transmit this information. The receivers (5) transmit this information, using the internet, to the centralized receiving module (30) elsewhere, which, in this embodiment, integrates this information into the centralized integrated database (10). The centralized receiving module (30) is part of the centralized program (45).

Figure 5:
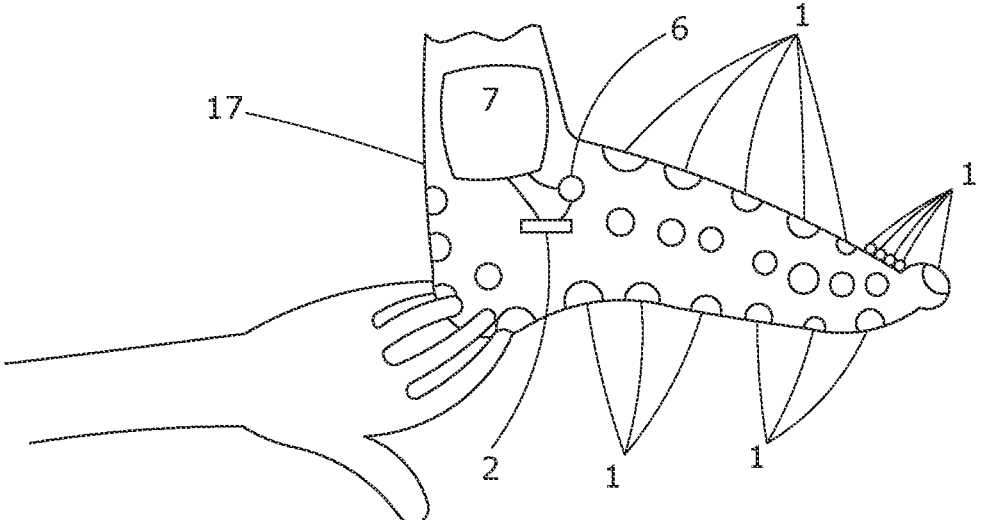
FIG. 5 shows a user's hand using a part model (17) of a human's foot. Components inside the part model are also shown in FIG. 5.

FIG. 5 shows a user's hand using a part model (17), in this case a part model (17) of a human foot. The part model (17) includes multiple pain indicator units (1). Components of the invention inside the part model are also shown in FIG. 5. The part model (17) also contains a battery (21) which is connected to a battery charger (6). The battery charger is connected to a solar cell (7). The solar cell (7) sends power to the battery charger (6), which sends it to the battery (21). The solar cell also can send power directly to the battery (21). The battery powers the pain indicator units (1).

Figure 6:
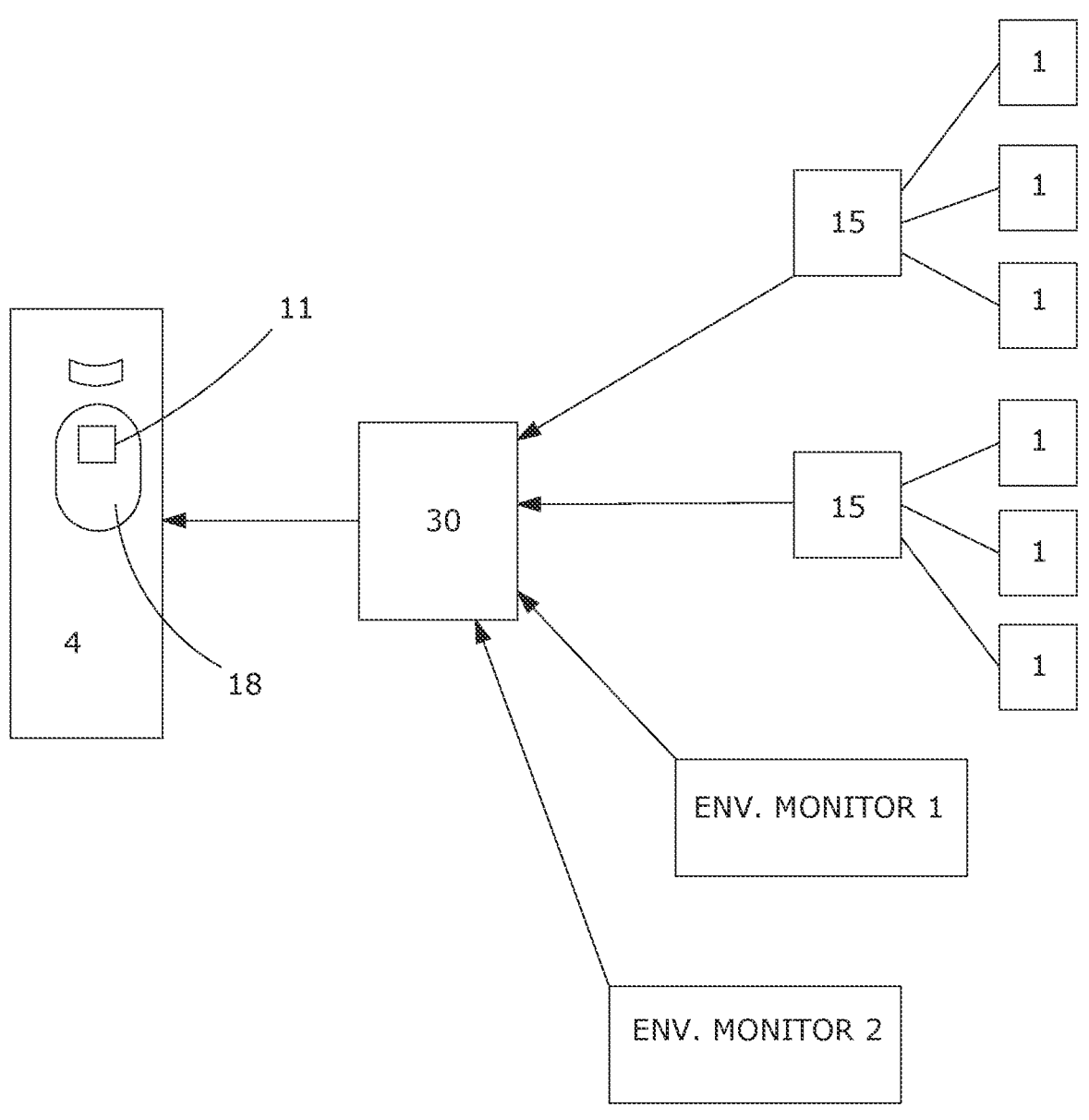
FIG. 6 shows a memory (18) stored on a server (4), where the memory (18) contains an individual database (11) and is connected to, and accessible through, the internet. The centralized receiving module (30) receives registered responses from pain indicator units (1) connected to transmitters (15) in multiple input devices, and stores these registered responses in the individual database (11). The centralized receiving module (30), in this embodiment, also receives environmental information from environmental monitors, and stores this environmental information in the individual database.

FIG. 6 shows an individual database (11) being part of a memory (18) stored on a server (4), which is connected to, and accessible through, the internet. Information about an individual user's responses is integrated into, and saved in, the individual database (11) for that user. The centralized receiving module (30) receives registered responses from pain indicator units (1) operatively connected to transmitters (15) in multiple input devices, and stores the responses referring to a certain individual user in the individual database (11) for that individual user. Two input devices are pictured, but it is understood that the centralized receiving module (30) can receive input from more than two input devices. The centralized receiving module (30), in this embodiment, also receives environmental information from environmental monitors, relating to each registered response. Two environmental monitors are indicated, but it is understood that the centralized receiving module (30) may receive environmental information from more environmental monitors. The centralized receiving module (30) stores the environmental information relating to each registered response in the individual database (11), and associates the environmental information relating to each registered response with that response. The centralized program may have other components that are not shown because they are not relevant to the relationships shown in this drawing.

Figure 7:
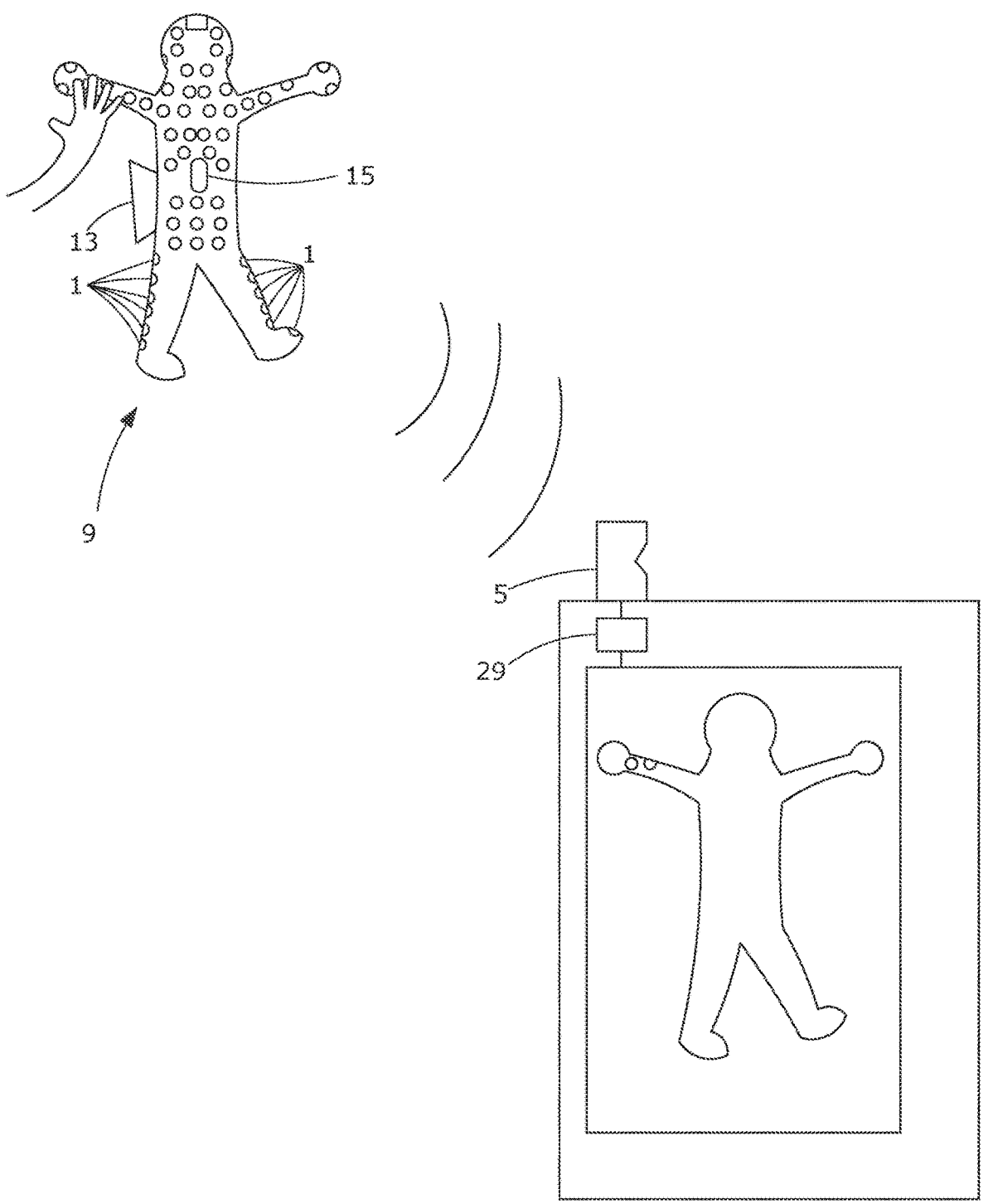
FIG. 7 shows a human body model (9) connected to a human body display (12). The human body model (9) includes multiple pain indicator units (1).

FIG. 7 shows a human body model (9) with pain indicator units (1) on it. The human body model (9) also has a suction cup (13) attached, so that the human body model (9) will stay in one place. All of the pain indicator units (1) are connected to a transmitter (15). A user is pressing two of the pain indicator units (1) that are buttons and these are transmitting information to the transmitter (15). A receiver (5) is receiving the signals from the transmitter (15). The receiver is transmitting this information to a processor (29) which controls a human body display (12). Parts of the human body display are glowing, in a color that matches the strength of the user's pressing the pain indicator units, displaying that the user is experiencing pain.

Figure 8:
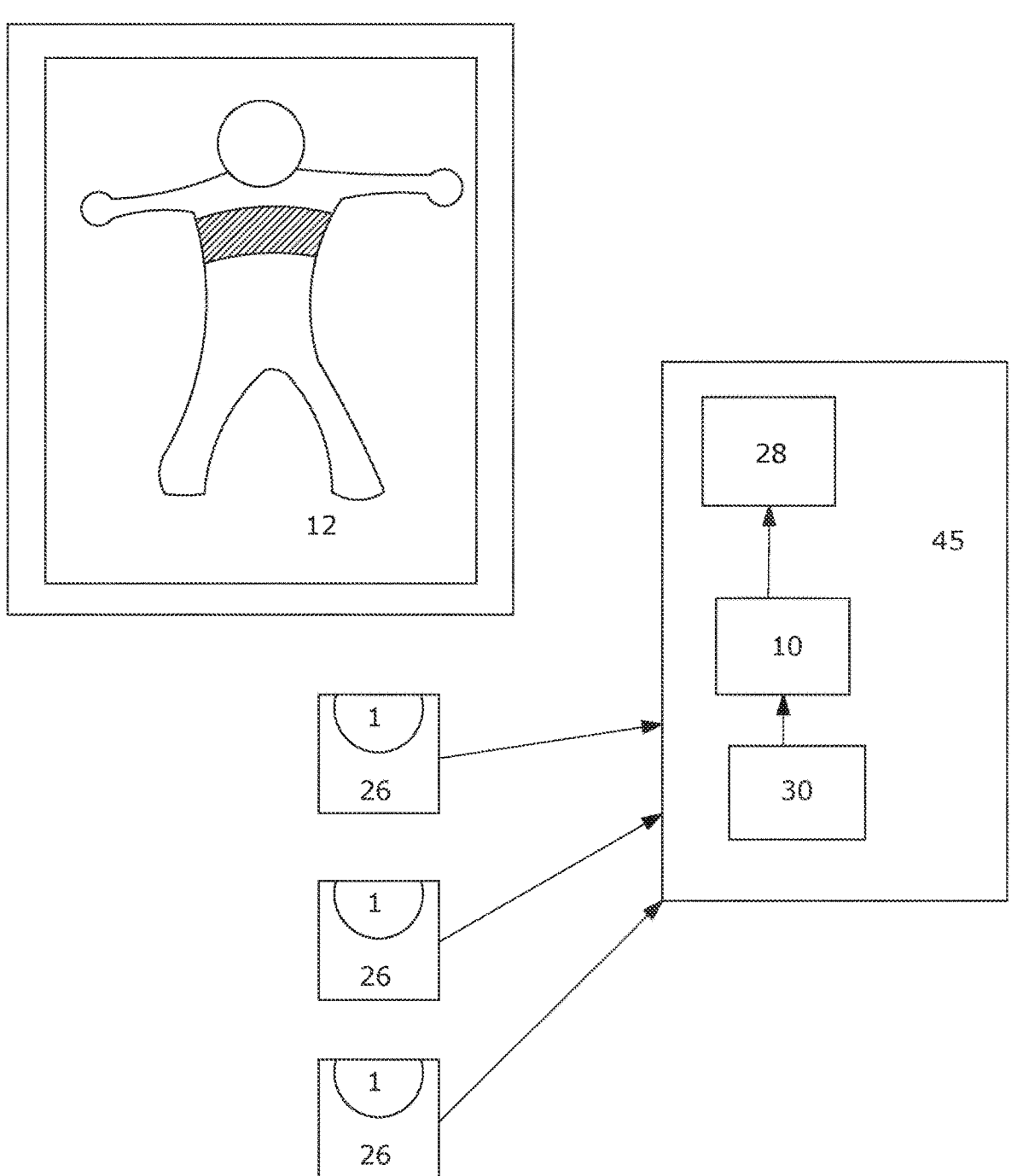
FIG. 8 shows how in one embodiment, the centralized integrated database (10), centralized program (45) that included a centralized calculation module (28), and a human body display (12) work together. The centralized calculation module (28) performs calculations on the data in the centralized integrated database (10) and sends these calculations' results to the human body display (12), which creates a visual display explaining these results. For example, in this embodiment, the human body display displays the average pain level in the chest cavity users have registered 3 days after having a broken rib set. The chest in the human body display (12) glowing in a certain color shows this average pain level.

FIG. 8 shows how in one embodiment, the centralized integrated database (10), centralized program (45) that included a centralized calculation module (28), and a human body display (12) work together. For example, in this embodiment, the human body display displays the average pain level in the chest users have registered 3 days after having a broken rib set. The centralized receiving module (30) is continuing to receive registered responses from users and place them in the centralized integrated database (10). The users are registering their responses on pain indicator units (1) on proxy models (26) that represent the chest cavity. Three such proxy models (26) are shown, but it is understood that the centralized receiving module can receive registered responses from more than three proxy models with pain indicator units attached.

The centralized calculation module (28) finds registered responses in the centralized integrated database (10) that represent the pain users felt in their chest cavities three days after experiencing a broken rib. The centralized calculation module (28) performs calculations on these registered responses and sends the calculations' results to the human body display (12), which makes a visual display explaining these results. The chest in the human body display (12) glowing in a certain color shows this average pain level. The centralized program (45) may have other components that are not shown because they are not relevant to the relationships shown in this drawing.

Figure 9:
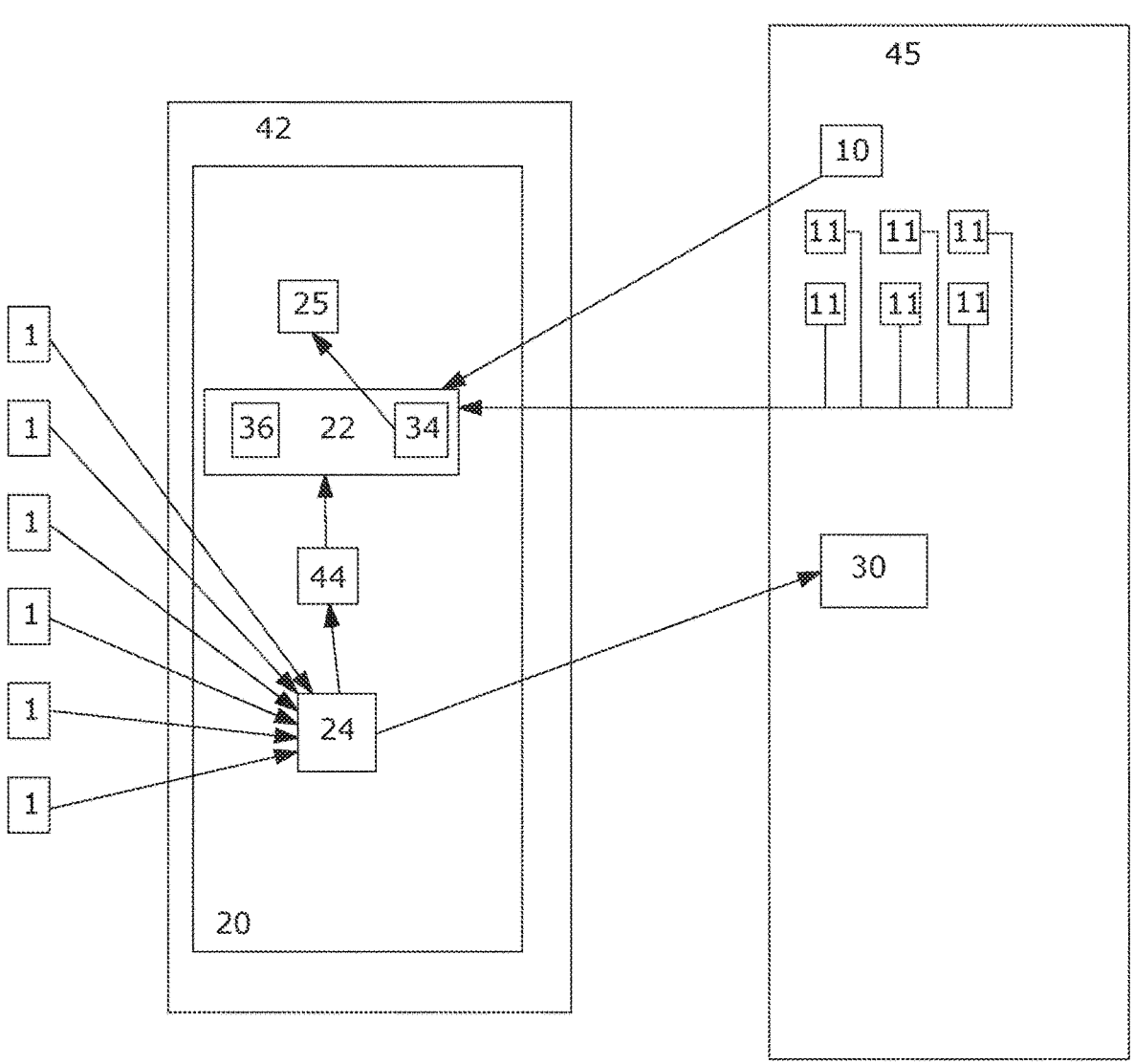
FIG. 9 shows a flow chart of data flows in an embodiment of the remote program (20) running on a PC (42). The first user's app receiving module (24) receives responses from the pain indicator units in the first user's input devices, and the app receiving module stores these responses in the app database (44). The app receiving module (24) also rebroadcasts these responses using the PC's wireless capability. The centralized receiving module (30) receives the responses over the internet and stored them in the first user's individual database (11). The first user has access to the individual database (11) through the remote program (20) in this embodiment. The first user can use the app calculation module (22) to do calculations and graphs using the data points in the individual database (11) for the first user, and the first user can learn whether there are any relationships between the first user's pain pattern and other events. For example, maybe the user experiences a statistically significantly more intense, and higher-duration, amount of pain in his/her lower abdomen when the AQI is above 100. The first user might not have known about this before. Or, maybe the amount of pain the first user experiences in his/her upper chest, each day, has been statistically significantly increasing over the past six months. The app display module (25), using the first user's PC (42), will display the results of the calculations and/or graphing to the user.

FIG. 9 shows a flow chart of data flows in an embodiment of the remote program (20) running on a user's PC (42), The app receiving module (24) receives responses indirectly from pain indicator units (1) in a group of a first user's input devices and the app receiving module (24) stores these responses in the app database (44). Six such pain indicator units (1) are shown, but it is understood that the app receiving module (24) can receive input from more than six pain indicator units, and from pain indicator units in more than six of a user's input devices. The input devices in this embodiment can each include more than one pain indicator unit. The app receiving module (24) also re-broadcasts these responses. The centralized receiving module (30), which is part of the centralized program (45) receives the responses and stores the responses in the individual database (11) for the first user. In this version of the invention, the first user with the PC has access through the remote program (20) to that user's individual database (11), anonymized information from the centralized integrated database (10) and, to the information in several second users' individual databases (11), where those second users had previously given the first user access to the information in their individual databases (11). The centralized program (45) may have other components that are not shown because they are not relevant to the relationships shown in this drawing.

The first user can use the app input module (36) to tell the app calculation module (22) to do calculations and create graphs using the data points in the first user's individual database (11), and the second users' individual databases, and the first user can learn whether there are any relationships the user should know about, such as general trends in the amount of pain that the first user feels in certain areas of the first user's body, or relationships between an increase or decrease in the pain degree the first user feels in a certain area of the first user's body, and other phenomena. For example, maybe the first user experiences a statistically significantly more intense, and higher-duration, amount of pain in his/her lower abdomen when the AQI is above 100. The user might not have known about this before. Or, maybe the amount of pain the first user experiences in his/her upper chest, each day, has been statistically significantly increasing over the past six months. The app transmission module will send the results of the calculations and/or graphs to the app display module (25). The app display module (25), using the user's PC, displays the calculations' results and/or graphing to the user. The remote program (20) and centralized program (45) may have other components that are not shown because they are not relevant to the relationships shown in this drawing.

The app display module (25) displays the calculations' results and/or graphing.

Figure 10:
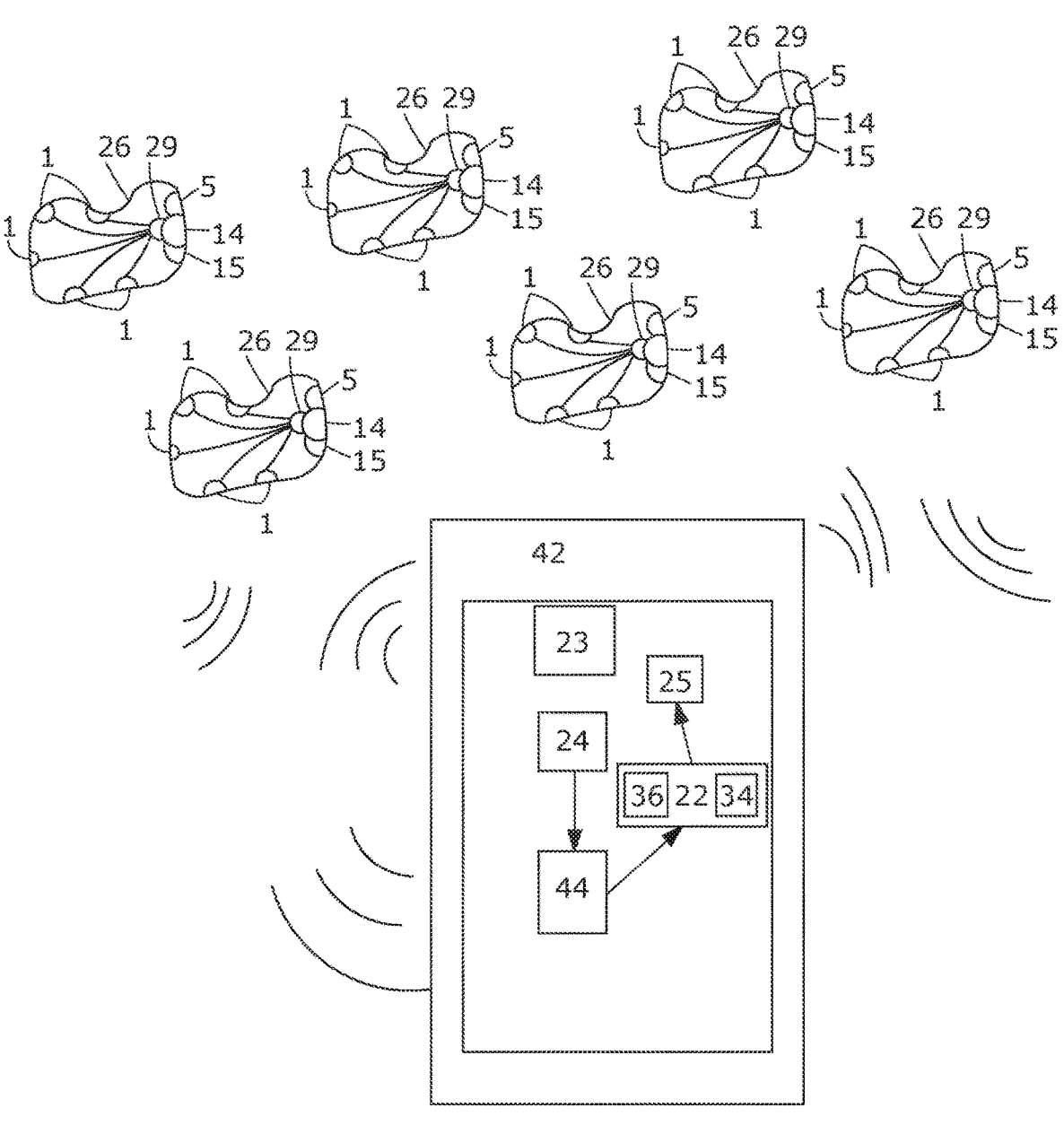
FIG. 10 shows a diagram of one example of how in one embodiment of the invention, response data from input devices being used by several users who are also patients, flows into the patients' healthcare provider's remote program (20), running on the healthcare provider's PC (42), and some ways that the response data can then be used. All of the input devices are part of a group of input devices. The input devices are proxy models (26), each of which includes multiple pain indicator units (1). The patients in this example have previously given the healthcare provider's remote program (20) permission to access the patients' response data. The remote program also includes an app coordination module (23) that controls the sounds the alarms operatively connected to the input devices make, and ensures that any alarms connected to each input device in the group make different sounds from the alarms connected to any other input devices in the group, and that any alarm lights connected to each input device in the group flash in a different color(s) and/or light pattern(s) from any alarm lights connected to the other input devices in the group. The healthcare provider's app receiving module (24) receives the patients' registered response data as the users make responses. The receiving module rebroadcasts the response data, and places copies of the response data in an app database (44). The healthcare provider can use the app calculation module (22) of the healthcare provider's remote program (20) to perform calculations and graphing of the registered response data in the app database (44), and the healthcare provider's app display module (24) then displays the results of this analysis on the healthcare provider's PC (42).

FIG. 10 shows a diagram of one example of how response data from several users, who are also patients, flows into the patients' healthcare provider's remote program (20), running on the healthcare provider's PC (42) and one way that the response data is then used in one embodiment of the invention. The patients have previously given the healthcare provider's remote program permission to access their response data. The patients each have access to an input device which is a proxy model (26), including multiple pain indicator units (1) and an alarm (14), a transmitter (15), and a receiver (5) and a processor (29). The healthcare provider's remote program also includes an app coordination module (23) that controls the sounds the alarms operatively connected to the input devices the patients are using make, and the app coordination module (23) makes sure that A. Any alarms connected to each input device a patient is using makes different sounds from the alarms connected to any other input devices the patients are using, and B. Any alarm lights connected to each input device the patients are using flash in different colors and/or light patterns from any alarm lights connected to the other input devices the patients are using. The app coordination module (23) sends broadcasts that the receivers (5) in the proxy models (26) receive, and these receivers then send these communications to the processors (29) in the proxy models (26). The processors in the proxy models cause the transmitters (15) in the proxy models to broadcast communications specifying, among other things, the sounds each alarm in the proxy model is capable of making. The app coordination module (23)

receives these communications. Each proxy model of the particular type displayed in FIG. 10 was built with a standardized alarm capable of making certain sounds. The processor in each proxy model will be programmed with a list of these sounds and will cause the transmitter in that proxy model to broadcast the list. The app coordination module (23) will then pick which of these sounds each of the alarms should make when a user presses one of the pain indicator buttons on the proxy model (26) that contains this alarm, so that no two of the alarms make the same sound. The app coordination module (23) will broadcast the selection of the sound each alarm should make, and the receivers in the proxy models will receive these broadcasts, Each receiver in a proxy model will send the selection of the sound that the alarm in that proxy model should make to the processor in that proxy model. Then the processor in each proxy model will cause the alarm in that proxy model to make the selected sound when a user presses one of the pain indicator units in that proxy model.

The app receiving module (24) receives the patients'/users' registered response data the transmitters in the proxy models broadcast. The app receiving module (24) places the response data from the users in an app database (44), and also rebroadcasts the response data. The healthcare provider can input, into the app calculation module (22), calculations on the users' responses in the app database (44) that the healthcare provider wants to be performed. This includes calculations on subsets of the responses in the app database (44). The healthcare provider can also input, into the app calculation module (22), requests to graph the responses or subsets of the responses in the app database (44), The healthcare provider can also command the app calculation module to use the PC to produce an alert when some of the data being received, or some of the calculations' results, or one of the quantities being graphed, reaches a certain threshold. For example, the healthcare provider can command the app calculation module to use the PC to produce an alert when the mean pain level the patients are registering reaches a certain threshold. The remote program (20) and the centralized program may have other components that are not shown because they are not relevant to the relationships shown in this drawing.

The app calculation module will perform the calculations and/or create the desired graphs, and transmit the calculations' results, and the graphs, to the app display module (25), which will use the PC's display capabilities to display the graphs and/or calculations' results. The app calculation module will also produce an alert when the conditions the healthcare provider specified, for producing an alert, are met.

FIG. 11 shows another example of a healthcare provider using patients' registered response data to understand the patients' conditions better and alert the healthcare provider if one of the patients' health conditions starts to worsen. The patients are users in this example. The patients in a group of patients have previously given the healthcare provider's remote program (20) permission to access their registered response data. Each patient in the group has an input device which is a proxy model (26), that includes multiple pain indicator units (1), an alarm light (3), an ID input port (40), a transmitter (15) and a receiver (5). Four such proxy models (26) are shown, but it is understood that the group of patients can contain far more than four patients, each patient with a proxy model. The healthcare provider's remote program (20) also includes an app coordination module (23) that controls the sounds made by any alarms operatively connected to the input devices the patients are using, and makes sure that any alarm lights connected to each input device one of the patients is using make different-appearing light, such as light in different colors or different patterns, from any alarm lights connected to the other input devices the patients are using.

The users in the group use the pain indicator units (I) on the proxy models (26) to register responses, and the transmitters (15) in the proxy models (26) broadcast data, based on the intensity and location of the pain the users in the group feel. This data is transmitted over the internet to the centralized receiving module (30) which integrates each of the users' registered response data into an individual database (11) for that user, and also places all environmental data received from environmental monitors and associated with responses through those responses coining from the same location as the environmental data, and individual information associated with the responses, in the individual database (11) for that user (Four individual databases are shown, but if there are more than four users in the group, more than four individual databases are involved). In this embodiment, the centralized receiving module (30) would have previously placed environmental, location, and individual data associated with that user and also with previous time periods, in that user's individual database (11). The centralized receiving module (30) then copies the responses, together with all environmental, location, and individual information associated with the responses, from the individual database (11) for that user into the centralized integrated database (10). In this embodiment of the invention, the centralized receiving module (30) would have previously copied environmental, location, and individual data associated with previous time periods from the individual database (11) for each of the users into the centralized integrated database (10).

The healthcare provider's remote program (20), running on the healthcare provider's PC (42) accesses the individual database (11) for each of the users, and the healthcare provider can then use the app calculation module (22) of the healthcare provider's remote program (20) to perform calculations and graphing concerning the registered response data in the users' individual databases (11), and also concerning the combined registered response data in those individual databases (11). For example, the app calculation module may be asked to graph all of the group's users' registered responses for the past 24 hours on one graph. The centralized program (45) may have other components that are not shown because they are not relevant to the relationships shown in this drawing.

The healthcare provider, in this embodiment, can also command the app calculation module to give the healthcare provider an alert when a quantity in one of the users' registered response data, or in the above analysis's results, reaches a threshold, such as when the pain level registered by one of the patients reaches a threshold.

The app calculation module will perform the calculations and/or create the desired graphs, and the app transmission module (34) will transmit the calculations' results, and the graphs, to the app display module (25), which will use the PC's display capabilities to display the graphs results and/or calculations' results. The app calculation module will also produce an alert when the conditions the healthcare provider specified, for producing a warning alert when a warning threshold is exceeded, are met. The remote program (20) may have other components that are not shown because they are not relevant to the relationships shown in this drawing.

The healthcare provider, in this embodiment, can also command the app calculation module to give the healthcare provider an alert when a quantity in one or more of the users' registered response data, or the above analysis's results, reaches a threshold, such as when the nominated pain level one of the patients registered reaches a certain degree.

FIG. 12 shows a diagram of how a coordination module (16) can be used to quickly tell whether any patients, in a group of patients, are in distress, and how it is possible to prioritize the urgency of caring for the patients based on how much distress they are in. Here, the users in the group have not given their User IDs to the entity controlling the centralized integrated database (10). Each user in a user group, has access to multiple pain indicator units (1) connected to a processor (29). Three groups of pain indicator units connected to processors are shown, but the user group can have much more than three users, each of whom would have access to a different processor connected to multiple pain indicator units, and so there could be more than three processors, each connected to multiple pain indicator units. Each processor (29) is connected to a receiver (5), a transmitter (15), an alarm light (3), and an alarm (14), and multiple pain indicator units (1). One receiver (5), transmitter (15), alarm light (3) and alarm (14), connected to each processor (29) is shown in the drawing, but theoretically each processor could be connected to more than one receiver (5), transmitter (15), alarm light (3) and/or alarm (14), and to more pain indicator units than are shown in the drawing. The users' healthcare provider has a coordination module (16) running on an instrument including a processor (29), where the processor (29) is operatively connected to a transmitter (15) and multiple lights. The coordination module (16) uses the transmitter (15) to communicate with the receivers (5), and to tell them the sound that each of the alarms (3) should make when a patient uses the pain indicator unit (1) connected to a processor (29) which is connected to that alarm to register a response specifying pain, with a certain location and degree. Likewise, the coordination module (16) uses the transmitter (15) to communicate with the receivers (5), and tell them which visual indication each of the alarms (3) should make when a patient uses the pain indicator unit operatively connected to that alarm to register a response specifying pain of a certain location and degree.

The receivers (5) will transmit the information about which sound each alarm should make, and which visual indication each of the alarm lights should make, to the processors (29) connected to the pain indicator units. These processors (29) are also connected to the alarms (14) and alarm lights (3), and when one of the users activates a pain indicator unit (1), the processor (29) connected to that pain indicator unit will cause the alarm (14), alarm light (3), or both, connected to that processor (29), to make the visual indication, sound, or both, respectively, that the coordination module (16) has specified.

Those transmitters (15) that are connected to the processors (29) transmit the registered responses the users in the user group made. These registered responses are transmitted over the internet and reach the centralized receiving module (30), which saves the registered responses in the centralized integrated database (10). The centralized receiving module (30), in this embodiment, will also import environmental information from environmental monitors, and location data, associated with the responses, and a) Save this data in the centralized integrated database (10), and a) Save any individual data associated with the responses in the centralized integrated database (10). The centralized program (45) may have other components that are not shown because they are not relevant to the relationships shown in this drawing.

FIG. 13 shows a flow chart of one way that information about the pain patterns of a population of users can be assessed. The centralized receiving module (30) receives information about the users' responses, including, where available, the time, location, intensity, type, and duration of each response, and, where available, the User ID of the user who makes each response. Some users will have inputted their User IDs into the input devices they are using, and the transmitters in the input devices will send these User IDs as part of these users' responses registered on these input devices. In this case, each response also includes information about the medical conditions experienced by each user who sends that response, and individual information including, but not limited to, the user who sends that response's age and ethnicity. The centralized receiving module (30) saves the responses in the centralized integrated database (10). The centralized calculation module (28) then performs statistical calculations on the responses, that researchers have commanded the centralized calculation module (28) to perform. In this version of the invention, the centralized calculation module (10) then sends the statistical calculations' results to the integrated statistical display, which displays these results for researchers to use. The centralized program (45) may have other components that are not shown because they are not relevant to the relationships shown in this drawing.

FIG. 4a shows a mouth model (8) with several position sensors (19) attached to pain indicator units (1). The position sensors that are broadcasting are indicated, showing that each position sensor can detect the other position sensors, and their locations relative to that position sensor (The "first position sensor").

FIG. 14b shows one way in which a nearby processor might read the position sensors in the same mouth model's locations relative to each other.

FIG. 14e shows the same mouth model (8) as FIG. 14a with two of the teeth moved. The pain indicator units and position sensors on those teeth are also moved. The position sensors continue to broadcast, to detect each other, and to broadcast their locations relative to each other, which means that each first position sensor is able to detect the new location of every other position sensor relative to the first position sensor.

FIG. 14d shows how a nearby processor might read the position sensors in the mouth model's locations relative to each other, after the two teeth and the attached position sensors have been moved.

FIG. 15 shows a flow chart of how the pain patterns of users in a user group can be assessed. A first user group with a specific health condition creates responses using pain indicator units (1) that are located on proxy models (26), part models (17), mouth models (8), and human body models (9), and pain indicator units (1) that are attached to suction cups (13), that are in turn attached to beds (pieces of furniture) where the beds are pain indicator pieces (32). The beds are shown smaller than their actual size here, Some of the proxy models (16) have covers (31) on them. Transmitters (15) operatively connected to the proxy models (26), part models (17), mouth models (8), and human body models (9), and the pain indicator units attached to the pain indicator pieces (beds) broadcast responses, which are received by a centralized receiving module (30). Twelve input devices are shown, with reference to the first group, but the first user group can include more than twelve users, each of whom would have access to at least one input device. A second user group of users with the same specific health condition use pain indicator virtual units (35) running as part of app calculation modules (22) in remote programs (20) on their cellular phones (A type of PC) to indicate when they are feeling pain, and how much pain they are feeling. The cellular phones broadcast the responses from the second user group. Two cellular phones are shown, but the second group can include more than two users, each with a PC, The centralized receiving module (30) receives responses from both groups of users over the internet, and a) Places these responses in the centralized integrated database (10), and b) Places each individual user's responses in an individual database (11) for that individual user. In this embodiment, researchers can then command the centralized calculation module (28) to create a specialized database (33) comprising only responses from those users that have the aforementioned health condition. In this embodiment, the centralized calculation module (28) will do this by searching the centralized integrated database (10) for individual information mentioning that specific health condition, finding the users associated with that individual information, and creating the specialized database (33) from those users' responses. In other embodiments, the centralized calculation module (28) can search through users' individual databases to find users who have the specific health condition mentioned in their individual information.

Researchers can also command the centralized calculation module (28) to make statistical calculations and create graphs, based on the data in the specialized database (33), or data in the centralized integrated database (10), or in individual databases (11). The integrated statistical display (27) can display the results of these calculations, and graphs. Here, the integrated statistical display (27) sends the calculations' results, and the graphs, that a group of researchers requested the centralized calculation module (28) to make, to those researchers' PCs (42), for the researchers to view and/or save, or to another location the researchers desire.

The responses broadcast from the second user group's PCs (42) will also be received by a PC (42) controlled by an individual healthcare practitioner (A type of healthcare provider), with whom the users in the second group of users have a prior relationship. The users in the second group of users have already given permission for this specific healthcare practitioner to receive these responses. The healthcare provider's app receiving module (24) will receive the responses and store the responses in an app database (44) on the healthcare practitioner's PC. The healthcare practitioner, in this embodiment, will also be able to access the individual databases (11) of the users in the second group of users. The healthcare practitioner is able to use the app input module (36) to tell the app calculation module (22) to make statistical calculations and create graphs, concerning the responses of the users in the second group, which are stored in the healthcare provider's app database (44).

In this version of this embodiment, the healthcare practitioner can do this by using the app input module (36) to command the integrated statistical display (27) to tell the centralized calculation module (28) to make desired calculations and create graphs the healthcare practitioner desires (In other versions of this embodiment the app input module (36) would directly command the centralized calculation module (28) to make the desired calculations and graphs). The graphs' results and calculations' results will then be sent to the app receiving module (24), and the app receiving module (24) will send them to the app display module (25), which will then display these graphs' and calculations' results. In this version of the invention, the centralized calculation module can send graphs and results of statistical calculations to a specific remote program's app receiving module, which can then send them to that remote program's app display module for display. In other versions of this embodiment, and some other embodiments, the graphs and calculations' results may be sent in other pathways, including, but not limited to, A. Being sent directly from the centralized calculation module (28) to the app display module, which then displays the graphs and calculations' results. B. Being sent directly from the centralized calculation module (28) to a part of the remote program outside of the app display module or app receiving module, which will then display the graphs and calculations' results. C. The app input module (36) directly sending the command about which graphs and calculations to make, to the centralized calculation module (28), and/or the app calculation module directly sending the graphs and calculations to the app display module, app receiving module, or another part of the remote program. D. The graphs and results of the calculations being sent from the centralized calculation module (28) to another piece of software on the healthcare practitioner's PC, or displayed by a component of the centralized program (45) and visible to the healthcare practitioner through the healthcare practitioner accessing the centralized program (45) over the internet (Such as the integrated statistical display (27) displaying the graphs and calculations' results in a way through which the integrated statistical display (27) can show them to the healthcare practitioner on a website when the healthcare practitioner is accessing the integrated statistical display (27) over the internet), or E. The healthcare practitioner using another part of the remote program (20), not the app input module (36), to send commands about which calculations to make and graphs to display, directly to the centralized calculation module (28), or to the integrated statistical display (27), which will then send the commands to the integrated calculation module.

Note that twelve individual databases are shown for the first group of users and second group of users combined, but, since each user has an individual database, there will be more than twelve individual databases if there are more than twelve users.

The healthcare practitioner will also be able to use the app input module (36) to tell the app calculation module (22) to make statistical calculations and create graphs, concerning the responses of the users in the second group, in those users' individual databases (11). In this version of the invention, the healthcare practitioner can also use the healthcare practitioner's remote program (20) to access the centralized integrated database (10) and use the app input module (36) to tell the app calculation module (22) to make specific statistical calculations and create specific graphs concerning data in the centralized integrated database (10). Information in the centralized integrated database (10), such as datapoints in the centralized integrated database (10) is sent to the centralized calculation module (28), which sends this information to the integrated statistical display (27), in this embodiment. The integrated statistical display (27) then sends the data to the app receiving module (24), in this embodiment. The app receiving module (24) can then send this information to the app display module (25) for display and examination by the healthcare practitioner. The app calculation module (22) also does other calculations and graphs, at the user's request, and the app transmission module (34) sends the results of these calculations and graphs to the app display module (25) for display and examination by the healthcare practitioner.

In other embodiments, there are other paths by which the data could move from the centralized integrated database (10) to the app calculation module (22). These paths include, but are not limited to, A. The data being moved directly from the centralized integrated database (10) to the app calculation module (22), and B. The data being moved from the centralized integrated database (10) to the app receiving module (24), and from there to the app calculation module (22). The healthcare practitioner can also set warning thresholds related to all the responses. For example, the healthcare practitioner can set a warning threshold when the average pain level the second group of users express increases by a certain amount in an hour. The centralized program (45) and the remote programs (20) running on the PCs may have other components that are not shown because they are not relevant to the relationships shown in this drawing.

FIG. 16 shows an example of a part model (17) of a user's head and upper neck, divided into several pieces that can interlock, Each one of the pieces has at least one pain indicator unit, and a transmitter (15), and the pain indicator units (1) in each piece are operatively connected to the transmitter (15) in that piece. A user can press one of the pain indicator units to show that he/she is experiencing pain in that part of his/her head. Embodiments like this can be used, among other purposes, to alert a user when the user need to seek medical attention for an area of the user's head or neck, in situations such as when the user's total pain level or rate of increase of pain in a body part exceeds a certain threshold. These embodiments are also useful in remote diagnoses in telemedicine, because a healthcare provider can use a user's registered responses, that are communicated to that healthcare provider over the internet, to help make a diagnosis.

FIG. 17 shows two proxy models (26), each of which is supposed to represent half of a user's head. The two proxy models include pain indicator units (1) that are buttons that the user can press. Both proxy models (26) include transmitters (15) that are operatively connected to the pain indicator units, and the transmitters wirelessly broadcast responses that users make, using the pain indicator units. The user pressing each pain indicator unit (1) on each proxy model represents pain in a specific area of the user's head. The users using the proxy models have previously been informed about which pain indicator unit, on each proxy model, a user should press to indicate pain in each area of the user's head. The nearby app receiving module (24), which is part of a remote program (20), running on a PC (42), receives the wireless responses. The remote program (20) may have other components that are not shown because they are not relevant to the relationships shown in this drawing.

FIG. 18 shows an embodiment of the invention where a healthcare provider uses the invention to keep track of the locations and intensity of the pain being experienced by members of multiple subgroups in a group of users. Users in some of the user subgroups, comprising users who are outpatients, each have a remote program (20), on their cellular phones (A type of PC (42)). The remote programs each include pain indicator virtual units (35) representing different areas of the user's body. On each of the PCs' screens, a figure of a human can be seen, divided into sections. The sections are pain indicator virtual units (35). The remote programs (20) also each include an app input module (36), with which a user using one of the remote programs can make calculations and view graphs related to that user's pain, in different body parts, over time. Each cellular phone also has a data export port (41) in the form of that cellular phone's USB port. Three PCs (42) are pictured, but each of the user subgroups including users who are outpatients can comprise more than three members, each member with a PC. Some of the user subgroups, comprising some users who are inpatients, and some users who are outpatients, have human body models (9), with pain indicator skins (43). Each human body model also has an ID input port (40), where a user can input the user's User ID, such as a fingerprint. The human body models (9) each also have a data export port (41), and a time division indicator (39), and a transmitter (15). The transmitter (15) in each of the human body models (9) broadcasts the degrees and locations of the pain the user of that human body model is feeling, along with the time division indication that the user of that human body model has selected with the time division indicator. Three human body models (42) are pictured, but each of the user subgroups can comprise more than three members, each member with a human body model. A display device (38) shaped like a rod, with a receiver (5), which is operatively connected to a processor (29), where the display device (38) has lights, that the processor controls, will find and indicate the part of the pain scale in use that includes, the average pain level expressed by each member of each user subgroup, in each timestretch of the time division that user selected. The processor will calculate the average of the highest pain level expressed by each user in the subgroup, in each timestretch of the time division that user selected, and the processor will assume, for purposes of calculating this average, that if a user has selected a longer time division, the highest pain level expressed by that user in a timestretch applies to every subpart of that timestretch. For example, if some users in a subgroup have selected 1 minute as their time division, and one user in the subgroup has selected 1 hour as that user's time division, and that user expresses a highest pain level of 5 during an hour, then, when calculating the average, the processor in the display device will assume that the pain level of 5 is also the highest pain level that user expressed in each minute of that hour. Each light will shine in a color governed by the range within which falls the average pain level the users within a specific subgroup expressed, within the timestretches of the time divisions the users in that subgroup selected. Each part of the range of possible averages will correspond to a specific color, for each light (A.k.a. from 0-1 corresponds to one color, from 1-2 another color, etc.). If the average pain level the users in a subgroup express the timestretches of the time divisions the users in that subgroup selected increases at a rate above a certain threshold, the processor will cause the light corresponding to that subgroup of users to glow more brightly. The threshold is programmed into the processor. For example, if the average pain level the users in a subgroup express in the timestretches of the time divisions the users in that subgroup selected increases by 1 in a 1-hour period, the light representing that subgroup may glow more brightly. If it increases by 2 in a 1-hour period, the light representing that subgroup may glow even more brightly. The processor in the display device (38) also controls the brightness with which the lights glow. The healthcare provider can view the display device, and quickly assess when one subgroup of users is feeling a large amount of pain (like when the app calculation module calculates an average pain level expressed by that subgroup of users which is high enough to give cause for concern) or their average pain level is increasing rapidly, and the healthcare provider can then contact the users in that subgroup to help them.

The processor in the display device is also programmed with a coordination module (16), that causes an alarm (14) in the display device to make a different noise when each of the users using a human body model indicates that this user is feeling a high pain degree on the pain scale being used.

The noise the display device makes is different depending on which user indicates that the user is feeling a high pain degree. In this version of the invention, the noise the display device, makes, when a user is feeling a pain of a specific high pain degree or higher, is the room number where that user and the human body model the user is using are located. The display device (38) may be located in an area where the healthcare provider may easily take action if the average pain level reported by users in a subgroup gets too high, such as the reception desk of a hospital department where some of the users are patients. The remote program (20) may have other components that are not shown because they are not relevant to the relationships shown in this drawing.

The invention claimed is:

1. A method of monitoring a user's pain degree, that the user feels, said method further comprising providing one or more pain indicator units, each pain indicator unit being operatively connected to either an alarm, alarm light, or both an alarm, and alarm light;

said method further comprising that when the user activates any of said one or more pain indicator units, any alarm operatively connected to the activated pain indicator unit will make an alarm signal, and any alarm light operatively connected to the activated pain indicator unit will make a visual signal;

said method further comprising providing that one or more of said one or more pain indicator units are attached to input devices, said input devices belonging to a group comprising part models, human body models, mouth models, and proxy models;

said method further comprising providing that each said input device includes a transmitter, where each said transmitter is operatively connected to any pain indicator units in the input device that includes said transmitter, said method further comprising that when any said pain indicator unit is activated the activated pain indicator unit will communicate to the transmitter in the input device that includes the activated pain indicator unit that the activated pain indicator unit is activated;

said method further comprising providing that each said transmitter is capable of broadcasting a transmission including any information that transmitter receives from any said pain indicator unit in the input device that includes said transmitter;

said method further comprising providing at least one receiver, which is able to directly or indirectly receive information broadcast by said transmitters;

said method further comprising providing that at least one said alarm light is operatively connected to said receiver, and that said at least one said alarm light will make a visual signal when said at least one said alarm light receives a signal from said receiver that a user has activated one of said pain indicator units;

said method further comprising providing that at least one said alarm is operatively connected to said receiver, and that said at least one said alarm will make a sound when said at least one said alarm receives a signal from said receiver that the user has activated one of said pain indicator units;

said method further comprising providing a means for identifying which pain indicator unit a user activates, when the user activates one of the pain indicator units.

2. The method of claim 1, said method further comprising providing that said user can manipulate at least one of said one or more pain indicator units in a specified way in different amounts to show the degree of pain said user feels;

said method further considering designing said at least one of said one or more pain indicator units so that said at least one of said one or more pain indicator units can be manipulated to different amounts in said specified way;

said method further comprising providing that said at least one of said one or more pain indicator units is marked in a way that allows a user to visually determine how much the user has manipulated said at least one of said one or more pain indicator units in said specified way.

3. The method of claim 1, said method further comprising providing that said user can manipulate at least one of said one or more pain indicator units in a specified way in different amounts to show the degree of pain said user feels;

said method further comprising designing said at least one of said one or more pain indicator units so that said at least one of said one or more pain indicator units can be manipulated to different amounts in said specified way; said method further comprising providing that either any alarm operatively connected to said at least one of said one or more pain indicator units can make different sounds, and the sound said alarm will make when said at least one of said one or more pain indicator units is activated will vary depending on the amount to which said at least one of said one or more said pain indicator units operatively connected to said alarm is manipulated by said user in said specified way;

or any alarm light operatively connected to said at least one of said one or more pain indicator units can make different visual signals, and the visual signal said alarm light will make when said at least one of said one or more pain indicator units is activated will vary depending on the amount to which said at least one of said one or more pain indicator units operatively connected to said alarm light is manipulated by said user in said specified way;

or both any alarm operatively connected to said at least one of said one or more pain indicator units can make different sounds, and the sound said alarm will make when said at least one of said one or more pain indicator units is activated will vary depending on the amount to which said at least one of said one or more pain indicator units operatively connected to said alarm is manipulated by said user in said specified way and any alarm light operatively connected to at least one of said one or more pain indicator units can make different visual signals, and the visual signal said alarm light will make when said at least one of said one or more pain indicator units is activated will vary depending on the amount to which said at least one of said one or more pain indicator units operatively connected to said alarm light is manipulated by said user in said specified way.

4. The method of claim 1, said method further comprising that one or more of said input devices includes a cover which can partly or fully enclose at least one of the pain indicator units in said input device that includes the cover.

5. The method of claim 1, said method further comprising that each said input device includes either at least one of said alarms, operatively connected to at least one of the pain indicator units in said input device, or at least one of said alarm lights, operatively connected to at least one of the pain indicator units in said input device, or at least one of said alarms, operatively connected to at least one of the pain indicator units in said input device, and also at least one of said alarm lights, operatively connected to at least one of the pain indicator units in said input device.

6. The method of claim 1, said method further comprising providing that one or more of said part models, human body models, proxy models, and mouth models is attached to a means for adhering, where said means for adhering is of sufficient strength to adhere said part model, human body model, proxy model, or mouth model attached to said means for adhering to another object.

7. The method of claim 1, said method further comprising providing that one or more of said input devices includes a battery to power some or all components of the input device that includes said battery, and a battery charger which is able to recharge said battery.

8. The method of claim 1, said method further comprising providing that one or more of said input devices includes a solar panel, where said solar panel is capable of providing electrical power to some or all of the components of the input device that includes said solar panel.

9. The method of claim 1, said method further comprising providing that at least one of said one or more pain indicator units is not part of a proxy model, mouth model, part model, or human body model, and is operatively connected to a transmitter and a means for adhering, where said means for adhering is of sufficient strength to adhere said at least one of said one or more pain indicator units to a pain indicator piece, and where said transmitter is capable of broadcasting a transmission including any information that transmitter receives from said at least one of said one or more pain indicator units so that said transmission including said information is received by at least one of said receivers.

10. The method of claim 1, said method further comprising providing one or more of;

a display section operatively connected to at least one said receiver, where said display section is able to process information transmitted by one or more of said transmitters and received by said receiver, and to show data on the screen of said display section, where said data includes representations of how much, and when, each of said pain one or more pain indicator units operatively connected to a one of said transmitters that broadcasts transmissions received by said receiver has been activated;

and a human body display operatively connected to said receiver, where said human body display is capable of displaying an image of a human body, and changing said image of a human body in response to the result of calculations on said information in one or more transmissions that have been broadcast by any of said transmitters and received by said receiver.

11. The method of claim 10, said method further comprising providing that a viewer can input a refining function into said display section or said human body display, and said display section or human body display will then apply said refining function to data concerning users' pain that said display section or human body display receives from said receiver.

12. The method of claim 1, said method further comprising providing that at least one of said input devices includes a memory, and a data export port, operatively connected to said memory; and the input device including the memory and data export port further includes that at least one pain indicator unit in said input device that includes said memory and data export port is operatively connected to said memory and, when activated, sends information to said memory which is recorded in said memory, and said method further comprising that the information sent from pain indicator units in the input device including the memory and data export port to said memory and recorded in said memory may be sent from said memory to said data export port and exported out of said data export port.

13. The method of claim 1, said method further comprising providing a coordination module, and further providing an electronic device on which said coordination module is run;

said method further comprising that at least one of said alarms is an alarm capable of making more than one kind of sound, said method further comprising that at least one of said alarm lights is an alarm capable of making more than one kind of visual signal;

said method further comprising providing that said coordination module is capable of operatively communicating with some or all of said alarm lights capable of making more than one kind of visual signal and said alarms capable of making more than one kind of sound, and causing each of those alarms with which said coordination module is capable of operatively communicating to make a sound when said receiver receives a signal from at least one specific input device that a user has activated one of the pain indicator units in said specific input device which is different from the sound which said alarm makes when said receiver receives a signal from at least one different specific input device that a user has activated one of the pain indicator units in said different specific input device;

and causing each of those alarm lights with which said coordination module is capable of operatively communicating to make a visual signal when said receiver receives a broadcast from at least one specific input device that a user has activated one of the pain indicator units in said specific input device which is different from the visual signal which said alarm light makes when said receiver receives a broadcast from at least one different specific input device that that a user has activated one of the pain indicator units in said different specific input device.

14. The method of claim 1, said method further comprising providing that some or all of said one or more pain indicator units that are in in at least one of said input devices are part of a pain indicator skin, which is part of said at least one of said input devices.

15. The method of claim 1, said method further comprising providing that one or more individual users can each establish an account with a centralized program, and, said centralized program will create an individual database for each of said one or more individual users who establishes an account with said centralized program;

said method further comprising providing that some or all of said input devices are input devices with means for identifying, wherein an input device with means for identifying includes a capability to identify which of said one or more individual users activates said input device with means for identifying;

said method further comprising providing that when one of said one or more individual users activates one or more of said one or more pain indicator units in an input device with means for identifying, the transmitter in said input device with means for identifying broadcasts a transmission saying that said one or more of one or more pain indicator units was activated, creating an activation, and also including an identification of said one of said one or more individual users who activated said one or more pain indicator units in said input device with means for identifying; to said receiver;

said method further comprising providing that said cen-
tralized program has access to the individual databases
for said one or more individual users;

said method further comprising providing that, when said
receiver receives a transmission broadcast from a trans-
mitter, said receiver sends to said centralized program
a record of at least the following information about said
activation, that is present in said transmission that is
broadcast from said transmitter and that is received by
said receiver;

a. the identification of the one of said one or more
individual users who activated one or more pain indi-
cator units, operatively connected to said transmitter;

b. which pain indicator units operatively connected to said
transmitter were activated by said one of said one or
more individual users;

c. the pain degree said one of said one or more individual
users indicated when said one of said one or more
individual users activated each of said pain indicator
units operatively connected to said transmitter;

said method further comprising that said centralized pro-
gram uses said identification of the one of said one or
more individual users, who activated one or more pain
indicator units operatively connected to said transmit-
ter, to find the individual database of the one of said one
or more individual users who activated one or more
pain indicator units operatively connected to said trans-
mitter, and place said record in the individual database
for said one of said one or more individual users, who
activated one or more pain indicator units operatively
connected to said transmitter;

said method further comprising that each said individual
database includes records of activations of said one or
more pain indicator units by only one user.

16. The method of claim 15, said method further com-
prising providing that said centralized program is capable of
performing statistical analysis on the records included in the
individual database for each one of said one or more
individual users and said method further comprising that
said centralized program, is capable of showing the results
of said statistical analysis performed by said centralized
program.

17. The method of claim 16, said method further com-
prising calculating an expected change in a statistical mea-
surement of the pain degree experienced by a category of
users, in response to a change in conditions experienced by
the users in said category of users, by the steps of;

i. providing that the centralized program receives external
information, said external information being data
points expressing information about one or more of a
group of one or more external information categories
including, environmental information and health con-
ditions of members of users in said category of users;

ii. providing that said centralized program stores said
external information in said centralized integrated data-
base;

iii. selecting information included in data points stored in
said centralized integrated database, said information
being qualitative or quantitative measurements of one
or more external information categories or results of a
statistical equation applied to qualitative or quantitative
measurements of one or more external information
categories that are a part of said data points stored in
said centralized integrated database, to use as indepen-
dent variable data points representing values of one or
more independent variables, and selecting a category of measurements created through
said activations and that are included in data points that
are stored in said centralized integrated database, or are
results of a statistical equation applied to the measure-
ments in said category of measurements created
through said activations, that are included in data points
that are stored in said centralized integrated database, to
use as dependent variable data points representing a
dependent variable;

iv. inputting, as training data, into an artificial neural
network, the measurements of the independent vari-
ables in a first group of independent variable data
points, and the measurements of the dependent variable
in a first group of dependent variable data points, which
can, but does not have to, be the same as the first group
of independent variable data points;

v. finding, from the values that said training data depen-
dent variable in said training data has when one or more
different combinations of said training data indepen-
dent variables occur in said training data, the combi-
nations of changes of said training data independent
variables that coincide with changes in the value of said
training data dependent variable;

vi. finding the values of the weights and activation ener-
gies of the artificial neurons within said artificial neural
network where the differences between the actual val-
ues of the changes in the dependent variable in said
dependent variable data points and the changes in the
values of the data points of said training data dependent
variable that said artificial neural network predicts
based on the values of the independent variables in the
training data independent variable data points, and the
weights and activation energies of the artificial neurons
in said artificial neural network, are minimized;

vii. inputting as test data, into said artificial neural net-
work, the measurements of the independent variables in
a second group of independent variable data points, and
the measurements of the dependent variable in a second
group of dependent variable data points, which can, but
does not have to, be the same as the second group of
independent variable data points;

viii. calculating whether the weights and activation ener-
gies of the artificial neurons in said artificial neural
network should be changed, based on the data points in
said test data, to minimize the difference between the
actual value of the data point of said training data
dependent variables and the values of the data points of
said training data dependent variable that are predicted
based on the values of the data points of the training
data independent variables and the weights and activa-
tion energies of the artificial neurons in said artificial
neural network;

ix. repeating steps vii and viii as many times as desired;

x. communicating, to an entity using said artificial neural
network, said weights and activation energies where
the differences between the actual values of said depen-
dent variable and the values of said dependent variable
that are predicted based on the weights and activation
energies of the artificial neurons within said artificial
neural network are minimized.

18. The method of claim 16, said method further com-
prising providing remote programs, wherein each said
remote program can be run on a PC, wherein each said
remote program is able to connect to the individual database
of at least one of said one or more individual users, said method further comprising providing that, when said
at least one of said one or more individual users feels pain, said at least one of said one or more individual users can use said remote program to indicate the identification of said at least one of said one or more individual users, and to identify body parts where said at least one of said one or more individual users feels pain, and to identify the pain degree that said at least one of said one or more individual users feels;

and said method further comprising that said PC will then broadcast a transmission including the identification of said at least one of said one or more individual users, the identities of the body parts where said one or more individual users feels pain, and the degree of pain that said one or more individual users feels, and the time that said one or more individual users used said remote program to indicate that said one or more individual users was feeling pain;

said method further comprising providing that when said receiver receives a transmission broadcast from said PC, said receiver sends to said centralized program a record of the following information that was included in said transmission;

the identification of said one of said one or more individual users, the identification of body parts where said one of said one or more individual users feels pain, and the degree of pain that said one of said one or more individual users feels in each of said body parts, and the time that said one or more individual users used said remote program to indicate that said one or more individual users was feeling pain;

said method further comprising providing that said centralized program will use the identification of said one of said one or more individual users to locate the individual database of said one of said one or more individual users, and will save, in the individual database of said one of said one or more individual users, the following information that was included in said transmission;

the identification of body parts where said one of said one or more individual users feels pain, and the degree of pain that said one of said one or more individual users feels, and the time that said one of said one or more individual users used said remote program to indicate that said one of said one or more individual users was feeling pain.

19. The method of claim 15, said method further comprising providing that said centralized program is capable of performing statistical analysis on information included in the individual databases for said one or more individual users, and said centralized program is capable of showing the results of said statistical analysis performed by said centralized program on information included in the individual databases of said one or more individual users;

said method further comprising providing a centralized integrated database in which said centralized program can save information;

said method further comprising providing that said centralized program saves in said centralized integrated database records of activations included in transmissions broadcast from one or more of said transmitters and received by one or more of said one or more receivers, and then communicated from said one or more of said receivers to said centralized program;

said record of each said activation including at least the following;

d. the identification of the one of said one or more individual users who performed said activation by activating one or more pain indicator units, operatively connected to said transmitter that broadcast said transmission;

e. which pain indicator units operatively connected to said transmitter that broadcast said transmission were activated, as part of said activation, by said one of said one or more individual users;

f. the pain degree said one of said one or more individual users indicated when said one of said one or more individual users activated each of said pain indicator units operatively connected to said transmitter that broadcast said transmission;

said method further comprising providing that said centralized program is capable of performing statistical analysis on records included in each of said individual databases, and said centralized program is capable of performing statistical analysis on records located in the centralized integrated database;

said method further comprising providing that said centralized program is capable of performing statistical analysis of datasets comprising information saved in the individual databases for one or more individual users, and information saved in the centralized integrated database;

said method further comprising providing that said centralized program is capable of displaying the results of said statistical analysis performed by said centralized program.

20. The method of claim 15, said method further comprising providing remote programs, wherein each said remote program can be run on a PC, wherein each said remote program is able to connect to the individual database of at least one of said one or more individual users, said method further comprising providing that each said remote program is capable of performing statistical analysis on information in said individual database for at least one of said one or more individual users, to which said remote program is able to connect, and said method further comprising providing that each said remote program is capable of displaying the results of said statistical analysis.

21. The method of claim 15, said method further comprising Providing remote programs wherein each said remote program can be run on a PC, wherein each said remote program is able to connect to the individual database of said one or more of said one or more individual users;

said method further comprising providing that each said remote program is capable of performing statistical analysis on the information in said individual database of said at least one of said one or more individual users, and displaying the results of said statistical analysis; and said method further comprising providing a centralized integrated database;

and said method further comprising providing that said centralized program saves in said centralized integrated database information about any said activation that is broadcast in any transmission, from one or more transmitters, that at least one of said receivers receives from said one or more transmitters and sends to said centralized program;

said method further comprising providing that said centralized program is capable of performing statistical analysis on the records of activations included in the individual database for each of said one or more individual users, and capable of performing statistical analysis on the records of activations located in the centralized integrated database;

said method further comprising providing that said centralized program is capable of performing statistical analysis on groups of data points comprising both information saved in the individual databases of one or more of said one or more individual users, and information saved in said centralized integrated database;

said method further comprising providing that said centralized program, shows the results of said statistical analysis performed by said centralized program.

22. The method of claim 21, said method further comprising providing that each said remote program is capable of connecting to said centralized integrated database and performing statistical analysis on records of activations stored in said centralized integrated database, and displaying the results of said statistical analysis.

23. The method of claim 15, said method further comprising providing a centralized integrated database in which said centralized program can save information, and said method further providing that said centralized program associates either a. the time that each of said activations of any of said pain indicator units happened, if any of said transmitters broadcasts said time the activation happened, or b. if none of said transmitters broadcasts said time the activation happened, the time that the centralized program receives the first said transmission that includes information about said activation, with the record of said activation that is included in the individual database of said one of said one of said one or more users who performed said activation, and with the record of said activation that is included in the centralized integrated database.

24. The method of claim 15, said method further comprising providing a centralized integrated database;

and said method further comprising providing that said centralized program saves in said centralized integrated database the following information about each said activation that is included in transmissions that are broadcast, from said one or more transmitters and received by at least one of said receivers and sent by said at least one of said receivers to said centralized program;

d. the identification of the one of said one or more individual users who did said activation;

e. which pain indicator units operatively connected to said transmitter that broadcast said transmission were activated in said activation;

f. the pain degree said one of said one or more individual users indicated when said one of said one or more individual users activated each said pain indicator unit that was activated as part of said activation;

that is included in the centralized integrated database;

said method further comprising providing that the centralized program receives data points comprising data from a group of one or more external information categories including, but not necessarily limited to, environmental information and health conditions of said one or more individual users;

and said method further comprising providing that said centralized program associates either the time of each said activation, or the time that the centralized program receives the first said transmission that includes information about each said activation, with the record of;

g. the identification of the one of said one or more individual users who did said activation;

h. which pain indicator units operatively connected to said transmitter that broadcast said transmission were activated in said activation;

i. the pain degree said one of said one or more individual users indicated when said one of said one or more individual users activated each of said pain indicator units that was activated in said activation;

that is included in the individual database of said of said one or more users who did said activation, and with the record of j. the identification of the one of said one or more individual users who did said activation;

k. which pain indicator units operatively connected to said transmitter that broadcast said transmission were activated in said activation;

l. the pain degree said one of said one or more individual users indicated when said one of said one or more individual users activated each said pain indicator unit that said one of said one or more individual users activated as part of said activation; that is included in the centralized integrated database;

said method further comprising either examining statistical relationships between external information recorded in said centralized integrated database and the pain degree recorded in said centralized integrated database, and informing one or more of said one or more users of any detected statistical relationships between external information recorded in said centralized integrated database and the pain degree recorded in said centralized integrated database; or examining statistical relationships between external information recorded in said individual database of said one of said one or more users and the pain degrees included in activations recorded in said individual database of said one of said one or more users, and informing said one of said one or more of said one or more users of these statistical relationships; or examining statistical relationships between external information recorded in said centralized integrated database and the pain degree recorded as part of a the record of said activation, in said centralized integrated database, and informing said one or more users of these statistical relationships and also examining statistical relationships between external information recorded in said individual database of said one of said one or more users and the pain degree recorded in said individual database of said one of said one or more users, and informing said one of said one or more users of these statistical relationships.

* * * * *